(12) United States Patent
Zheng et al.

(10) Patent No.: US 7,285,341 B2
(45) Date of Patent: Oct. 23, 2007

(54) COMPLEX FLUORENE-CONTAINING COMPOUNDS FOR USE IN OLED DEVICES

(75) Inventors: Shiying Zheng, Webster, NY (US); Kathleen M. Vaeth, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 258 days.

(21) Appl. No.: 11/122,962

(22) Filed: May 5, 2005

(65) Prior Publication Data
US 2005/0202279 A1  Sep. 15, 2005

Related U.S. Application Data

(63) Continuation-in-part of application No. 10/335,441, filed on Dec. 31, 2002, now abandoned.

(51) Int. Cl.
*H01J 1/62* (2006.01)
*C09K 11/06* (2006.01)

(52) U.S. Cl. .................. 428/690; 428/917; 313/504; 313/506; 257/40; 257/102; 257/103; 252/301.16

(58) Field of Classification Search ............. 428/690, 428/917; 313/504, 586; 257/40, 102, 103; 252/301.16; 315/506
See application file for complete search history.

(56) References Cited

U.S. PATENT DOCUMENTS 6,686,065 B2 * 2/2004 Chen ............... 428/690
6,849,348 B2 * 2/2005 Zheng et al. ........ 428/690

OTHER PUBLICATIONS

Yang et al, Organic/polymeric electroluminescent devices processed by hybrid ink-jet printing, Journal of Material Science, Mater. Electron, 2000, 11, 89-96.

Bernius et al, Progress with Light-Emitting Polymers, Adv. Mater. 2000, 12, 1737-1750.

Burroughes et al, Light-emitting diodes based on conjugated polymers, Nature 1990, 347, 539-541.

* cited by examiner

*Primary Examiner*—Rena Dye
*Assistant Examiner*—Camie S. Thompson
(74) *Attorney, Agent, or Firm*—Raymond L. Owens

(57) ABSTRACT

An organic compound comprising a complex fluorene structure represented by the following Formula:

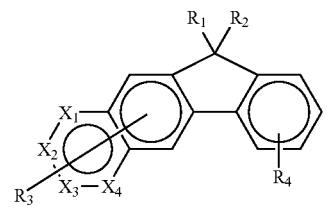

wherein:

$X_1$, $X_2$, $X_3$, and $X_4$ include carbon atoms and at least one nitrogen atom; $R_1$, $R_2$, $R_3$, and $R_4$ are substituents each being individually hydrogen, or amino, or alkyl, or alkenyl, or alkynyl, or alkoxy of from 1 to 40 carbon atoms; aryl or substituted aryl of from 6 to 60 carbon atoms; or heteroaryl or substituted heteroaryl of from 4 to 60 carbons; or F, Cl, or Br; or a cyano group; or a nitro group; or $R_3$, or $R_4$ or both are groups that form fused aromatic or heteroaromatic rings; or $R_1$ and $R_2$ together form a cyclic ring having 3 to 20 carbon, nitrogen, sulfur or oxygen atoms; or $R_1$ and $R_2$ together form a double bond moiety.

4 Claims, 4 Drawing Sheets

COMPLEX FLUORENE-CONTAINING COMPOUNDS FOR USE IN OLED DEVICES

CROSS REFERENCE TO RELATED APPLICATION

This is a continuation-in-part of application Ser. No. 10/335,441 filed Dec. 31, 2002 now abandoned entitled "Complex Fluorene Containing Compounds for Use in OLED Devices" by Shiying Zheng, et al.

FIELD OF THE INVENTION

The present invention relates to organic compounds containing a complex fluorene and their uses in an electrical-optical device such as an electroluminescent (EL) device.

BACKGROUND OF THE INVENTION

There is a great need for large area solid state light sources for a series of applications, especially in the file of display elements and lighting engineering. The demands cannot be fully satisfactorily met by any of the existing technologies. Electroluminescent devices such as light-emitting diodes represent an alternative to conventional display and lighting elements. Electroluminescent devices are optoelectronic devices where light emission is produced in response to an electrical current through the device. The physical model for EL is the radiative recombination of electrons and holes. Both organic and inorganic materials have been used for the fabrication of LEDs. Inorganic materials such as ZnS/Sn, Ga/Bs, Ga/As have been used, e.g. in semiconductor lasers, small area displays, and LED lamps. However, the drawbacks of inorganic materials include difficulties to process and to obtain large surface areas and efficient blue light.

Organic materials, which includes both small molecules and polymeric materials, offer several advantages over inorganic materials for LEDs, such as simpler manufacturing, low operating voltages, the possibility of producing large area and full-color displays. Conjugated polymers such as poly(phenylvinylene) (PPV) were first introduced as EL materials by Burroughes, et al. in 1990 (Burroughes, J. H. *Nature* 1990, 347, 539-41). Tremendous progress has been made since then to improve the stability, efficiency, and durability of polymeric LEDs (Bernius, M. T., et al., *Adv. Mater.* 2000, 12, 1737). Organic LED (OLED) represents an alternative to the well established display technologies based on cathode-ray tubes and liquid crystal displays (LCDs), especially for large area displays. OLED has been demonstrated to be brighter, thinner, lighter, and faster than LCDs. Moreover it requires less power to operate, offers higher contrast and wide viewing angle (>165 degree), and has great potential to be cheaper to make, especially the polymer-based LEDs (PLED).

The OLED technology has stimulated intensive research activities across all disciplines. Currently, great efforts in materials research have been focused on novel materials for full-color flexible displays. Full-color displays require three basic colors, red, green and blue, and flexible substrates require low temperature and easy processing of the organic materials. PLED devices show great promise in meeting both requirements, since the emission color can be tailored by modulation of the chemical structures and the solution processing permits for micro-patterning of the fine multi-color pixels via inkjet printing technique (Yang, Y., et al., *J. Mater. Sci.: Mater. Elecron.*, 2000, 11, 89). However, processable, stable, and efficient blue light-emitting organic materials are still highly desirable to meet the challenge. Blue light requires wide energy band. With blue light-emitting polymers as primary materials, it is possible to produce other colors by a downhill energy transfer process. For instance, a green or red EL emission can be obtained by doping a blue EL host material with a small amount of green or red luminescent material.

SUMMARY OF THE INVENTION

It is an object of the present invention to provide novel highly efficient luminescent materials in an electroluminescent device.

It is another object of the present invention to provide wide energy band gap luminescent materials.

These objects are achieved by providing the following organic materials for an organic electroluminescent device. The organic materials comprise a complex fluorene structure represented by one of the following Formulae (I), (II), or (III):

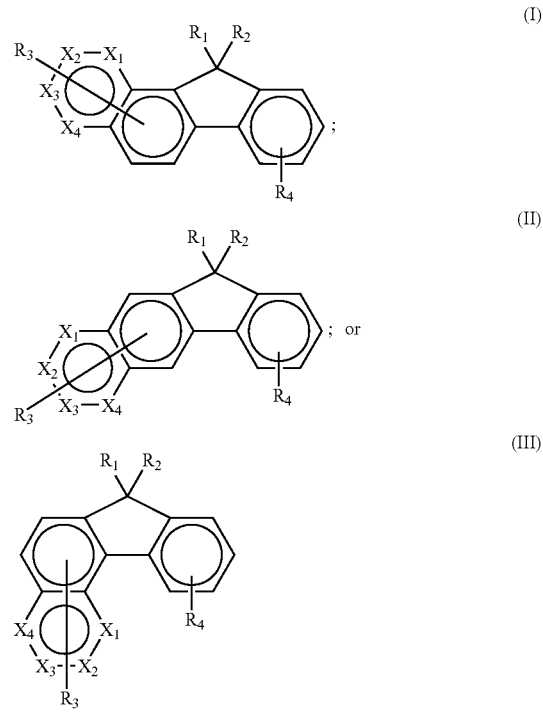

wherein:
$X_1$, $X_2$, $X_3$, and $X_4$ are individually the same or different and include a moiety containing CH or N; $R_1$, $R_2$, $R_3$, and $R_4$ are substituents each being individually hydrogen, or amino, or alkyl, or alkenyl, or alkynyl, or alkoxy of from 1 to 40 carbon atoms; aryl or substituted aryl of from 6 to 60 carbon atoms; or heteroaryl or substituted heteroaryl of from 4 to 60 carbons; or F, Cl, or Br; or a cyano group; or a nitro group; or $R_3$, or $R_4$ or both are groups that form fused aromatic or heteroaromatic rings; or $R_1$ and $R_2$ together form a cyclic ring having 3 to 20 carbon, nitrogen, sulfur or oxygen atoms; or $R_1$ and $R_2$ together form a double bond moiety.

The present invention provides organic luminescent materials with a number of advantages that include excellent solubility and thermal stability, effective color tunability, high efficiency and low driving voltage.

DETAILED DESCRIPTION OF THE INVENTION

Figure 1:
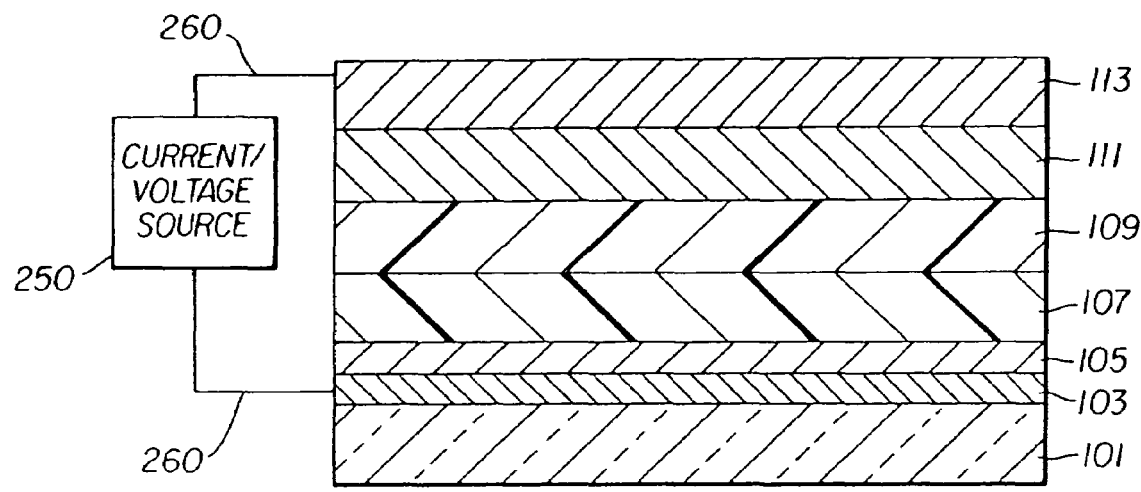
FIG. 1 illustrates in cross-section a basic structure of an EL device.

The present invention provides highly efficient organic light-emitting materials comprising a complex fluorene structure with effective color tunability, excellent solubility and thermal stability, and enhanced electron or hole transport ability. The complex fluorene is represented by Formulae (I), (II), or (III), $X_1$, $X_2$, $X_3$, and $X_4$ are individually the same or different and include a moiety containing CH or N; $R_1$, $R_2$, $R_3$, and $R_4$ are substituents each being individually hydrogen, or amino, or alkyl, or alkenyl, or alkynyl, or alkoxy of from 1 to 40 carbon atoms; aryl or substituted aryl of from 6 to 60 carbon atoms; or heteroaryl or substituted heteroaryl of from 4 to 60 carbons; or F, Cl, or Br; or a cyano group; or a nitro group; or $R_3$, or $R_4$ or both are groups that form fused aromatic or heteroaromatic rings; or $R_1$ and $R_2$ together form a cyclic ring having 3 to 20 carbon, nitrogen, sulfur or oxygen atoms; or $R_1$ and $R_2$ together form a double bond moiety.

For example, $R_1$, $R_2$, $R_3$, and $R_4$ are independently hydrogen, methyl, ethyl, propyl, isopropyl, butyl, isobutyl, t-butyl, pentyl, hexyl, ethylhexyl, heptyl, octyl, nonyl, decyl, dodecyl, hexadecyl, cyclohexyl, cyclopentyl, methoxy, ethoxy, butoxy, hexyloxy, ethylhexyloxy, methoxyethoxyethyl, methoxyethyloxyethoxyethyl, diphenylamino, (4-diphenylamino)phenyl, phenyl, tolyl, nathphyl, xylene, anthracene, thiophene, phenanthrene, phenylmethylene-phenyl, benzyl, phenoxy, pyridyl, thiophenyl; or $R_1$ and $R_2$ together form a cyclic ring having 3 to 20 carbon, nitrogen, sulfur or oxygen atoms such as cyclopentyl, cyclohexyl, tetralonyl, fluorenyl, 2,5-dioxocyclopentyl, 2,5-dithiocyclopentyl, 2,6-dioxocyclohexyl, and 2,6-dithiocyclohexyl; or $R_1$ and $R_2$ together form a double bond moiety such as carbonyl group, substituted or unsubstituted methylene groups. $R_3$, and $R_4$ are groups that form fused aromatic or heteroaromatic rings such as naphthalene, anthracene, perylene, phenanthrene, pyrene, tetracene, pentacene, triphenylene, and benzo[a]pyrene. Preferably, $R_1$, $R_2$, $R_3$, and $R_4$ are hydrogen, t-butyl, hexyl, 2-ethylhexyl, octyl, 3,7-dimethyloctyl, decyl, heptyl, phenyl, 2-ethylhexyloxy, or 4-methoxypheny; diphenylamino, (4-diphenylamino)phenyl, $R_1$ and $R_2$ together form a cyclohexyl, cyclopentyl, fluorenyl, or 2,5-dioxocylopentyl; or $R_1$ and $R_2$ together form carbonyl, methylene, dicyanomethylene, cyclohexylene, and cyclopentylene $R_3$ forms fused aromatic anthracene, or perylene, or pyrene, phenanthrene, or tetracene, and $R_4$ forms a naphthalene or anthracene; or $R_3$, or $R_4$ or both represent one or more than one substituents.

The organic materials comprising the complex fluorene structure are small molecules, oligomers, or polymers, and can be used including two or more thereof. Small molecules include dendrimers and polymers include hyperbranched and ladder architecture.

Small molecules comprising the complex fluorene structure are represented by Formula (IV)

$$(Y_1)y_1\text{-complex fluorene-}(Y_2)y_2 \quad \text{(IV)}$$
$$\text{(I), (II), or (III)}$$

wherein $Y_1$ and $Y_2$ each individually represent a substituted or unsubstituted alkyl, alkenyl, alkynyl, aryl, or heteroaryl or other conjugated groups, and $y_1$ and $y_2$ are integers from 0 to 6, and $Y_1$ and $Y_2$ are the same or different.

Polymers comprising the complex fluorene structure are represented by repeating units of Formula (V) which comprise the complex fluorene structure as part of the polymer main chain and repeating units of Formula (VI) which comprise the complex structure as part of the polymer side chain

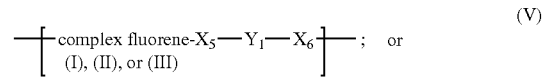

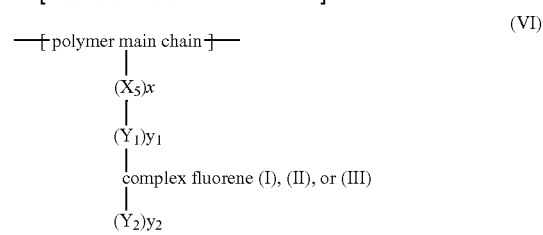

wherein:
$X_5$ and $X_6$ are linking groups, $Y_1$ and $Y_2$ are each individually represented as a substituted or unsubstituted alkyl, alkenyl, alkynyl, aryl, or heteroaryl or other conjugated groups, and x, $y_1$ and $y_2$ are integers from 0 to 6.

Incorporating $Y_1$ and $Y_2$ units into the compounds comprising the complex fluorene structure represented by Formula (IV), (V), and (VI) can further improves solubility, or electron or hole transporting mobility, or finely tune the emission color.

$X_5$ and $X_6$ each individually represent a linking group and include but are not limited to the following groups:

Group I:
$X_5$ and $X_6$ are carbon-carbon bond linking groups:

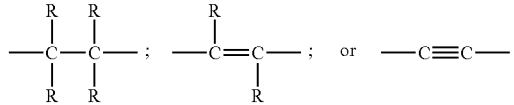

wherein R is hydrogen, alkyl, alkynyl, or alkenyl group containing 1 to 40 carbon atoms; aryl or substituted aryl of containing 6 to 60 carbon atom s; or heteroaryl or substituted heteroaryl containing 4 to 60 carbons; or F, Cl, or Br; or a cyano, or a nitro group;

Group II:

$X_5$ and $X_6$ are ether or thioether linking groups:

—O—; or

—S—;

Group III:

$X_5$ and $X_6$ are ester linking groups:

$$-\overset{O}{\underset{\|}{C}}-O-\ ;\ \text{or}\ -O-\overset{O}{\underset{\|}{C}}-\ ;$$

Group IV:

$X_5$ and $X_6$ are anhydride linking groups:

$$-\overset{O}{\underset{\|}{C}}-O-\overset{O}{\underset{\|}{C}}-\ ;$$

Group V:

$X_5$ and $X_6$ are carbonate linking groups:

$$-O-\overset{O}{\underset{\|}{C}}-O-\ ;$$

Group VI:

$X_5$ and $X_6$ are sulfone or sulfine linking groups:

$$-\overset{O}{\underset{\|}{S}}-\ ;\ \text{or}\ -\overset{O}{\underset{\underset{O}{\|}}{\overset{\|}{S}}}-\ ;$$

Group VII:

$X_5$ and $X_6$ are an amine linking groups:

$$-\overset{R}{\underset{|}{N}}-$$

wherein R is defined as above;

Group VIII:

$X_5$ and $X_6$ are amide linking groups:

$$-\overset{R}{\underset{|}{N}}-\overset{O}{\underset{\|}{C}}-\ ;\ \text{or}\ -\overset{O}{\underset{\|}{C}}-\overset{R}{\underset{|}{N}}-\ ;$$

Group IX:

$X_5$ and $X_6$ are urea linking groups:

$$-\overset{}{\underset{R}{\overset{|}{N}}}-\overset{O}{\underset{\|}{C}}-\overset{}{\underset{R}{\overset{|}{N}}}-\ ;$$

Group IX:

$X_5$ and $X_6$ are aryl or heteroaryl linking groups:

$-(AR)_n-$ wherein Ar is an aryl or substituted aryl group containing 6 to 60 carbon atoms; or heteroaryl or substituted heteroaryl containing 4 to 60 carbons; n is an integer of from 1 to 6;

$X_5$ and $X_6$ can be one or the combination of more than one of the above groups;

$Y_1$ and $Y_2$ represents a substituted or unsubstituted alkyl, alkenyl, alkynyl, aryl, heteroaryl or other conjugated groups, and can be the same or different;

alkyl, alkenyl, and alkynyl groups contain 1 to 40 carbon atoms;

substituted or unsubstituted aryl groups contain 6 to 60 carbon atoms which include phenyl, biphenyl, naphthyl, anthracene, fluorene, phenanthrene, spirophenyl, perylene, or pyrene groups; and substituted or unsubstituted heteroaryl groups contain 4 to 60 carbon atoms which include pyridine, thiophene, pyrrole, bithiophene, furan, benzofuran, benzimidazole, benzoxazole, quinoxaline, phenylquinoline, dipheyloxadizaole, or carbazole.

All the substituents mentioned above include, but are not limited to, alkyl or alkoxy groups containing 1 to 40 carbon atoms, aryl or substituted aryl containing 6 to 60 carbon atoms; or heteroaryl or substituted heteroaryl containing 4 to 60 carbons; or F, Cl, or Br; or a cyano group; or a nitro group.

$Y_1$ and $Y_2$ can be divided into the following groups:

Group I:

$Y_1$ and $Y_2$ are alkyl, alkenyl, or alkynyl groups of Formula (VII):

—W— (VII)

wherein:

W contains 1 to 28 carbon atoms, can also contain O, N, S, F, Cl, or Br, or Si atoms.

The following structures constitute specific examples of Formula (VII)

$-(CH_2)_m-$ wherein:

m is an integer from 1 to 6;

$$-(CH_2)_m-\underset{\underset{(CH_2)_qCH_3}{|}}{\overset{\overset{(CH_2)_qCH_3}{|}}{Si}}-(CH_2)_m-$$

wherein:

q is an integer from 0 to 12;

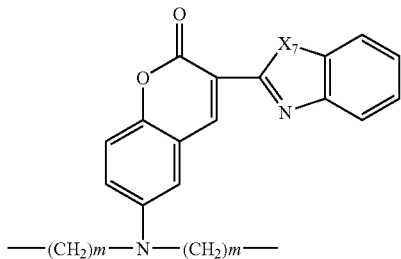

wherein:
  $X_7$ is a C, O, N, or S atom;

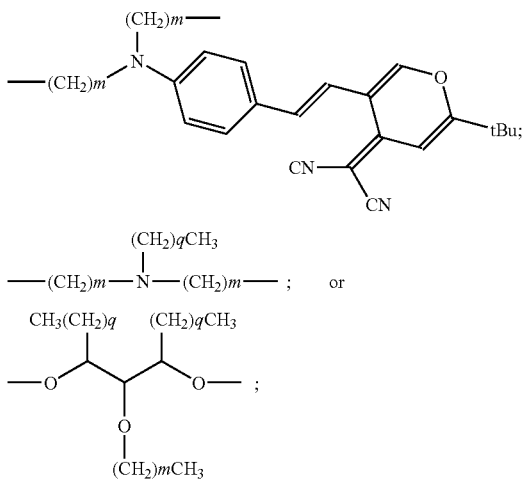

Group II:
  $Y_5$ and $Y_6$ are two aryl or heteroaryl groups connected by a linking group Z of Formula (VIII):

—(Ar₁)-Z-(Ar₂)—    (VIII)

wherein:
  Ar₁ and Ar₂ are substituted or unsubstituted aryl groups containing 6 to 60 carbon atoms, or heteroaryl groups containing 4 to 60 carbons; and
  Z is a divalent linking groups containing 0 to 40 carbon atoms, can contain N, Si, O, Cl, F, Br, or S atoms.

The following structures constitute specific examples of Formula (VIII):

wherein:
  R is defined as above, and can represent more than one such substituent;

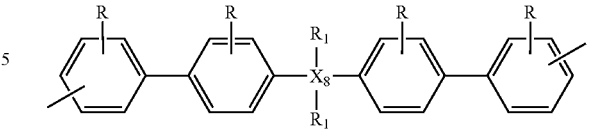

wherein:
  $X_8$ is C or Si;

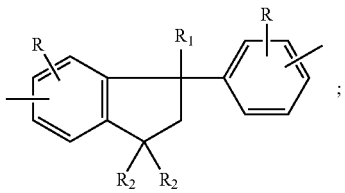

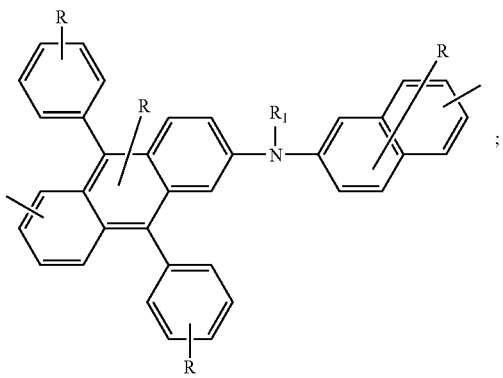

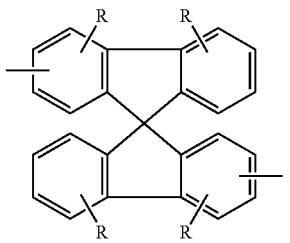

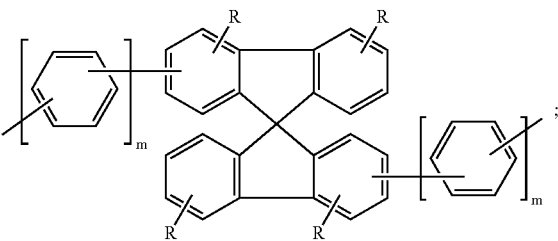

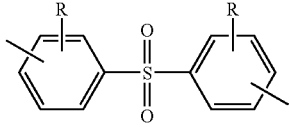

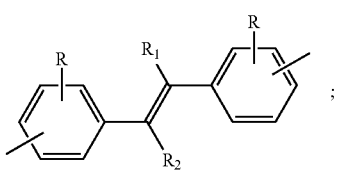

-continued

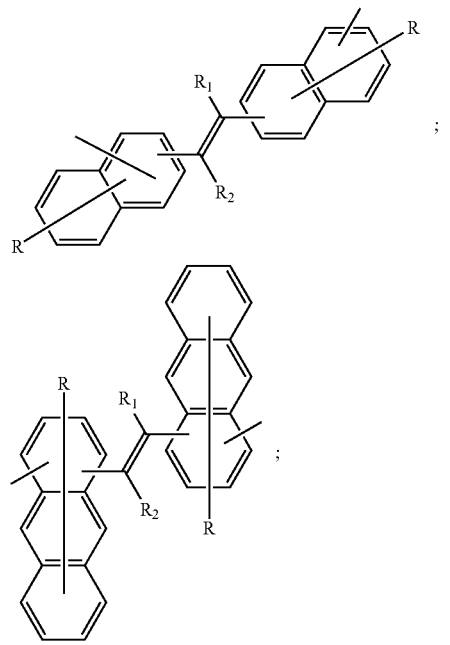

wherein:
p and r are integers from 1 to 4;

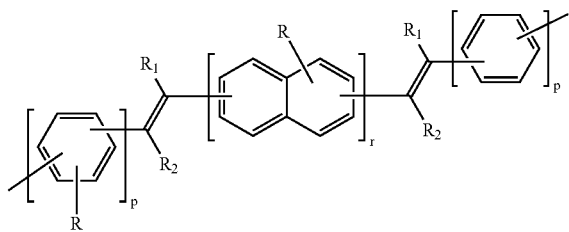

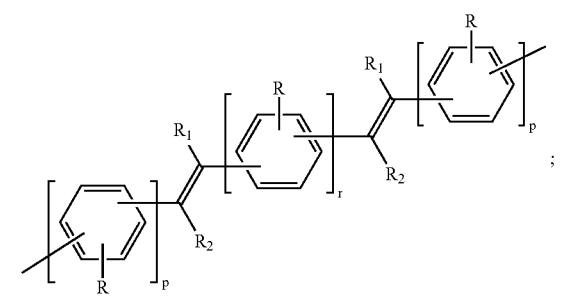

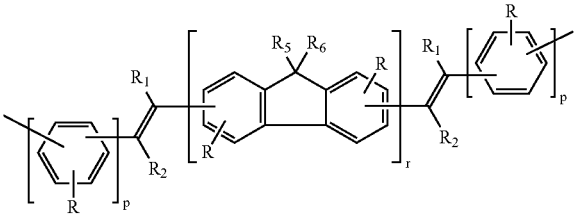

wherein:
$R_5$, and $R_6$ are substituents each being individually hydrogen, or alkyl, or alkenyl, or alkynyl, or alkoxy of from 1 to 40 carbon atoms;

aryl or substituted aryl of from 6 to 60 carbon atoms; or heteroaryl or substituted heteroaryl of from 4 to 60 carbons; or F, Cl, or Br; or a cyano group; or a nitro group; or

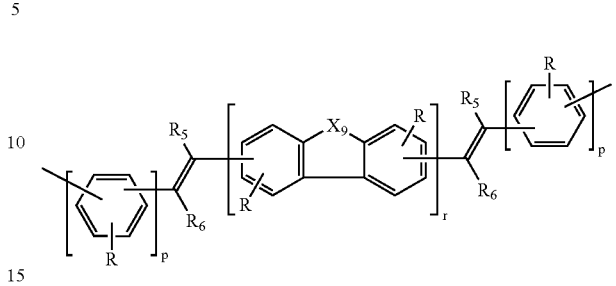

wherein:
$X_9$ is O or S atom, or N—R;

Group III:
$Y_1$ and $Y_2$ are aryl or heteroaryl groups of Formula (IX):

$$—Ar— \qquad (IX)$$

wherein:
Ar is a substituted or unsubstituted aryl group with 6 to 60 carbon atoms, or a substituted or unsubstituted heteroaryl group with 4 to 60 carbon atoms, and at least one or more N, S, or O atoms.

The following structures constitute specific examples of Formula (IX):

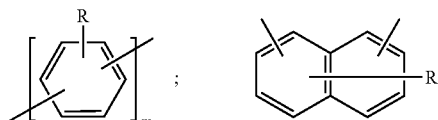

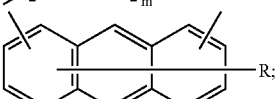

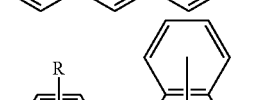

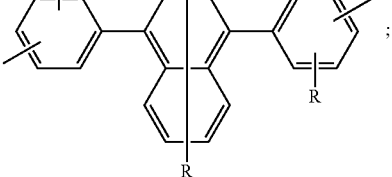

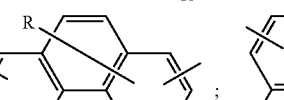

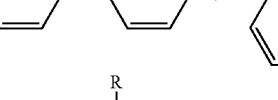

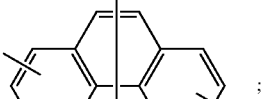

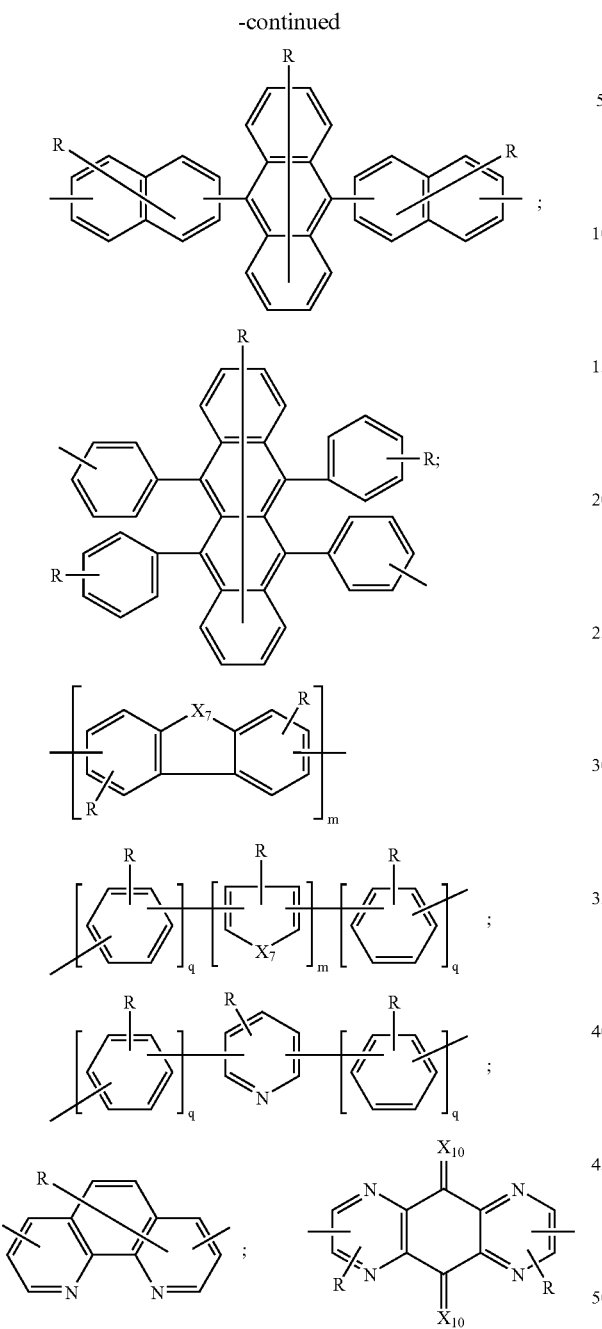
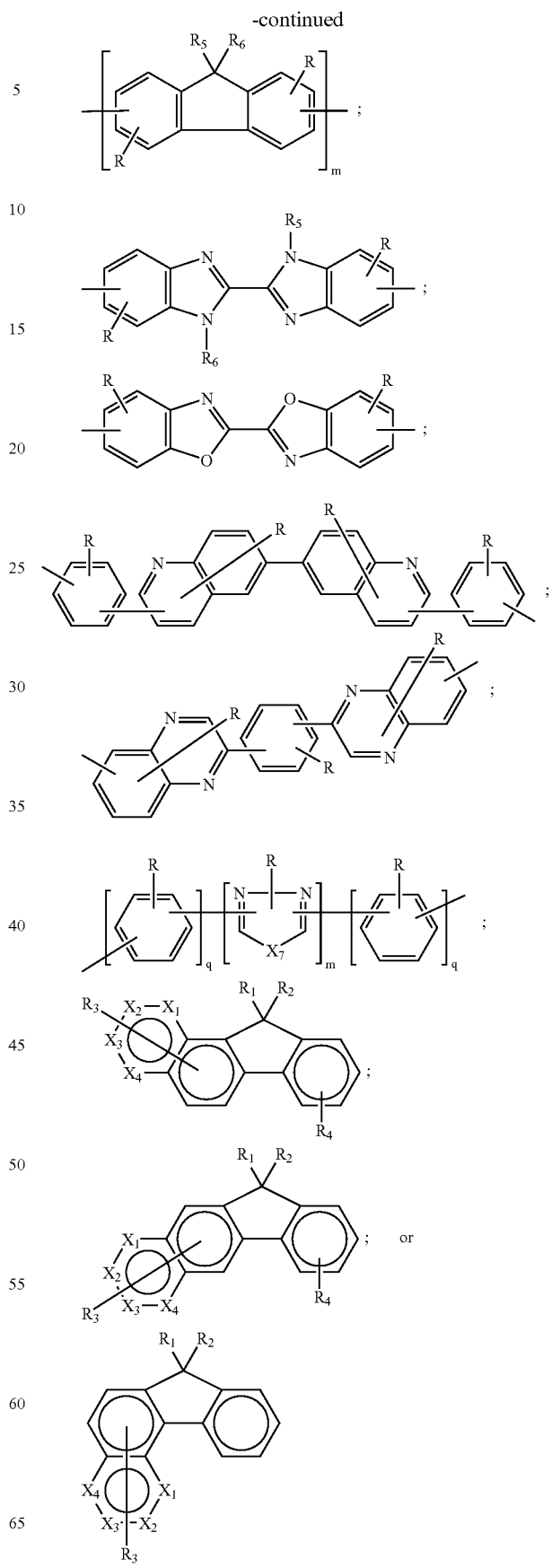
wherein:
 $X_{10}$ is an O atom or two cyano groups;
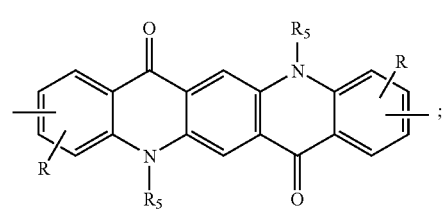

wherein:

Y$_1$ and Y$_2$ can be one or the combination of more than one of the above groups.

The following molecular structures constitute specific examples of preferred compounds satisfying the requirement of this invention:

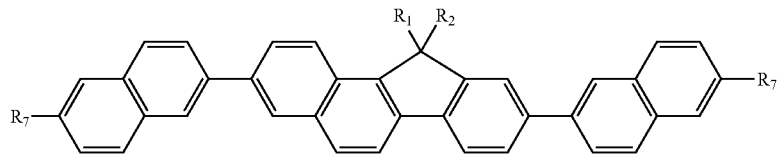

compound 1 R$_1$=R$_2$=n-hexyl, R$_7$=H
compound 2 R$_1$=R$_2$=n-octyl, R$_7$=H
compound 3 R$_1$=R$_2$=2-ethylhexyl, R$_7$=n-hexyl
compound 4 R$_1$=n-hexyl, R$_2$=2-ethylhexyl, R$_7$=H

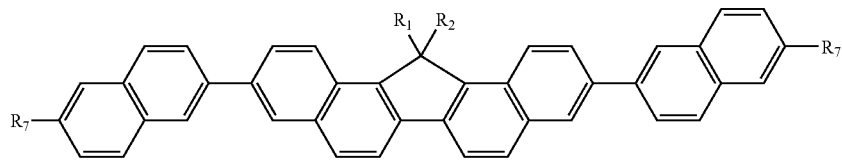

compound 5 R$_1$=R$_2$=n-octyl, R$_7$=hexyl
compound 6 R$_1$=R$_2$=2-ethylhexyl, R$_7$=H
compound 7 R$_1$=n-hexyl, R$_2$=2-ethylhexyl, R$_7$=H

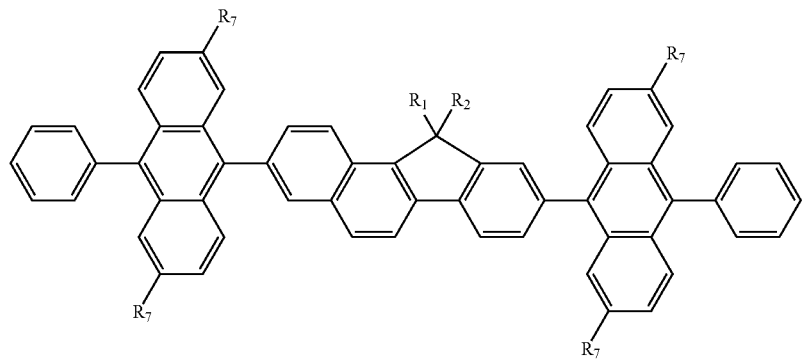

compound 8 R$_1$=n-hexyl, R$_2$=2-ethylhexyl, R$_7$=t-butyl
compound 9 R$_1$=n-hexyl, R$_2$=2-ethylhexyl, R$_7$=2-ethylhexyl
compound 10 R$_1$=n-hexyl, R$_2$=2-ethylhexyl, R$_7$=2-ethylhexyloxy
compound 11 R$_1$=R$_2$=R$_7$=2-ethylhexyl

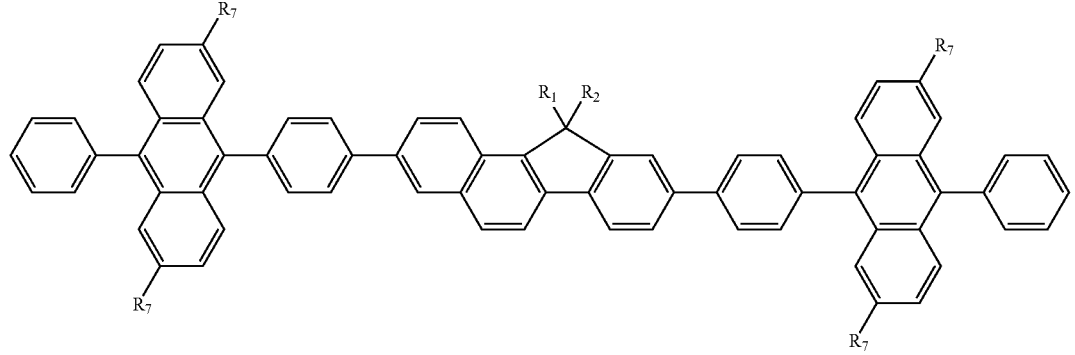

compound 12 R₁=n-hexyl, R₂=2-ethylhexyl, R₇=t-butyl
compound 13 R₁=n-hexyl, R₂=R₇=2-ethylhexyl
compound 14 R₁=n-hexyl, R₂=2-ethylhexyl, R₇=2-ethylhexyloxy
compound 15 R₁=R₂=R₇=2-ethylhexyl
compound 16 R₁=R₂=2-ethylhexyl, R₇=H

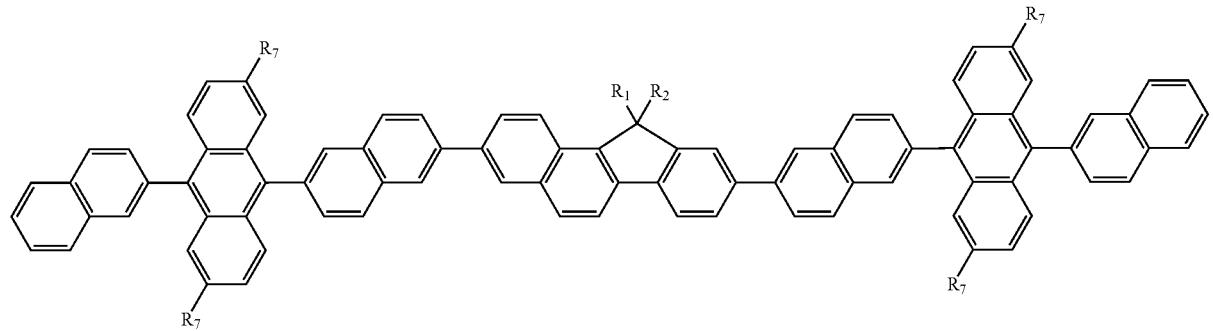

compound 17 R₁=n-hexyl, R₂=2-ethylhexyl, R₇=t-butyl
compound 18 R₁=n-hexyl, R₂=R₇=2-ethylhexyl
compound 19 R₁=n-hexyl, R₂=2-ethylhexyl, R₇=2-ethylhexyloxy
compound 20 R₁=R₂=R₇=2-ethylhexyl
compound 21 R₁=R₂=2-ethylhexyl, R₇=n-octyl

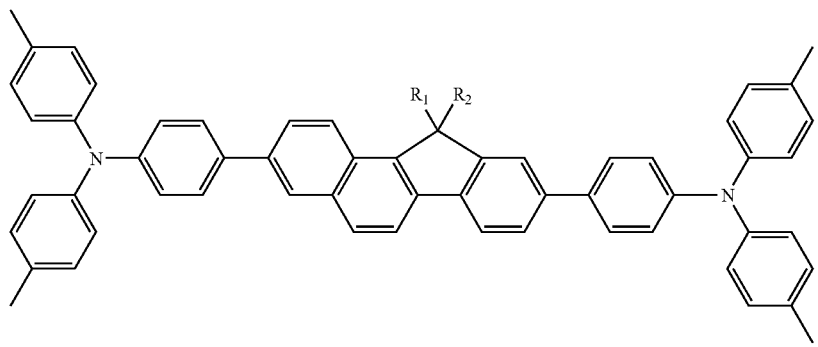

compound 22 R₁=n-hexyl, R₂=2-ethylhexyl
compound 23 R₁=R₂=n-hexyl
compound 24 R₁=R₂=2-ethylhexyl
compound 25 R₁=R₂=phenyl
compound 26 R₁=R₂=4-(bis(4-methylphenyl)amino)phenyl

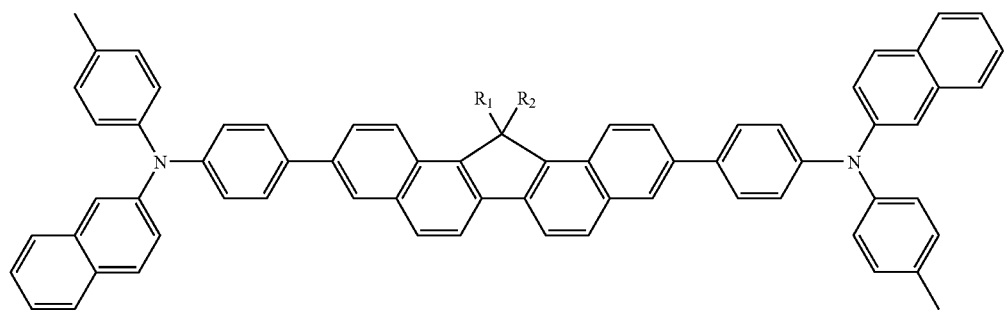

compound 27 R₁=R₂=2-ethylhexyl
compound 28 R₁=R₂=4-(bis(4-methylphenyl)amino)phenyl
compound 29 R₁=2-ethylhexyl, R₂=n-octyl

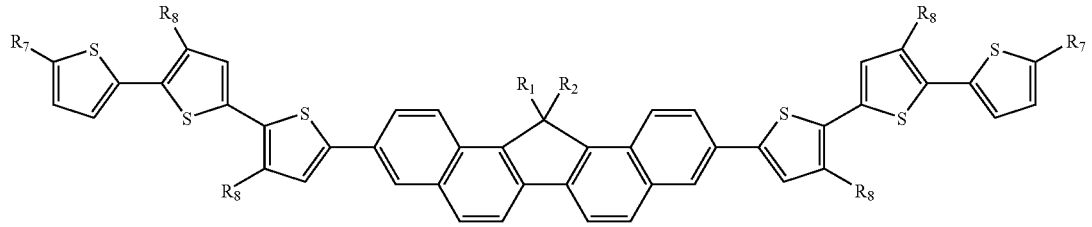

compound 30 $R_1=R_2=R_7=R_8$=2-ethylhexyl
compound 31 $R_1=R_2=R_7=R_8$=n-hexyl
compound 32 $R_1=R_7$=n-hexyl, $R_2$=2-ethylhexyl, $R_8$=H

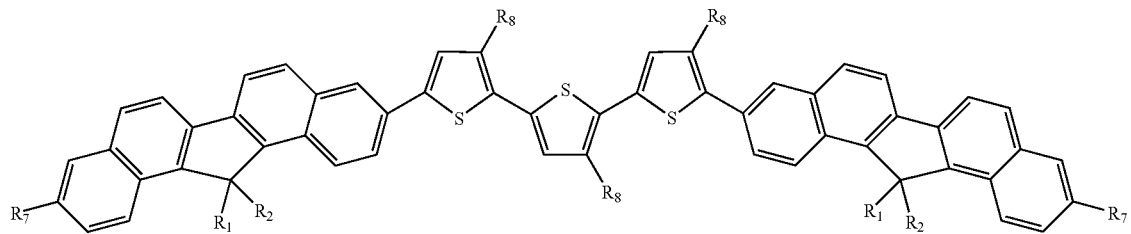

compound 33 $R_1=R_2=R_7=R_8$=2-ethylhexyl
compound 34 $R_1=R_2=R_7=R_8$=n-hexyl
compound 35 $R_1=R_7$=n-hexyl, $R_2$=2-ethylhexyl, $R_8$=H
compound 36 $R_1=R_2=R_7$=4-(bis(4-methylphenyl)amino)phenyl, $R_8$=n-hexyl compound 37 $R_1$=n-hexyl, $R_2$=2-ethylhexyl, $R_7$=t-butyl compound 38 $R_1$=n-hexyl, $R_2=R_7$=2-ethylhexyl compound 39 $R_1$=n-hexyl, $R_2$=2-ethylhexyl, $R_7$=2-ethylhexyloxy compound 40 $R_1=R_2$=2-ethylhexyl, $R_7$=4-(bis(4-methylphenyl)amino)phenyl compound 41 $R_1$=H, $R_2$=4-n-decylphenyl, $R_7$=4-(bis(4-methylphenyl)-amino)phenyl

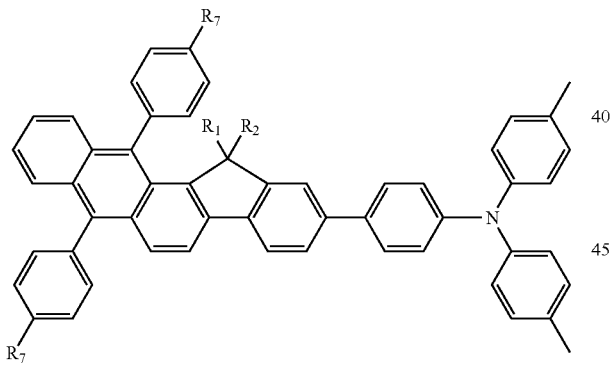

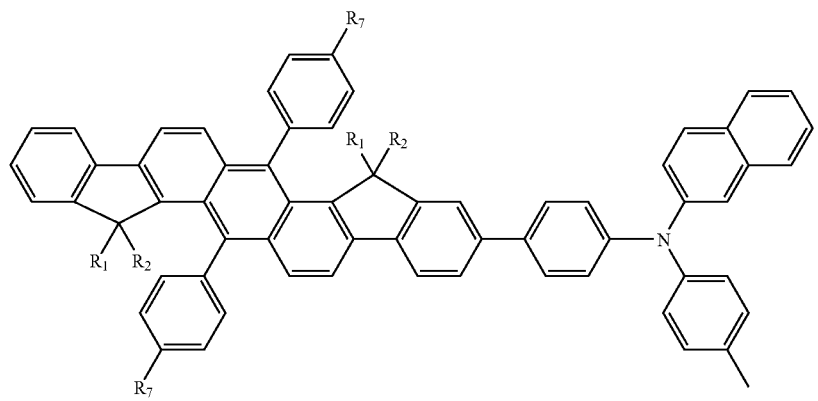

compound 42 R$_1$=n-hexyl, R$_2$=R$_7$=2-ethylhexyl
compound 43 R$_1$=n-hexyl, R$_2$=2-ethylhexyl, R$_7$=2-ethylhexyloxy
compound 44 R$_1$=H, R$_2$=4-n-decylphenyl, R$_7$=4-(bis(4-methylphenyl)-amino)phenyl
compound 44 R$_1$=H, R$_2$=4-n-decylphenyl, R$_7$=2-ethylhexyloxy

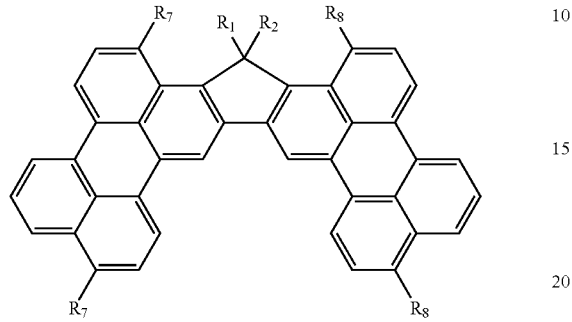

compound 45 R$_1$=R$_3$=n-hexyl, R$_2$=R$_8$=2-ethylhexyl
compound 46 R$_1$=n-hexyl, R$_2$=2-ethylhexyl, R$_7$=2-ethylhexyloxy, R$_8$=diphenylamino
compound 47 R$_1$=H, R$_2$=4-n-decylphenyl, R$_7$=R$_8$=4-(bis(4-methylphenyl)-amino)phenyl
compound 48 R$_1$=H, R$_2$=4-n-decylphenyl, R$_7$=2-ethylhexyloxy, R$_8$=4-(bis(4-methylphenyl)amino)phenyl

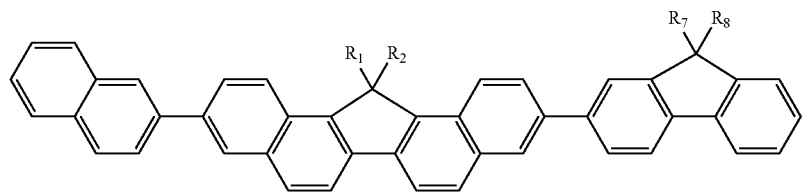

compound 49 R$_1$=R$_2$=n-hexyl, R$_7$=R$_8$=2-ethylhexyl
compound 50 R$_1$=R$_7$=4-(bis(4-methylphenyl)amino)phenyl, R$_2$=R$_8$=H
compound 51 R$_1$=R$_2$=R$_7$=R$_8$=4-n-decylphenyl

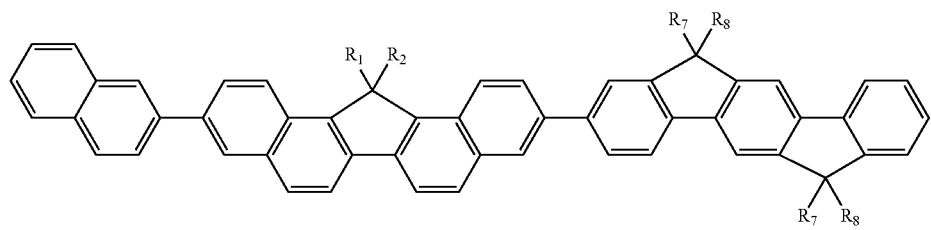

compound 52 R$_1$=R$_2$=n-hexyl, R$_7$=R$_8$=2-ethylhexyl
compound 53 R$_1$=R$_7$=4-(bis(4-methylphenyl)amino)phenyl, R$_2$=R$_8$=H
compound 54 R$_1$=R$_2$=R$_7$=R$_8$=4-n-decylphenyl
compound 55 R$_1$=R$_2$=R$_7$=R$_8$=n-octyl

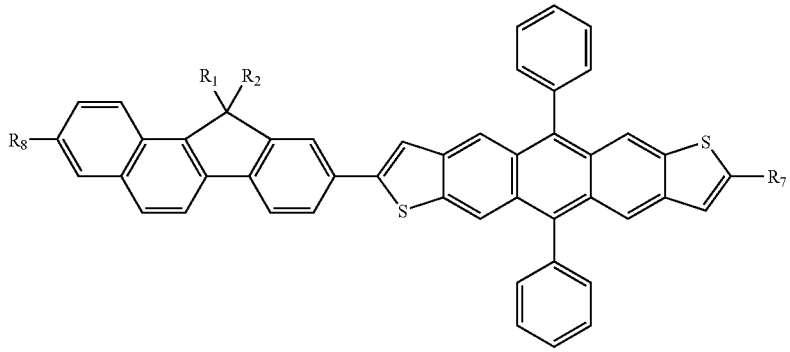

compound 56 R₁=R₂=n-hexyl, R₇=R₈=2-ethylhexyl
compound 57 R₁=R₂=4-(bis(4-methylphenyl)amino)phenyl, R₇=R₈=H
compound 58 R₁=R₂=R₇=R₈=4-n-decylphenyl

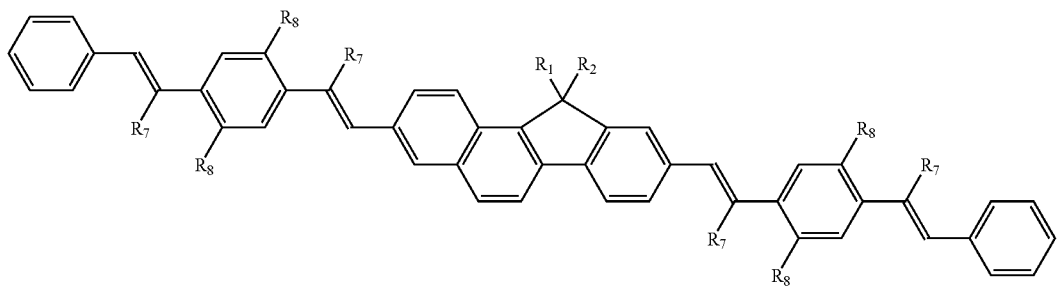

compound 59 R₁=R₂=n-hexyl, R₇=H, R₈=2-ethylhexyl
compound 60 R₁=R₂=4-(bis(4-methylphenyl)amino)phenyl, R₇=H, R₈=n-hexyloxy
compound 61 R₁=R₂=R₈=4-n-decylphenyl, R₇=CN

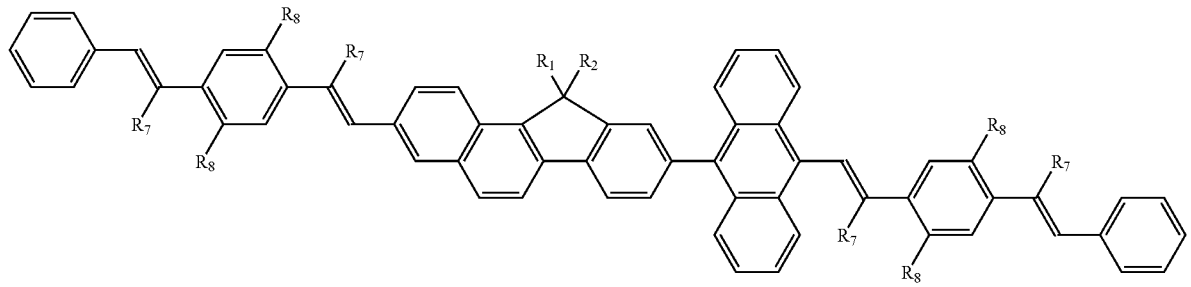

compound 62 R₁=R₂=n-hexyl, R₇=H, R₈=2-ethylhexyl
compound 63 R₁=R₂=R₈=4-(bis(4-methylphenyl)amino)phenyl, R₇=H
compound 64 R₁=R₂=4-n-decylphenyl, R₇=CN, R₈=n-hexyloxy

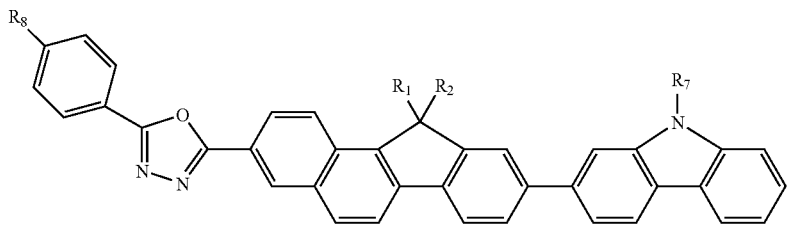

compound 65 R$_1$=R$_2$=n-hexyl, R$_7$=2-ethylhexyl, R$_8$=t-butyl compound 66 R$_1$=R$_2$=4-(bis(4-methylphenyl)amino)phenyl, R$_7$=4-t-butylphenyl, R$_8$=t-butyl compound 67 R$_1$=hexyl, R$_2$=4-n-decylphenyl, R$_7$=2-ethylhexyl, R$_8$=phenyl compound 71 R$_1$=R$_7$=n-hexyl, R$_2$=R$_8$=2-ethylhexyl compound 72 R$_1$=n-hexyl, R$_2$=2-ethylhexyl, R$_7$=2-ethylhexyloxy, R$_8$=diphenylamino compound 73 R$_1$=H, R$_2$=4-n-decylphenyl, R$_7$=R$_8$=4-(bis(4-methylphenyl)-amino)phenyl

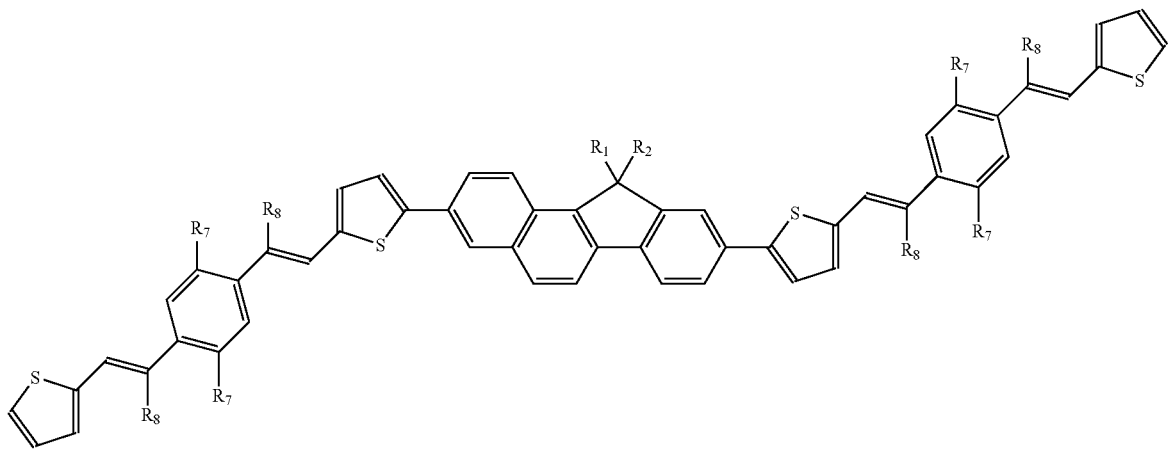

compound 68 R$_1$=R$_2$=n-hexyl, R$_7$=2-ethylhexyl, R$_8$=CN compound 69 R$_1$=R$_2$=4-(bis(4-methylphenyl)amino)phenyl, R$_7$=phenyl, R$_8$=H compound 70 R$_1$=hexyl, R$_2$=4-n-decylphenyl, R$_7$=2-ethylhexyloxy, R$_8$=phenyl compound 74 R$_1$=H, R$_2$=R$_8$=4-n-decylphenyl, R$_7$=2-ethylhexyloxy

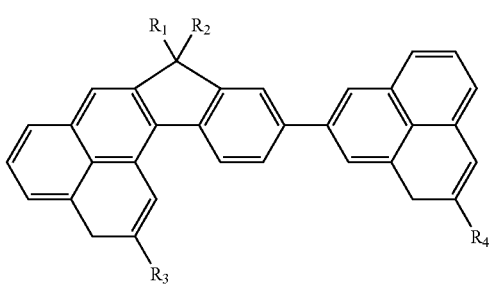

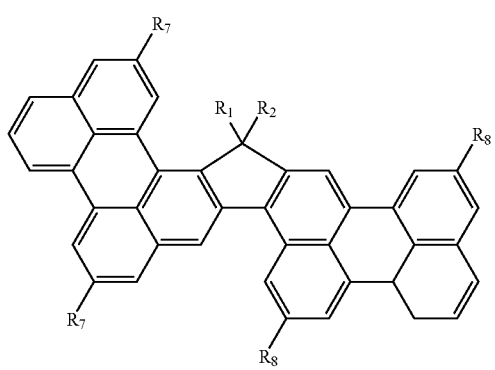

compound 71 R$_1$=R$_3$=n-hexyl, R$_2$=R$_4$=2-ethylhexyl compound 72 R$_1$=n-hexyl, R$_2$=2-ethylhexyl, R$_3$=R$_4$=2-ethylhexyloxy compound 73 R$_1$=R$_2$=4-(bis(4-methylphenyl)amino)phenyl, R$_3$=R$_4$=4-(t-butylphenyl)

compound 74 R$_1$=H, R$_2$=4-n-decylphenyl, R$_3$=2-ethylhexyloxy, R$_4$=2-ethylhexyl

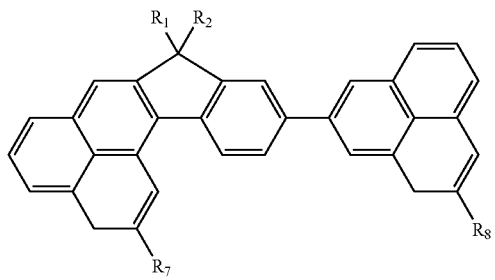

compound 75 $R_1=R_7$=n-hexyl, $R_2=R_8$=2-ethylhexyl
compound 76 $R_1=R_2=R_7=R_8$=2-ethylhexyl
compound 77 $R_1=R_2$=4-(bis(4-methylphenyl)amino)phenyl, $R_7=R_8$=H
compound 78 $R_1$=H, $R_2$=4-n-decylphenyl, $R_7=R_8$=2-ethylhexyloxy

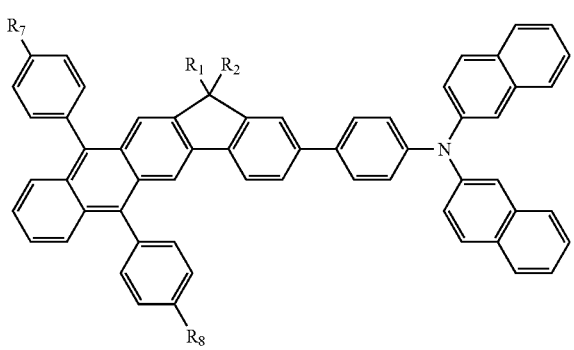

compound 79 $R_1=R_7$=n-hexyl, $R_2=R_8$=2-ethylhexyl
compound 80 $R_1=R_2$=2-ethylhexyl, $R_7=R_8$=2-ethylhexyloxy
compound 81 $R_1=R_2$=4-(bis(4-methylphenyl)amino)phenyl, $R_7=R_8$=t-butyl

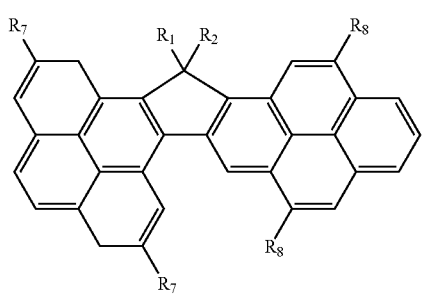

compound 82 $R_1=R_2$=4-(bis(4-methylphenyl)amino)phenyl, $R_7=R_8$=t-butyl
compound 83 $R_1$=H, $R_2$=4-octylphenyl, $R_7=R_8$=2-ethylhexyl
compound 84 $R_1=R_2$=2-ethylhexyl, $R_7$=2-ethylhexyloxy, $R_8$=3,7-dimethyloctyl

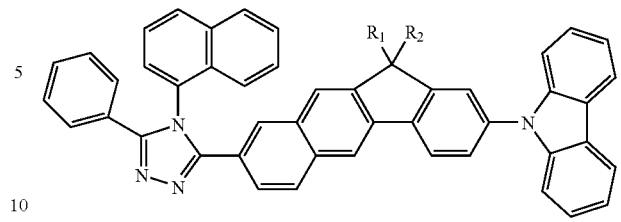

compound 85 $R_1=R_2$=2-ethylhexyl
compound 86 $R_1$=3,7-dimethyloctyl, $R_2$=4-octylphenyl
compound 87 $R_1=R_2$=4-(bis(4-methylphenyl)amino)phenyl

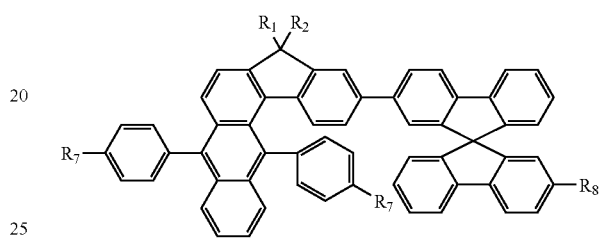

compound 88 $R_1=R_2$=4-(bis(4-methylphenyl)amino)phenyl, $R_7=R_8$=n-hexyl
compound 89 $R_1$=H, $R_2$=4-octylphenyl, $R_7=R_8$=2-ethylhexyloxy
compound 90 $R_1=R_2$=2-ethylhexyl, $R_7$=4-t-butylphenyl, $R_8$=3,7-dimethyloctyl

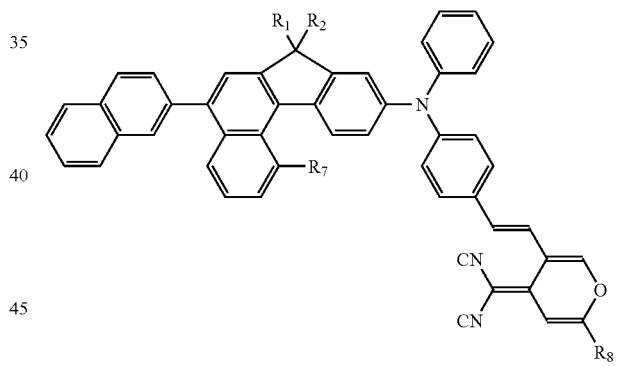

compound 91 $R_1=R_2$=4-(bis(4-methylphenyl)amino)phenyl, $R_7$=n-hexyl, $R_8$=t-butyl
compound 92 $R_1$=H, $R_2$=4-octylphenyl, $R_7=R_8$=2-ethylhexyl
compound 93 $R_1=R_2$=2-ethylhexyl, $R_7$=3,7-dimethyloctyloxy, $R_8$=n-hexyl

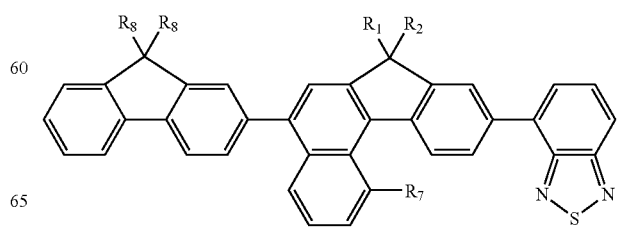

compound 94 R₁=R₂=4-(bis(4-methylphenyl)amino)phenyl, R₇=n-hexyl, R₈=phenyl compound 95 R₁=R₂=2-ethylhexyl, R₇=3,7-dimethyloctyloxy, R₈=n-hexyl compound 96 R₁=R₂=2-ethylhexyl, R₇=3,7-dimethyloctyloxy, R₈=n-hexyl

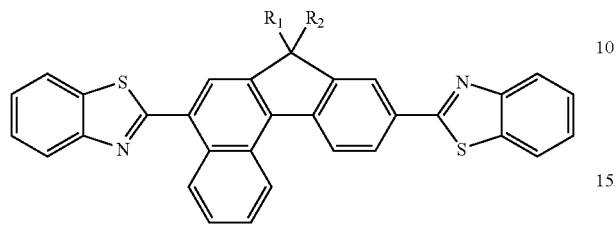

compound 97 R₁=R₂=4-(bis(4-methylphenyl)amino)phenyl compound 98 R₁=ethyl =R₂

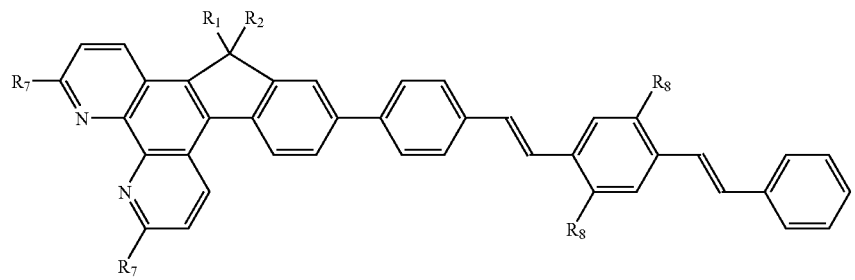

compound 99 R₁=R₂=R₇=R₈=2-ethylhexyl compound 100 R₁=H, R₂=R₇=4-octylphenyl, R₈=2-ethylhexyloxy compound 101 R₁=R₂=2-ethylhexyl, R₇=t-butyl, R₈=diphenylamino compound 102 R₁=R₂=4-(bis(4-methylphenyl)amino)phenyl, R₇=H, R₈=phenyl

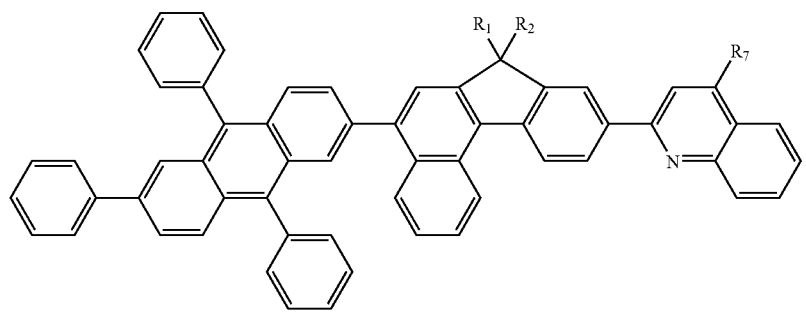

compound 103 R₁=R₂=2-ethylhexyl, R₇=dimethylamino compound 104 R₁=n-hexyl, R₂=4-octylphenyl, R₇=t-butyl compound 105 R₁=R₂=4-(bis(4-methylphenyl)amino)phenyl, R₇=H

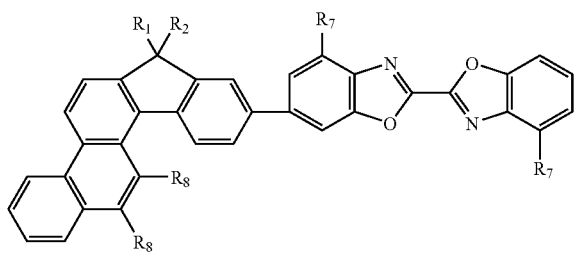

compound 106 R₁=R₂=2-ethylhexyl, R₇=R₈=phenyl
compound 107 R₁=H, R₂=R₇=4-octylphenyl, R₈=2-ethylhexyloxy
compound 108 R₁=R₂=n-octyl, R₇=diphenylamino, R₈=t-butyl
compound 109 R₁=R₂=4-(bis(4-methylphenyl)amino)phenyl, R₇=t-butyl, R₈=phenyl

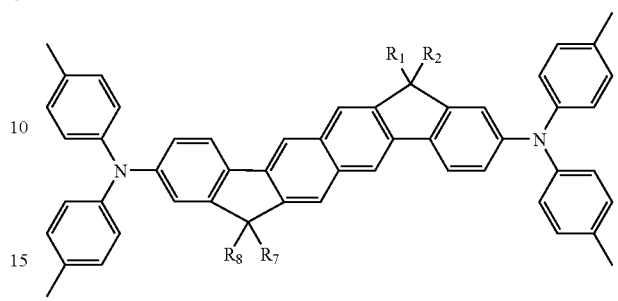

compound 116 R₁=R₂=n-octyl, R₇=(4-diphenylamino)phenyl, R₈=2-ethylhexyl
compound 117 R₁=R₂=4-(bis(4-methylphenyl)amino)phenyl, R₇=n-decyl, R₈=3,7-dimethyloctyl compound 118 R₁=R₂=R₇=R₈=2-ethylhexyl
compound 119 R₁=R₇=n-hexyl, R₂=R₈=4-octylphenyl
compound 120 R₁=R₂=n-octyl, R₇=(4-diphenylamino)phenyl, R₈=2-ethylhexyl

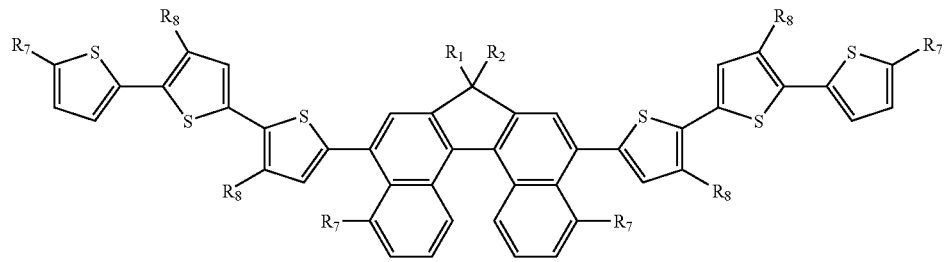

compound 110 R₁=R₂=R₇=R₈=2-ethylhexyl
compound 111 R₁=R₂=R₈=n-hexyl, R₇=phenyl
compound 112 R₁=R₇=n-hexyl, R₂=(4-diphenylamino)phenyl, R₈=2-ethylhexyl
compound 113 R₁=H, R₂=4-decylphenyl, R₇=n-hexyl, R₈=3,7-dimethyloctyl

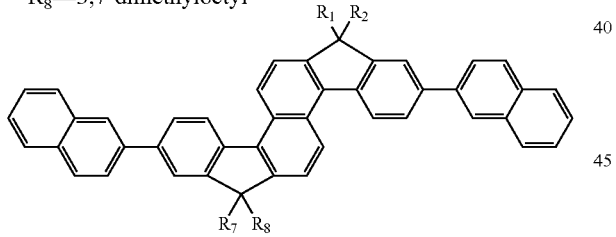

compound 114 R₁=R₂=2-ethylhexyl, R₇=R₈=phenyl
compound 115 R₁=R₇=H, R₂=R₈=4-octylphenyl

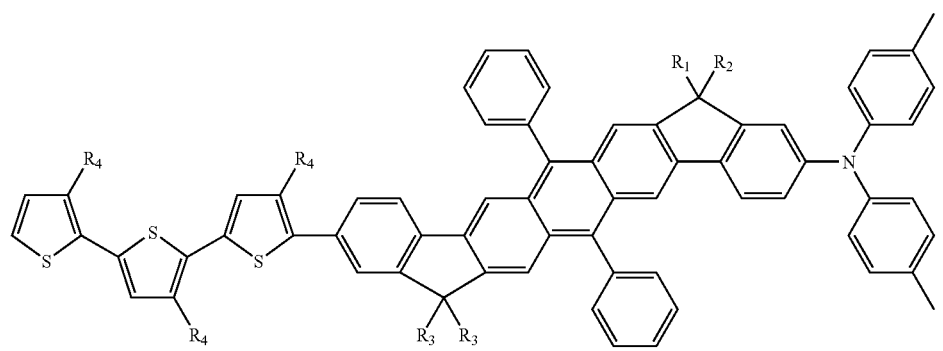

compound 121 R$_1$=R$_2$=R$_7$=2-ethylhexyl, R$_8$=4-hexylphenyl compound 122 R$_1$=H, R$_2$=R$_7$=3,7-dimethyloctyl, R$_8$=2-ethylhexyl compound 123 R$_1$=R$_7$=(4-diphenylamino)phenyl, R$_2$=n-octyl, R$_8$=n-hexyl compound 124 R$_1$=R$_2$=4-(bis(4-methylphenyl)amino)phenyl, R$_7$=n-decyl, R$_8$=H

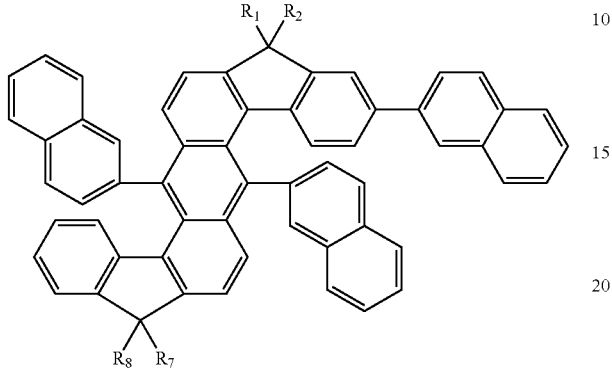

compound 125 R$_1$=R$_2$=R$_7$=R$_8$=2-ethylhexyl compound 126 R$_1$=H, R$_2$=R$_7$=3,7-dimethyloctyl, R$_8$=(4-diphenylamino)-phenyl compound 127 R$_1$=R$_7$=4-(bis(4-methylphenyl)amino)phenyl, R$_2$=R$_8$=n-decyl

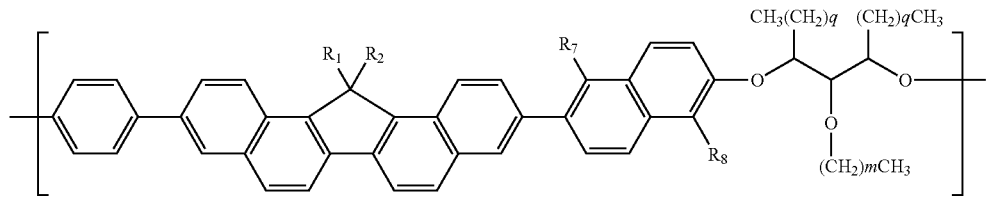

compound 128 R$_1$=R$_2$=R$_7$=R$_8$=2-ethylhexyl, m=10, q=6 compound 129 R$_1$=H, R$_2$=4-decylphenyl, R$_7$=R$_8$=3,7-dimethyloctyl, m=2, q=5 compound 130 R$_1$=R$_7$=4-(bis(4-methylphenyl)amino)phenyl, R$_2$=R$_8$=n-decyl, m=q=1

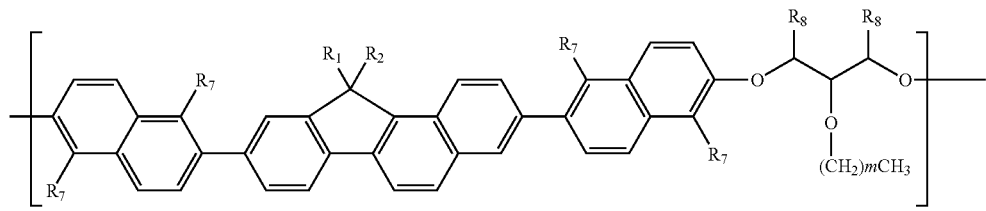

compound 131 R$_1$=R$_2$=2-ethylhexyl, R$_7$=n-hexyloxy, R$_8$=ethyl, m=10 compound 132 R$_1$=R$_2$=4-decylphenyl, R$_7$=H, R$_8$=n-hexyl, m=1 compound 133 R$_1$=R$_2$=n-hexyl, R$_7$=R$_8$=H, m=11 compound 134 R$_1$=R$_2$=4-(bis(4-methylphenyl)amino)phenyl, R$_3$=diphenylamino, R$_4$=H, m=17

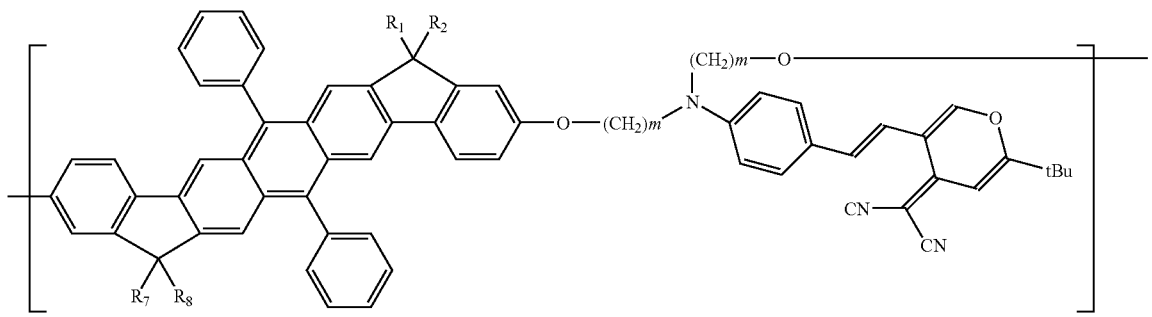

compound 135 R₁=R₂=R₇=R₈=2-ethylhexyl, m=3 compound 136 R₁=H, R₂=R₇=3,7-dimethyloctyl, R₈= (4-diphenylamino)-phenyl, m=2 compound 137 R₁=R₇=4-(bis(4-methylphenyl)amino)phenyl, R₂=R₈=n-decyl, m=3

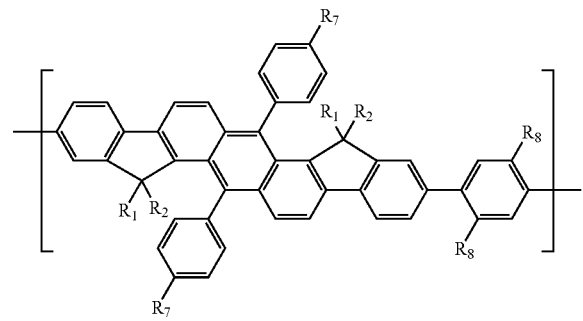

compound 137 R₁=R₂=n-hexyl, R₇=R₈=2-ethylhexyl compound 138 R₁=H, R₂=R₇=3,7-dimethyloctyl, R₈= (4-diphenylamino)-phenyl compound 139 R₁=4-(bis(4-methylphenyl)amino)phenyl, R₂=n-decyl, R₇t-butyl, R₈=n-hexyloxy

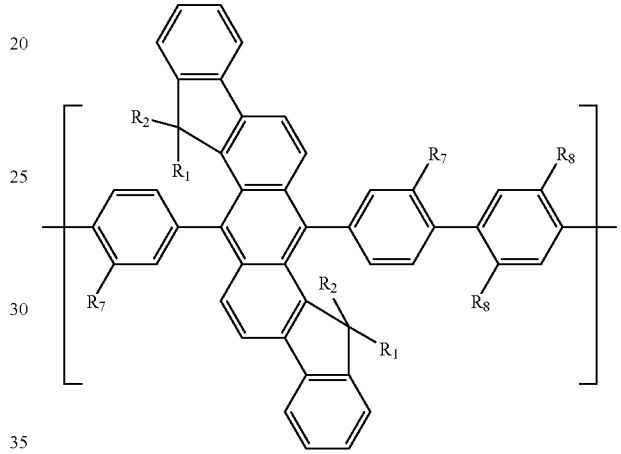

compound 140 R₁=R₂=n-hexyl, R₇=R₈=2-ethylhexyl compound 141 R₁=H, R₂=R₇=3,7-dimethyloctyl, R₈= (4-diphenylamino)-phenyl compound 142 R₁=4-(bis(4-methylphenyl)amino)phenyl, R₂=n-decyl, R₇=t-butyl, R₈=n-hexyloxy compound 143 R₁=4-(N-carbazole)phenyl, R₂=n-decyl, R₇=2-ethylhexyloxy, R₈=n-hexyl compound 144 R₁=4-(n-decyl)phenyl, R₂=R₇=R₈=H

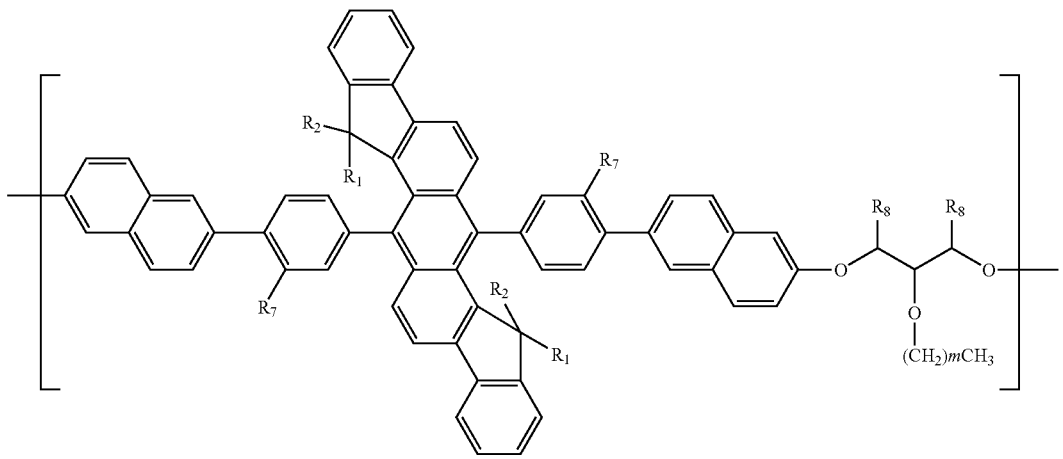

compound 145 R₁=R₂=2-ethylhexyl, R₇=n-hexyloxy, R₈=ethyl, m=10
compound 146 R₁=R₂=4-decylphenyl, R₇=H, R₈=n-hexyl, m=1
compound 147 R₁=R₇=R₈=H, R₂=4-decylphenyl, m=11
compound 148 R₁=R₂=4-(bis(4-methylphenyl)amino)phenyl, R₇=diphenyl-amino, R₈=H, m=17

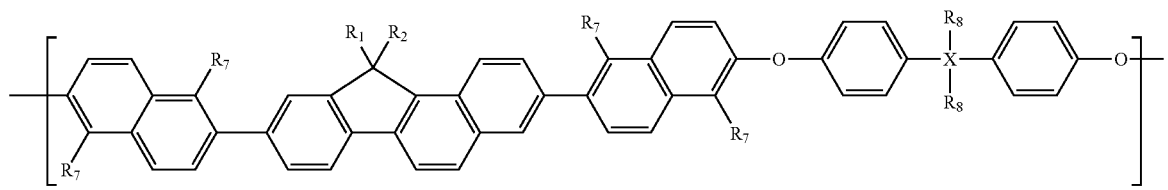

compound 149 R₁=R₂=2-ethylhexyl, R₇=n-hexyloxy, R₈=ethyl, X=C
compound 150 R₁=R₂=2-ethylhexyl, R₇=n-hexyl, R₈=CF₃, X=C
compound 151 R₁=R₇=4-decylphenyl, R₂=H, R₈=n-butyl, X=Si
compound 152 R₁=H, R₂=4-(bis(4-methylphenyl)amino)phenyl, R₇=diphenylamino, R₈=n-hexyl, X=Si

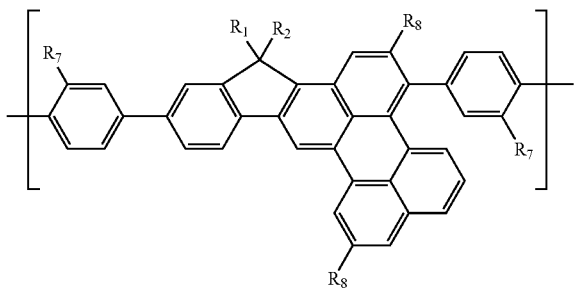

compound 153 R₁=R₂=n-hexyl, R₇=R₈=2-ethylhexyl
compound 154 R₁=H, R₂=R₇=3,7-dimethyloctyl, R₈=(4-diphenylamino)-phenyl
compound 155 R₁=4-(bis(4-methylphenyl)amino)phenyl, R₂=n-decyl, R₇=t-butyl, R₈=n-hexyloxy
compound 156 R₁=4-(N-carbazole)phenyl, R₂=n-decyl, R₇=2-ethylhexyloxy, R₈=n-hexyl

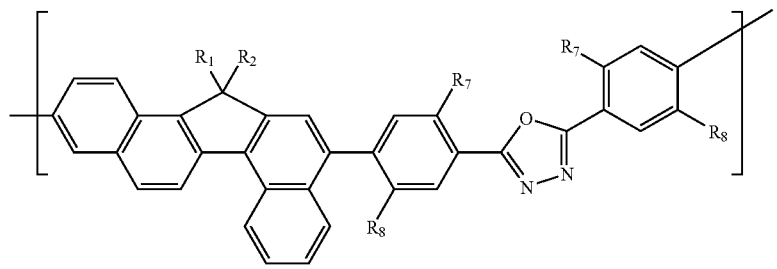

compound 157 R₁=R₂=n-hexyl, R₇=R₈=2-ethylhexyloxy
compound 158 R₁=H, R₂=R₇=3,7-dimethyloctyl, R₈=(4-diphenylamino)-phenyl
compound 159 R₁=4-(bis(4-methylphenyl)amino)phenyl, R₂=n-decyl, R₇=t-butyl, R₈=n-hexyloxy

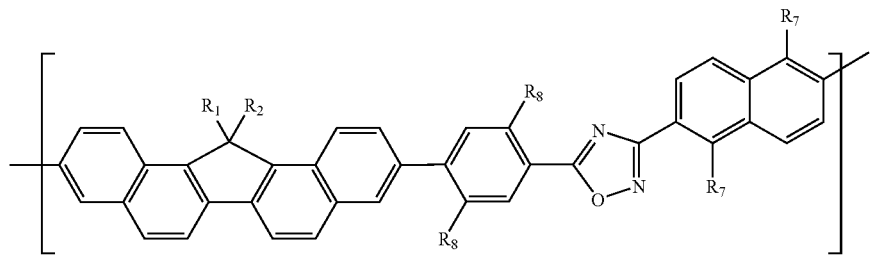

compound 160 R₁=R₂=n-hexyl, R₇=R₈=2-ethylhexyloxy
compound 161 R₁=H, R₂=R₇=3,7-dimethyloctyl, R₈=(4-diphenylamino)-phenyl
compound 162 R₁=4-(bis(4-methylphenyl)amino)phenyl, R₂=n-decyl, R₇=t-butyl, R₈=n-hexyloxy

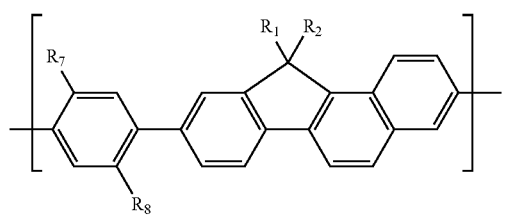

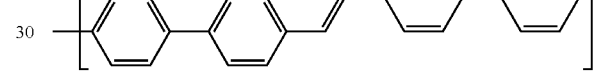

compound 163 R₁=R₂=n-hexyl, R₇=R₈=2-ethylhexyloxy
compound 164 R₁=n-hexyl, R₂=R₇=3,7-dimethyloctyl, R₈=(4-diphenyl-amino)phenyl
compound 165 R₁=R₂=n-hexyl, R₇=R₈=H
compound 166 R₁=4-(bis(4-methylphenyl)amino)phenyl, R₂=n-decyl, R₇=t-butyl, R₈=n-hexyloxy
compound 167 R₁=R₂=n-hexyl, R₇=R₈=n-octyl
compound 168 R₁=R₂=n-hexyl, R₇=R₈=n-hexyloxy compound 172 R₁=R₂=n-hexyl, R₇=R₈=4-octylphenyl
compound 173 R₁=n-hexyl, R₂=R₇=3,7-dimethyloctyl, R₈=(4-diphenyl-amino)phenyl
compound 174 R₁=R₂=R₇=R₈=n-hexyl
compound 175 R₁=4-(bis(4-methylphenyl)amino)phenyl, R₂=n-decyl, R₇=R₈=n-octyl

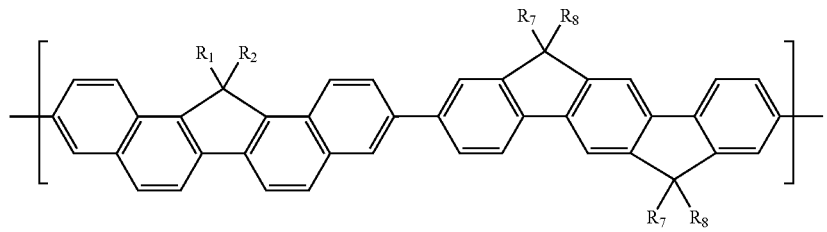

compound 169 R₁=R₂=n-hexyl, R₇=R₈=2-ethylhexyl
compound 170 R₁=H, R₂=R₇=3,7-dimethyloctyl, R₈=(4-diphenylamino)-phenyl
compound 171 R₁=4-(bis(4-methylphenyl)amino)phenyl, R₂=n-decyl, R₇=R₈=n-hexyl

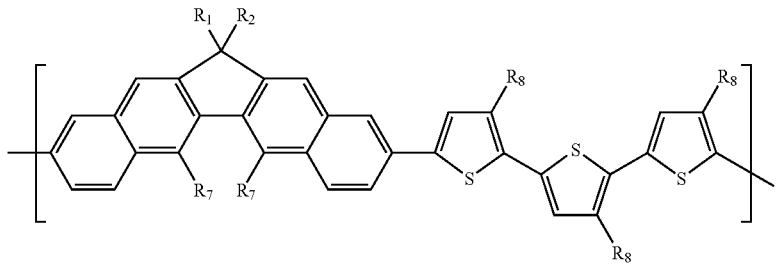

compound 176 R₁=R₂=n-hexyl, R₇=n-hexyloxy, R₈=2-ethylhexyl compound 177 R₁=R₇=n-hexyl, R₂=3,7-dimethyloctyl, R₈=(4-diphenyl-amino)phenyl compound 178 R₁=R₂=R₇=R₈=n-hexyl compound 179 R₁=4-(bis(4-methylphenyl)amino)phenyl, R₂=n-decyl, R₇=methyl, R₈=n-hexyl

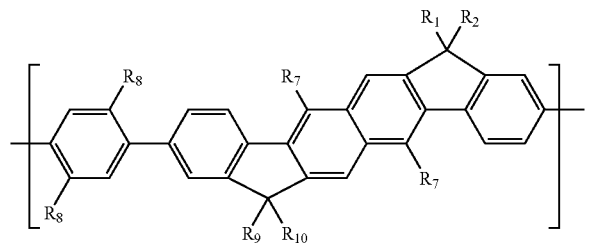

compound 180 R₁=R₂=R₉=R₁₀=n-hexyl, R₇=R₈=2-ethylhexyloxy compound 181 R₁=R₉=n-hexyl, R₂=R₇=R₁₀=3,7-dimethyloctyl, R₈=(4-diphenylamino)phenyl compound 182 R₁=R₂=R₉=R₁₀=n-hexyl, R₇=n-hexyloxy, R₈=H compound 183 R₁=R₉=4-(bis(4-methylphenyl)amino)phenyl, R₂=R₁₀=n-decyl, R₇=t-butyl, R₈=n-hexyloxy compound 184 R₁=R₂=R₉=R₁₀=n-hexyl, R₇=n-hexyloxy, R₈=n-octyl compound 185 R₁=R₂=R₉=R₁₀=n-hexyl, R₇=R₈=n-hexyloxy

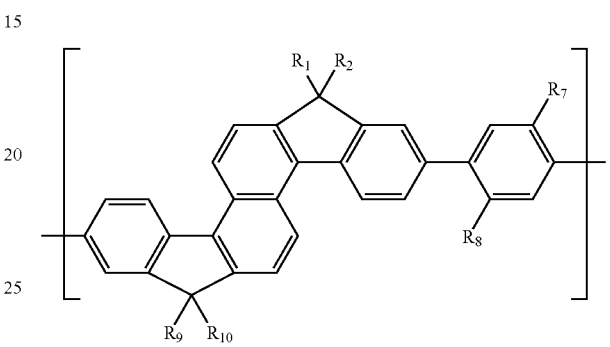

compound 186 R₁=R₂=R₉=R₁₀=n-hexyl, R₇=n-hexyloxy, R₈=H compound 187 R₁=R₂=R₉=R₁₀=n-hexyl, R₇=R₈=(4-diphenyl-amino)phenyl compound 188 R₁=R₂=R₇=R₈=R₉=R₁₀=n-hexyl compound 189 R₁=R₉=4-decylphenyl, R₂=R₁₀=H, R₇=R₈=n-hexyloxy

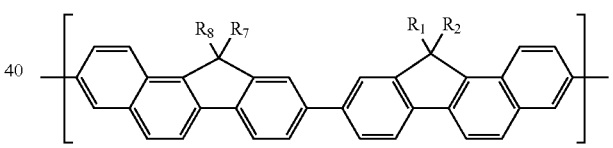

compound 190 R₁=R₂=R₇=R₈=n-hexyl compound 191 R₁=H, R₂=R₇=3,7-dimethyloctyl, R₈=(4-diphenyl-amino)phenyl compound 192 R₁=4-(bis(4-methylphenyl)amino)phenyl, R₂=n-decyl, R₇=R₈=n-hexyl

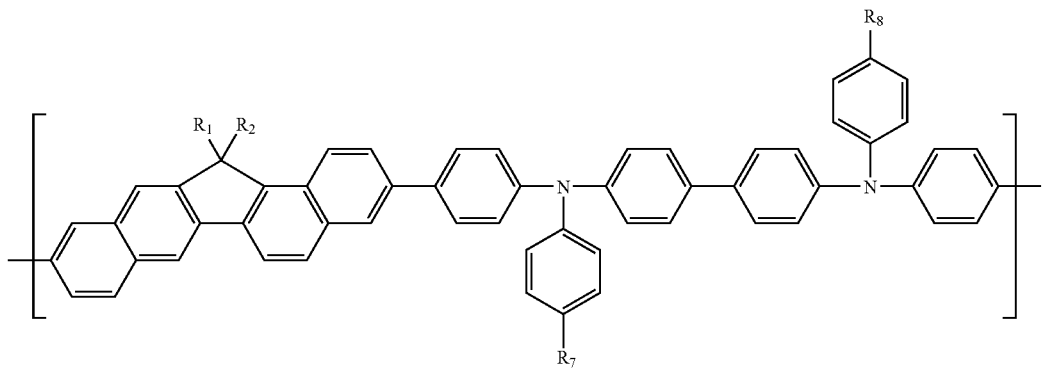

compound 193 R$_1$=R$_2$=n-hexyl, R$_7$=R$_8$=n-butyl
compound 194 R$_1$=R$_2$=2-ethylhexyl, R$_7$=R$_8$=(4-diphenylamino)phenyl
compound 195 R$_1$=R$_2$=R$_7$=R$_8$=n-hexyl
compound 196 R$_1$=4-decylphenyl, R$_2$=H, R$_7$=R$_8$=CF$_3$ compound 207 R$_1$=4-(bis(4-methylphenyl)amino)phenyl, R$_2$=n-decyl, R$_7$=n-butyl, R$_8$=n-hexyloxy

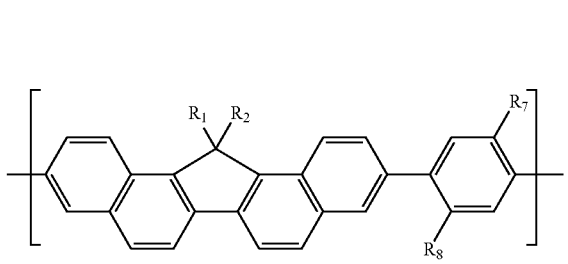

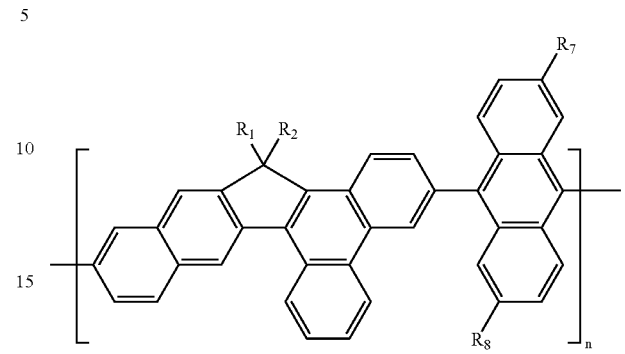

compound 197 R$_1$=R$_2$=n-hexyl, R$_7$=R$_8$=2-ethylhexyloxy
compound 198 R$_1$=R$_2$=n-hexyl, R$_7$=R$_8$=H
compound 199 R$_1$=2-ethylhexyl, R$_2$=n-hexyl, R$_7$=R$_8$=H
compound 200 R$_1$=n-hexyl, R$_2$=R$_7$=3,7-dimethyloctyl, R$_8$=(4-diphenyl-amino)phenyl
compound 201 R$_1$=2-ethylhexyl, R$_2$=n-hexyl, R$_7$=R$_8$=n-hexyloxy
compound 202 R$_1$=4-(bis(4-methylphenyl)amino)phenyl, R$_2$=n-decyl, R$_7$=t-butyl, R$_8$=n-hexyloxy compound 208 R$_1$=R$_2$=n-hexyl, R$_7$=R$_8$=2-ethylhexyloxy
compound 209 R$_1$=2-ethylhexyl, R$_2$=n-hexyl, R$_7$=R$_8$=n-butyl
compound 210 R$_1$=n-hexyl, R$_2$=(4-diphenylamino)phenyl, R$_7$=H, R$_8$=3,7-dimethyloctyl
compound 211 R$_1$=R$_2$=n-hexyl, R$_7$=R$_8$=4-(bis(4-methylphenyl)-amino)phenyl

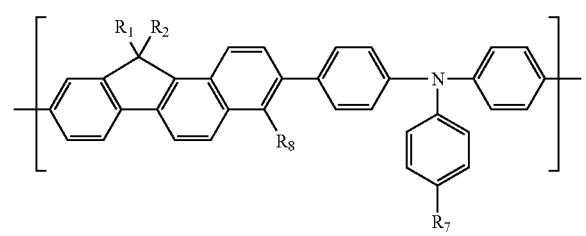

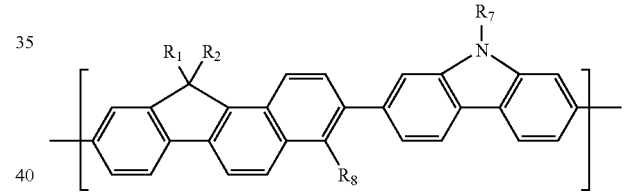

compound 203 R$_1$=R$_2$=n-hexyl, R$_7$=R$_8$=2-ethylhexyl
compound 204 R$_1$=2-ethylhexyl, R$_2$=n-hexyl, R$_7$=R$_8$=H
compound 205 R$_1$=n-hexyl, R$_2$=R$_8$=3,7-dimethyloctyl, R$_7$=(4-diphenyl-amino)phenyl
compound 206 R$_1$=R$_2$=n-hexyl, R$_7$=t-butyl, R$_8$=H compound 212 R$_1$=R$_2$=n-hexyl, R$_7$=R$_8$=2-ethylhexyl
compound 213 R$_1$=2-ethylhexyl, R$_2$=n-hexyl, R$_7$=4-t-butylphenyl, R$_8$=H
compound 214 R$_1$=n-hexyl, R$_2$=R$_8$=3,7-dimethyloctyl, R$_7$=(4-diphenyl-amino)phenyl
compound 215 R$_1$=R$_2$=n-hexyl, R$_7$=2-ethylhexyl, R$_8$=H

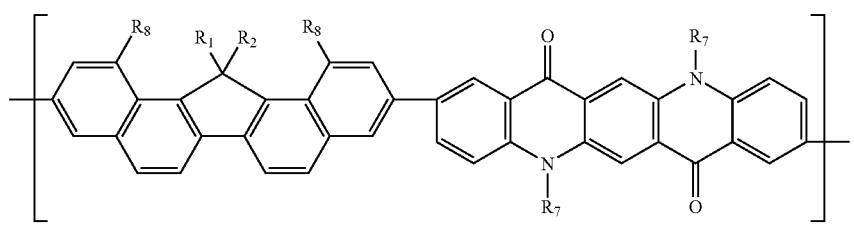

compound 216 R₁=R₂=n-hexyl, R₇=R₈=2-ethylhexyl
compound 217 R₁=2-ethylhexyl, R₂=n-hexyl, R₇=4-t-butylphenyl, R₈=H
compound 218 R₁=n-hexyl, R₂=3,7-dimethyloctyl, R₇=(4-diphenyl-amino)phenyl, R₈=n-hexyloxy

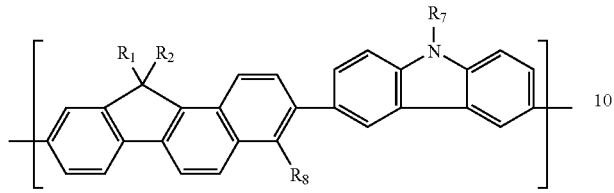

compound 219 R₁=R₂=n-hexyl, R₇=R₈=2-ethylhexyl
compound 220 R₁=2-ethylhexyl, R₂=n-hexyl, R₇=4-t-butylphenyl, R₈=n-hexyloxy
compound 221 R₁=R₂=n-hexyl, R₇=2-ethylhexyl, R₈=H

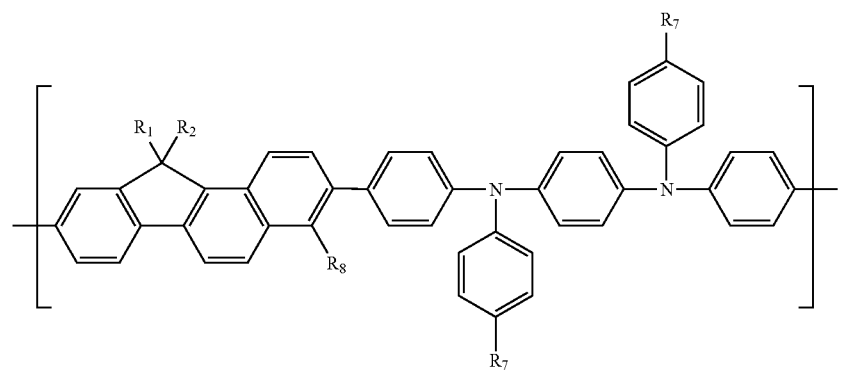

compound 222 R₁=R₂=n-hexyl, R₇=R₈=n-butyl
compound 223 R₁=R₂=2-ethylhexyl, R₇=R₈=(4-diphenylamino)phenyl
compound 224 R₁=R₂=R₇=R₈=n-hexyl
compound 225 R₁=4-decylphenyl, R₂=H, R₇=R₈=CF₃

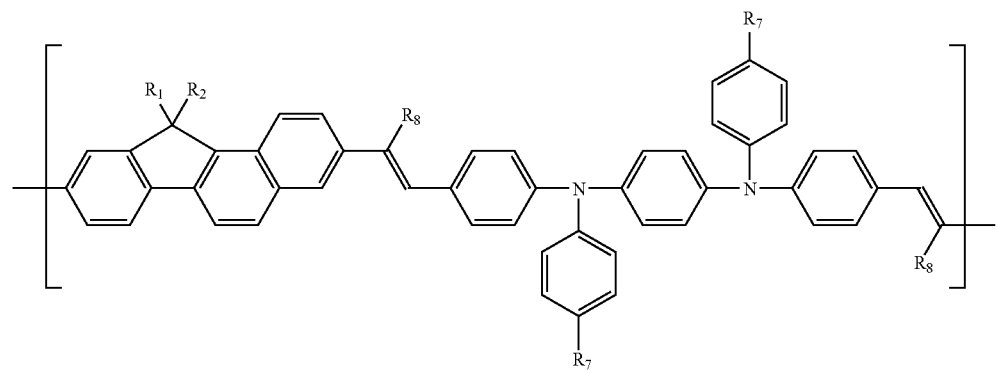

compound 226 R₁=R₂=n-hexyl, R₇=n-butyl, R₈=H
compound 227 R₁=R₂=2-ethylhexyl, R₇=4-t-butylphenyl, R₈=CN
compound 228 R₁=4-decylphenyl, R₂=H, R₇=CF₃, R₈=phenyl

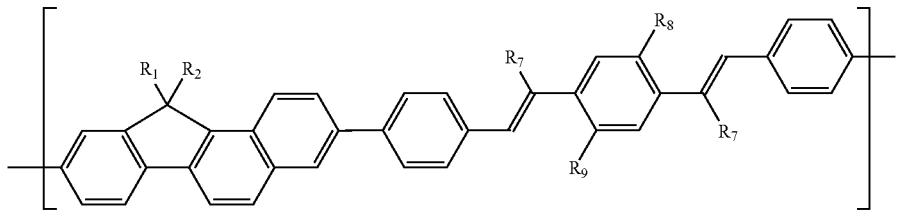

compound 229 $R_1=R_2=$n-hexyl, $R_7=$phenyl, $R_8=R_9=$2-ethylhexyl compound 230 $R_1=$2-ethylhexyl, $R_2=$n-hexyl, $R_7=R_8=$H, $R_9=$4-t-butylphenyl compound 231 $R_1=R_2=$n-hexyl, $R_7=$H, $R_8=$methoxy, $R_9=$3,7-dimethyl-octyloxy compound 232 $R_1=$n-hexyl, $R_2=R_8=$3,7-dimethyloctyl, $R_7=$H, $R_9=$(4-diphenylamino)phenyl

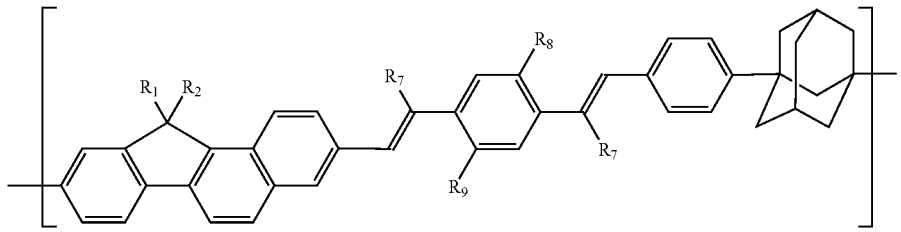

compound 233 $R_1=$2-ethylhexyl, $R_2=$n-hexyl, $R_7=$CN, $R_8=R_9=$4-t-butylphenyl compound 234 $R_1=R_2=$n-hexyl, $R_7=R_8=$H, $R_9=$2-ethylhexyl compound 235 $R_1=$4-decylphenyl, $R_2=R_8=$3,7-dimethyloctyl, $R_7=$H, $R_9=$(4-diphenylamino)phenyl

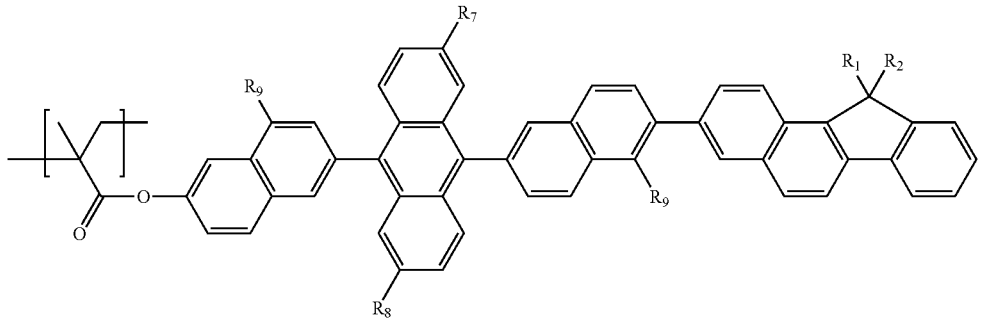

compound 236 $R_1=$2-ethylhexyl, $R_2=$n-hexyl, $R_7=$CN, $R_8=R_9=$4-t-butylphenyl compound 237 $R_1=R_2=$n-hexyl, $R_7=R_8=$H, $R_9=$2-ethylhexyl compound 238 $R_1=$4-decylphenyl, $R_2=R_8=$3,7-dimethyloctyl, $R_7=$H, $R_9=$(4-diphenylamino)phenyl

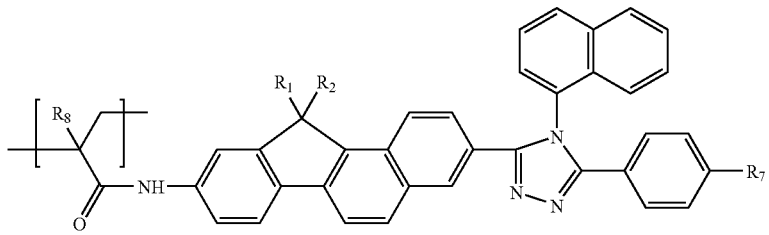

compound 239 R₁=2-ethylhexyl, R₂=n-hexyl, R₇=t-butyl, R₈=H
compound 240 R₁=R₂=n-hexyl, R₇=phenyl, R₈=CN
compound 241 R₁=4-decylphenyl, R₂=R₇=3,7-dimethyloctyl, R₈=methyl

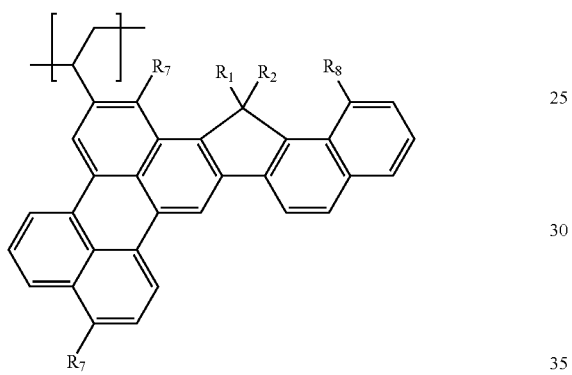

compound 242 R₁=R₂=R₇=R₈=2-ethylhexyl
compound 243 R₁=R₂=n-hexyl, R₇=4-decylphenyl, R₈=2-ethylhexyloxy
compound 244 R₁=(4-diaminophenyl)phenyl, R₂=R₇=3,7-dimethyloctyl, R₈=H

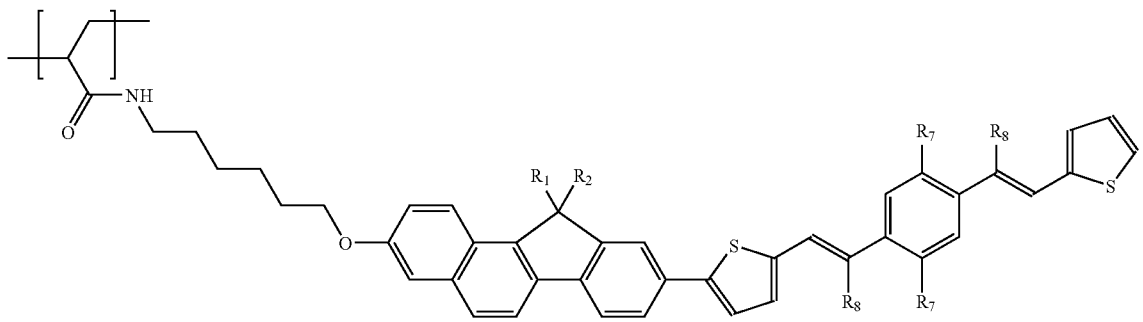

compound 245 R₁=2-ethylhexyl, R₂=n-hexyl, R₇=t-butyl, R₈=H
compound 246 R₁=R₂=n-hexyl, R₇=n-octyloxy, R₈=CN
compound 247 R₁=4-decylphenyl, R₂=R₇=3,7-dimethyloctyl, R₈=CN

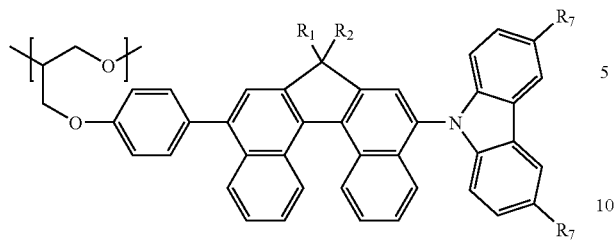

compound 248 R₁=2-ethylhexyl, R₂=n-hexyl, R₇=t-butyl
compound 249 R₁=R₂=n-hexyl, R₇=phenyl
compound 250 R₁=4-decylphenyl, R₂=n-octyl, R₇=CN
compound 251 R₁=4-(diphenylamino)phenyl, R₂=n-hexyl, R₇=n-hexyloxy

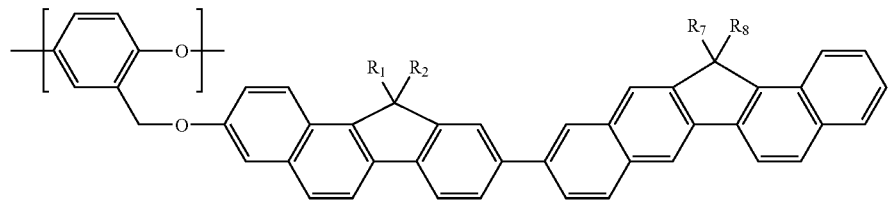

compound 252 R₁=R₂=2-ethylhexyl, R₇=R₈=4-t-butylphenyl
compound 253 R₁=R₂=R₇=R₈=n-octyl
compound 254 R₁=R₇=4-decylphenyl, R₂=R₈=3,7-dimethyloctyl

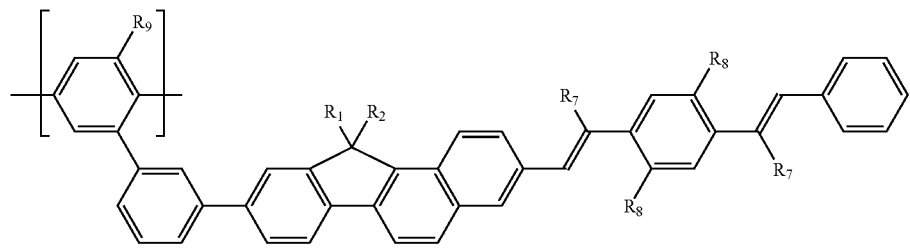

compound 255 R₁=2-ethylhexyl, R₂=n-hexyl, R₇=CN, R₈=R₉=4-t-butylphenyl
compound 256 R₁=R₂=n-hexyl, R₇=H, R₈=n-hexyloxy, R₉=2-ethylhexyl
compound 257 R₁=4-decylphenyl, R₂=R₈=3,7-dimethyloctyl, R₇=H, R₉=(4-diphenylamino)phenyl

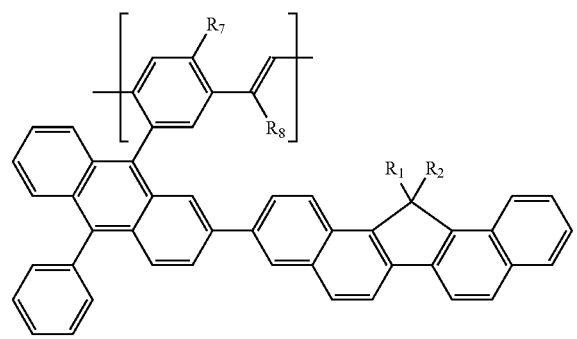

compound 258 R₁=2-ethylhexyl, R₂=n-hexyl, R₇=n-hexyl, R₈=H
compound 259 R₁=R₂=n-hexyl, R₇=n-octyloxy, R₈=CN
compound 260 R₁=R₇=4-decylphenyl, R₂=3,7-dimethyloctyl, R₈=CN compound 267 R₁=R₂=R₇=R₈=R₉=R₁₀=2-ethylhexyl compound 268 R₁=R₇=R₉=n-hexyl, R₂=R₈=R₁₀=4-t-butylphenyl

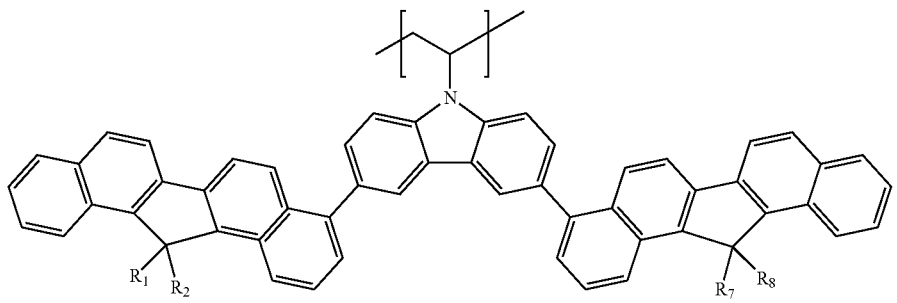

compound 261 R₁=R₂=R₇=R₈=2-ethylhexyl
compound 262 R₁=R₇=n-hexyl, R₂=R₈=(4-diphenylamino)phenyl
compound 263 R₁=n-hexyl, R₂=(4-diphenylamino)phenyl, R₇=H, R₈=4-decylphenyl

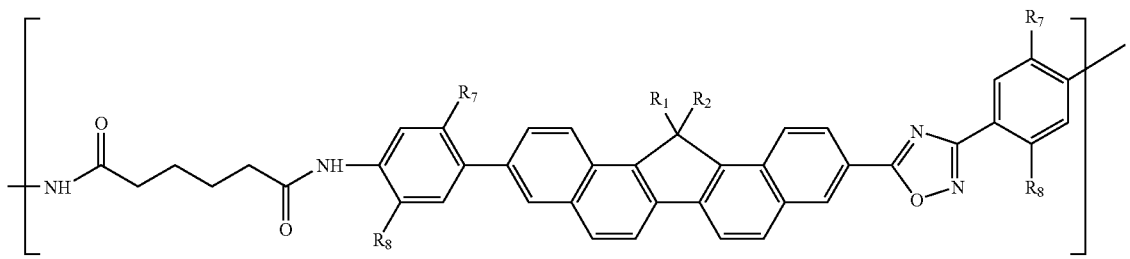

compound 264 R₁=2-ethylhexyl, R₂=n-hexyl, R₇=t-butyl, R₈=n-butyloxy
compound 265 R₁=R₂=n-hexyl, R₇=phenyl, R₈=H
compound 266 R₁=4-decylphenyl, R₂=3,7-dimethyloctyl, R₇=3,7-dimethyloctyl, R₈=methoxy

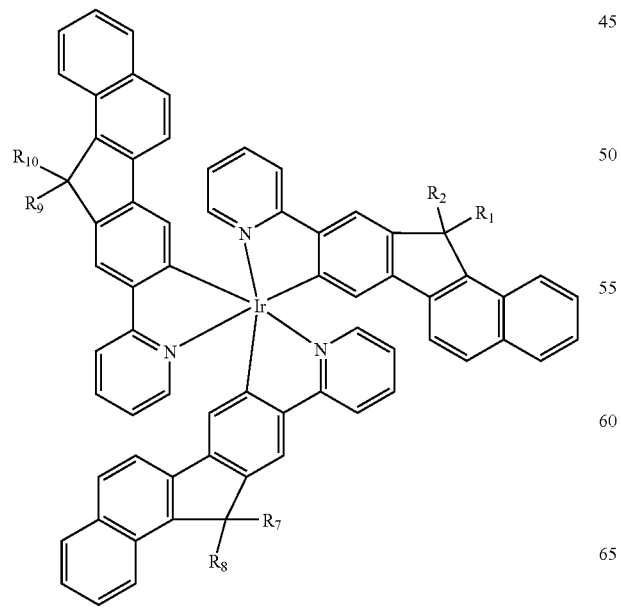

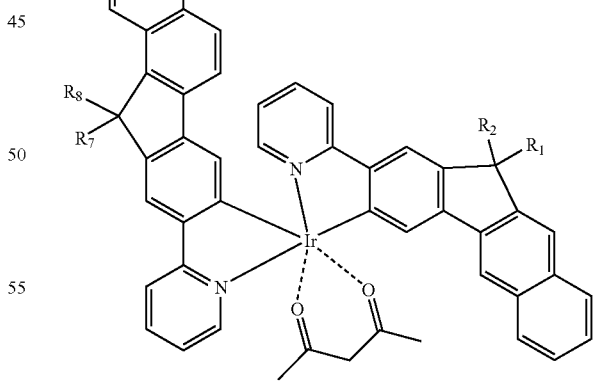

compound 269 R₁=R₂=n-hexyl, R₇=R₈=2-ethylhexyl
compound 270 R₁=R₇=H, R₂=R₈=4-t-butylphenyl
compound 271 R₁=4-(diphenylamino)phenyl, R₂=R₇=n-hexyl, R₈=4-t-butylphenyl

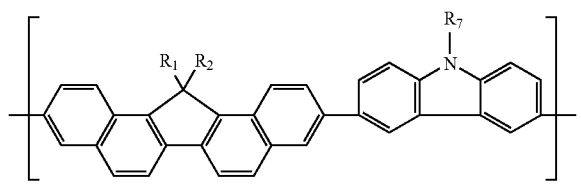

compound 272 R₁=R₂=n-hexyl, R₇=2-ethylhexyl
compound 273 R₁=n-hexyl, R₂=R₇=2-ethylhexyl
compound 274 R₁=R₂=2-ethylhexyl, R₇=4-t-butylphenyl

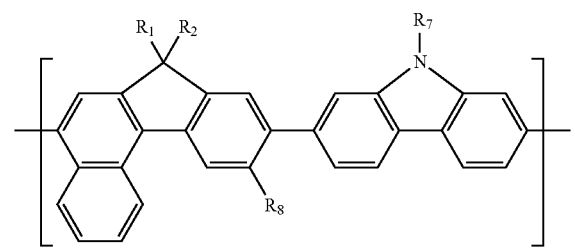

compound 275 R₁=R₂=n-hexyl, R₇=R₈=2-ethylhexyl
compound 276 R₁=2-ethylhexyl, R₂=n-hexyl, R₇=4-t-butylphenyl, R₈=H
compound 277 R₁=n-hexyl, R₂=R₈=3,7-dimethyloctyl, R₇=(4-diphenyl-amino)phenyl
compound 278 R₁=phenyl, R₂=4-decylphenyl, R₇=2-ethylhexyl, R₈=H

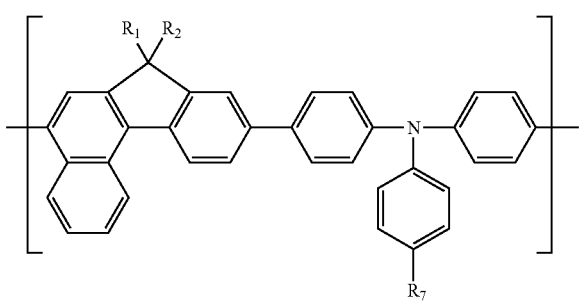

compound 279 R₁=R₂=n-hexyl, R₇=R₈=n-butyl
compound 280 R₁=R₂=n-hexyl, R₇=t-butyl, R₈=H
compound 281 R₁=R₂=R₇=R₈=n-hexyl compound 282 R₁=4-decylphenyl, R₂=phenyl, R₇=t-butyl, R₈=H

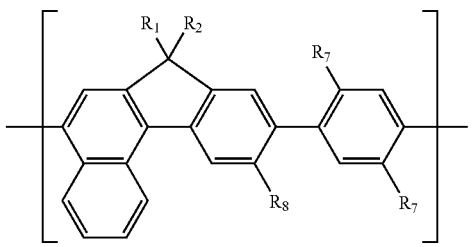

compound 283 R₁=R₂=n-hexyl, R₇=R₈=n-butyl
compound 284 R₁=R₂=n-hexyl, R₇=n-hexyloxy, R₈=H
compound 285 R₁=R₂=R₇=R₈=n-hexyl
compound 286 R₁=R₂=n-hexyl, R₇=n-octyl, R₈=H
compound 287 R₁=4-decylphenyl, R₂=phenyl, R₇=t-butyl, R₈=H

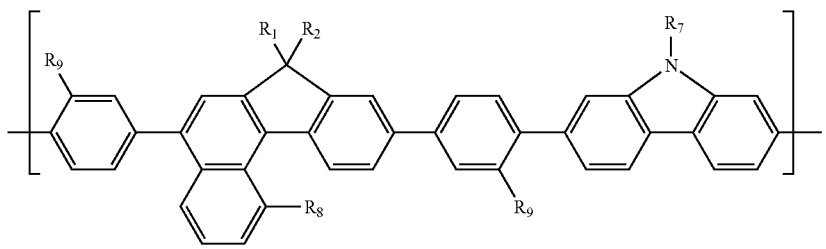

compound 288 R₁=R₂=n-hexyl, R₇=R₈=n-butyl
compound 289 R₁=R₂=n-hexyl, R₇=t-butyl, R₈=H
compound 290 R₁=R₂=R₇=R₈=n-hexyl
compound 291 R₁=4-decylphenyl, R₂=phenyl, R₇=t-butyl, R₈=H compound 292 R$_1$=R$_2$=n-hexyl, R$_7$=R$_8$=R$_9$=2-ethylhexyl
compound 293 R$_1$=2-ethylhexyl, R$_2$=n-hexyl, R$_7$=4-t-butylphenyl, R$_8$=R$_9$=H
compound 294 R$_1$=R$_2$=R$_9$=3,7-dimethyloctyl, R$_7$=R$_8$=(4-diphenyl-amino)phenyl
compound 295 R$_1$=phenyl, R$_2$=4-decylphenyl, R$_7$=2-ethylhexyl, R$_8$=H, R$_9$=di(4-methylphenyl)amino

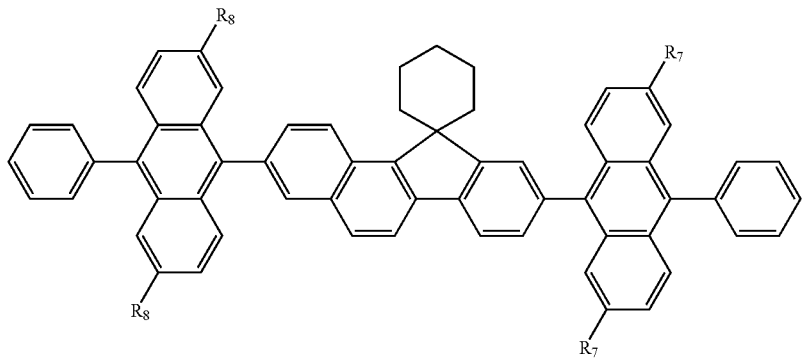

compound 296 R$_7$=2-ethylhexyl, R$_8$=n-hexyl
compound 297 R$_7$=R$_8$=(4-diphenylamino)phenyl
compound 298 R$_7$=n-hexyloxy, R$_8$=(4-diphenylamino)phenyl

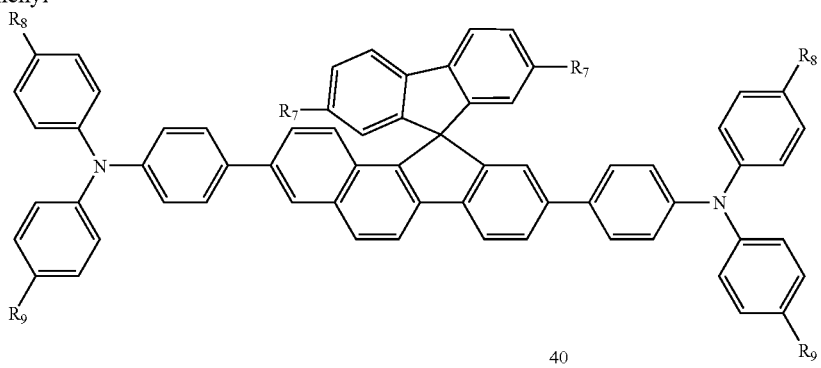

compound 299 R$_7$=2-ethylhexyl, R$_8$=R$_9$=n-hexyloxy
compound 300 R$_7$=R$_8$=(4-diphenylamino)phenyl, R$_9$=methyl
compound 301 R$_7$=n-hexyloxy, R$_8$=n-octyl, R$_9$=t-butyl compound 302 R$_7$=2-ethylhexyl, R$_8$=n-hexyloxy
compound 303 R$_7$=R$_8$=(4-diphenylamino)phenyl
compound 304 R$_7$=n-hexyloxy, R$_8$=H

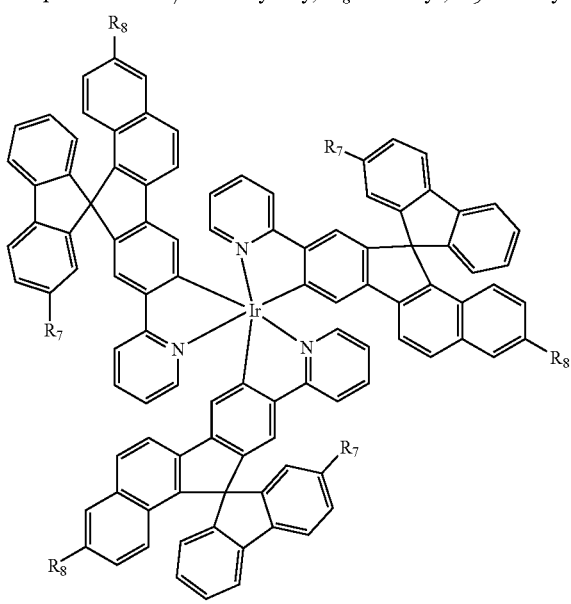

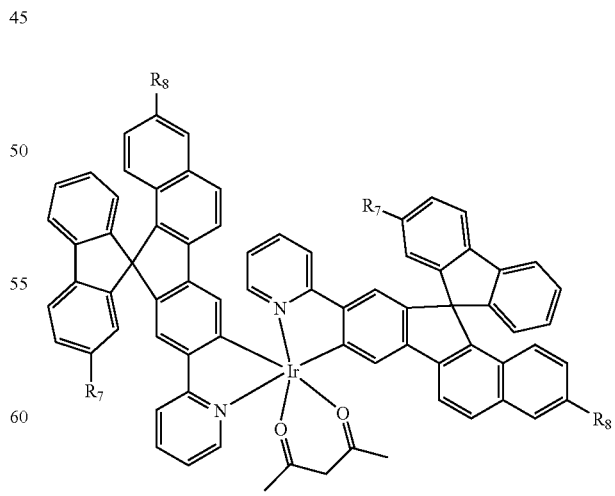

compound 305 R$_7$=2-ethylhexyl, R$_8$=n-hexyloxy
compound 306 R$_7$=R$_8$=(4-diphenylamino)phenyl
compound 307 R$_7$=n-hexyloxy, R$_8$=H compound 314 R$_7$=2-ethylhexyl, R$_8$=H
compound 315 R$_7$=n-bexyloxy, R$_8$=t-butyl

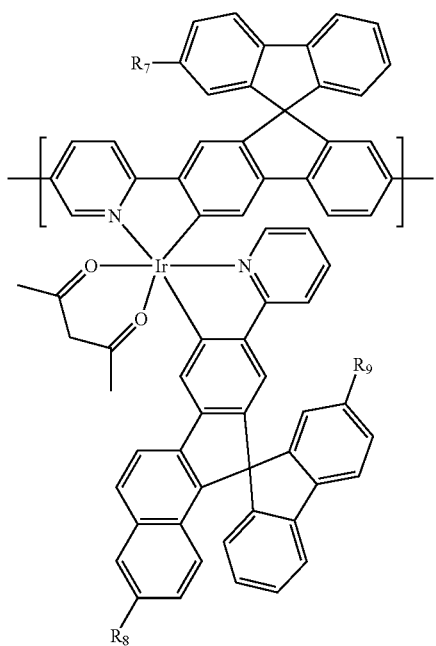

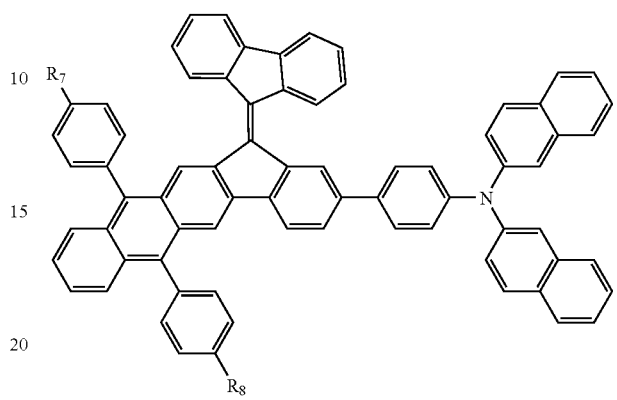

compound 308 R$_7$=2-ethylhexyl, R$_8$=H, R$_9$=n-hexyloxy
compound 309 R$_7$=R$_8$=(4-diphenylamino)phenyl, R$_9$=H
compound 310 R$_7$=n-hexyloxy, R$_8$=n-octyl, R$_9$=t-butyl compound 316 R$_7$=2-ethylhexyl, R$_8$=n-hexyloxy
compound 317 R$_7$=R$_8$=(4-diphenylamino)phenyl
compound 318 R$_7$=R$_8$=H

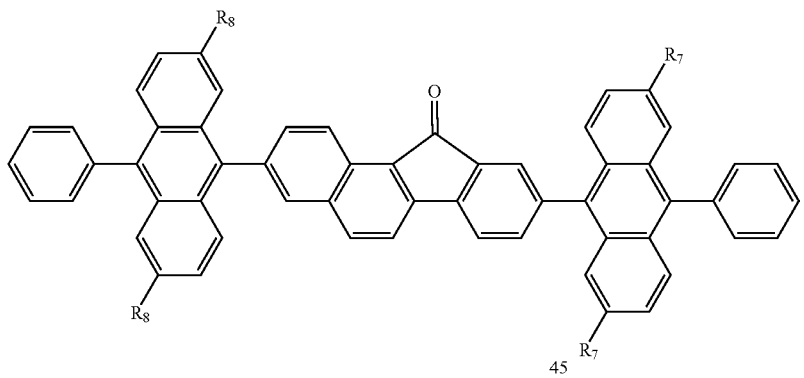

compound 311 R$_7$=2-ethylhexyl, R$_8$=n-hexyloxy
compound 312 R$_7$=R$_8$=(4-diphenylamino)phenyl
compound 313 R$_7$=n-hexyloxy, R$_8$=t-butyl

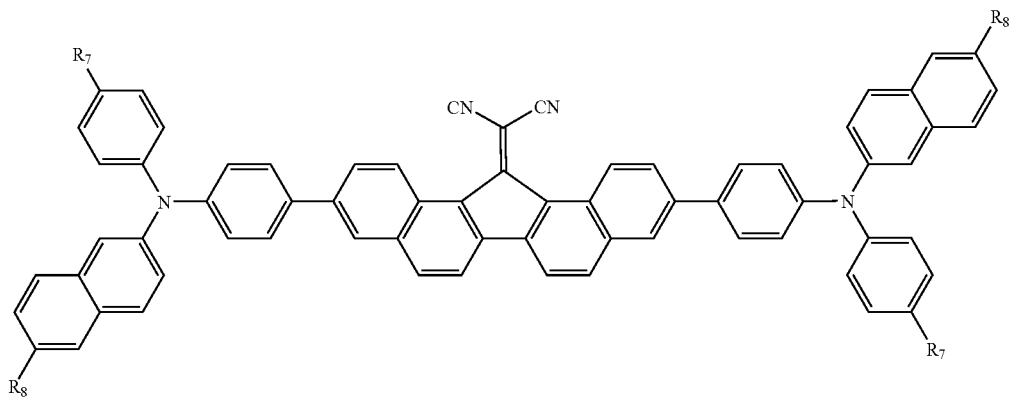

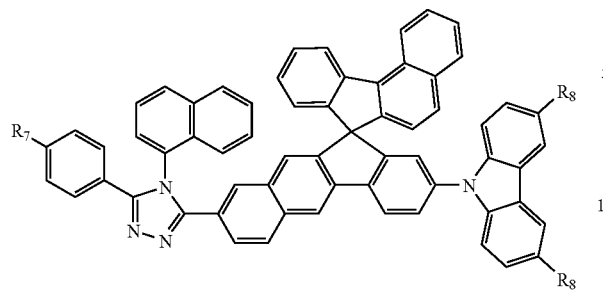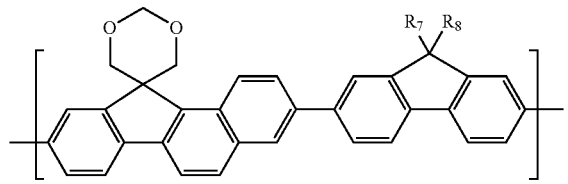

compound 319 R$_7$=2-ethylhexyl, R$_8$=H
compound 320 R$_7$=(4-diphenylamino)phenyl, R$_8$=t-butyl
compound 321 R$_7$=R$_8$=H compound 328 R$_7$=R$_8$=2-ethylhexyl
compound 329 R$_7$=R$_8$=(4-diphenylamino)phenyl
compound 330 R$_7$=4-hexylphenyl, R$_8$=hexyl

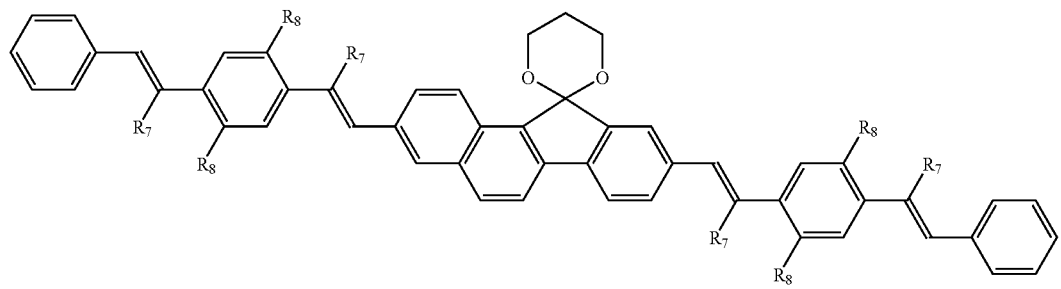

compound 322 R$_7$=H, R$_8$=2-ethylhexyl
compound 323 R$_7$=H, R$_8$=n-hexyloxy
compound 324 R$_8$=(bis(4-methylphenyl)amino)phenyl, R$_7$=CN

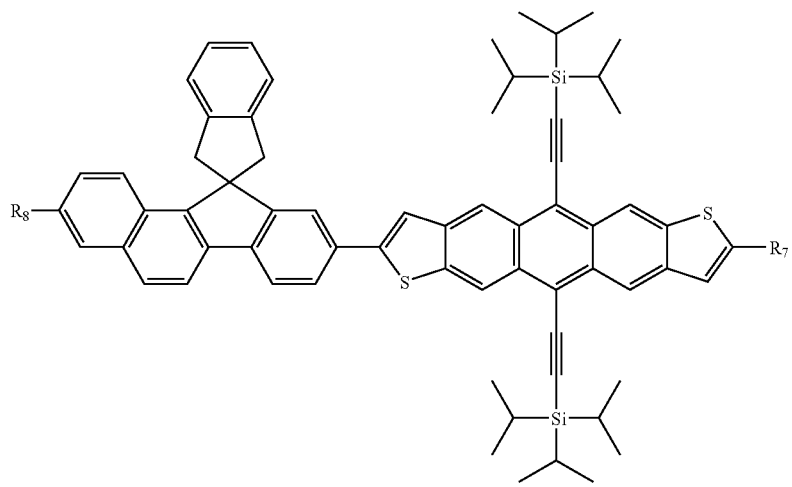

compound 325 R$_7$=2-ethylhexyl, R$_8$=H
compound 326 R$_7$=(4-diphenylamino)phenyl, R$_8$=t-butyl
compound 327 R$_7$=R$_8$=H

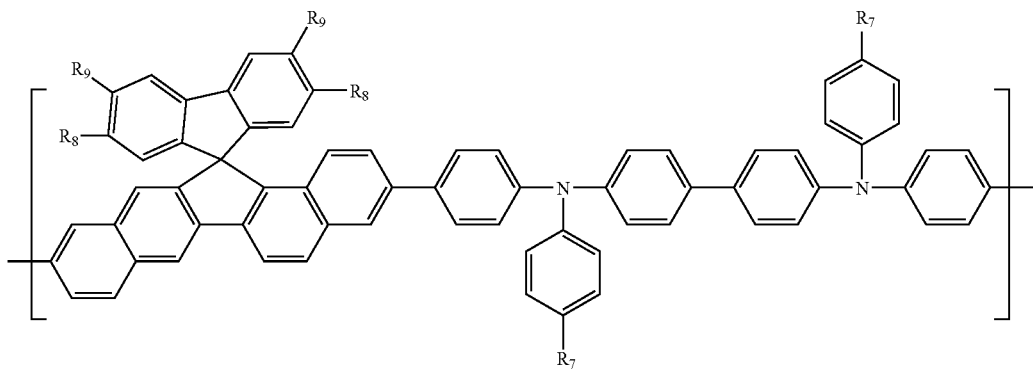
compound 331 R$_7$=t-butyl, R$_8$=H, R$_9$=n-hexyloxy
compound 332 R$_7$=R$_8$=(4-diphenylamino)phenyl, R$_9$=H
compound 333 R$_7$=n-hexyloxy, R$_8$=n-octyl, R$_9$=t-butyl
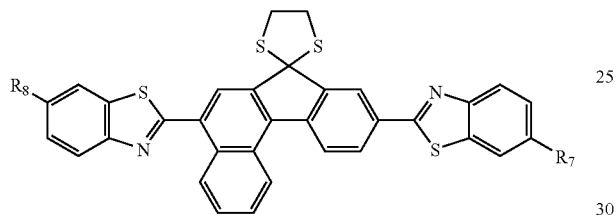
compound 334 R$_7$=2-ethylhexyl, R$_8$=n-hexyloxy
compound 335 R$_7$=R$_8$=H
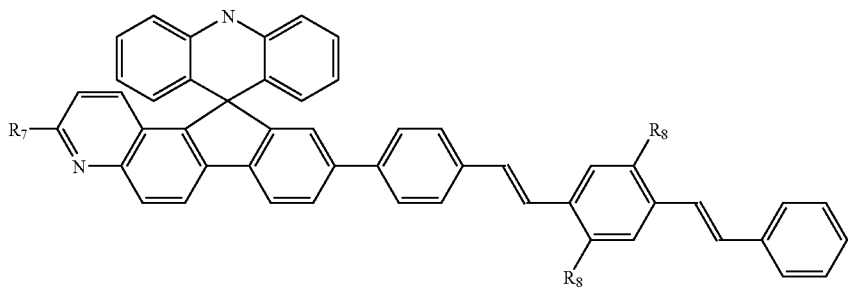
compound 336 R$_7$=2-ethylhexyl, R$_8$=n-hexyloxy
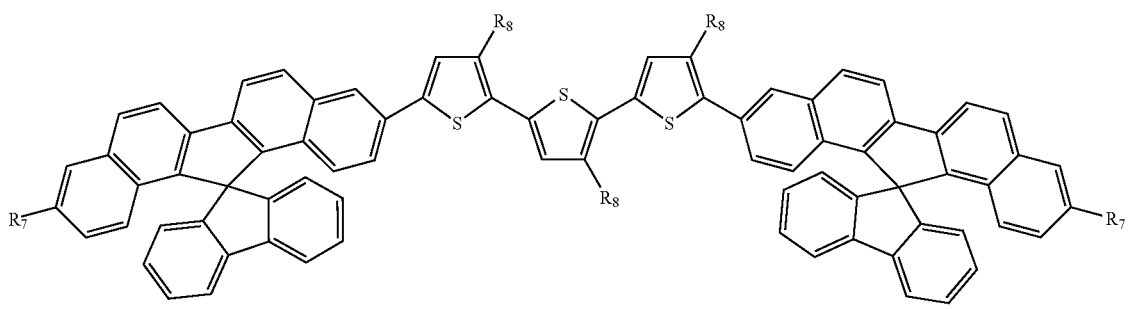

compound 337 R$_7$=H, R$_8$=(4-diphenylamino)phenyl
compound 338 R$_7$=n-hexyloxy, R$_8$=H
compound 339 R$_7$=R$_8$=2-ethylhexyl
compound 340 R$_7$=hexyloxy, R$_8$=H
compound 341 R$_7$=H, R$_8$=hexyl compound 342 R$_7$=t-butyl, R$_8$=H, R$_9$=n-hexyloxy
compound 343 R$_7$=methoxy, R$_8$=2-ethylhexyl, R$_9$=H
compound 344 R$_7$=methoxycarbonyl, R$_8$=R$_9$=n-hexyl

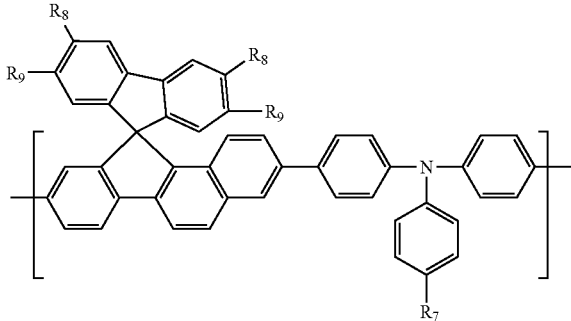

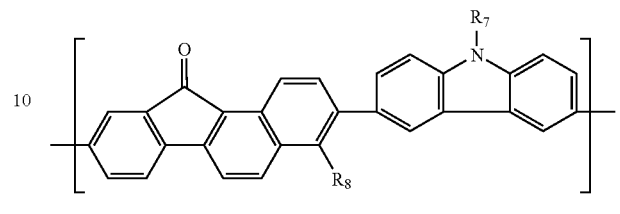

compound 345 R$_7$=R$_8$=2-ethylhexyl
compound 346 R$_7$=4-t-butylphenyl, R$_8$=H

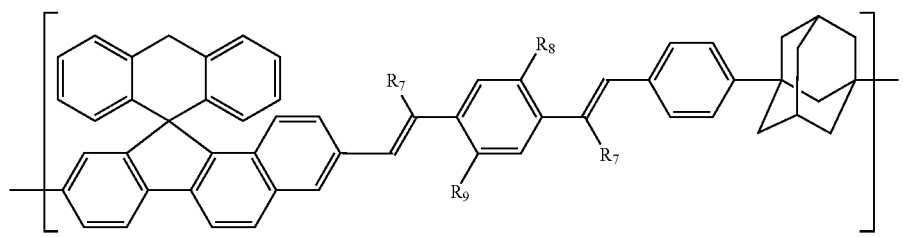

compound 347 R$_7$=CN, R$_8$=R$_9$=4-hexylphenyl
compound 348 R$_7$=H, R$_8$=R$_9$=2-ethylhexyl
compound 349 R$_8$=3,7-dimethyloctyoxyl, R$_7$=CN, R$_9$=methoxy

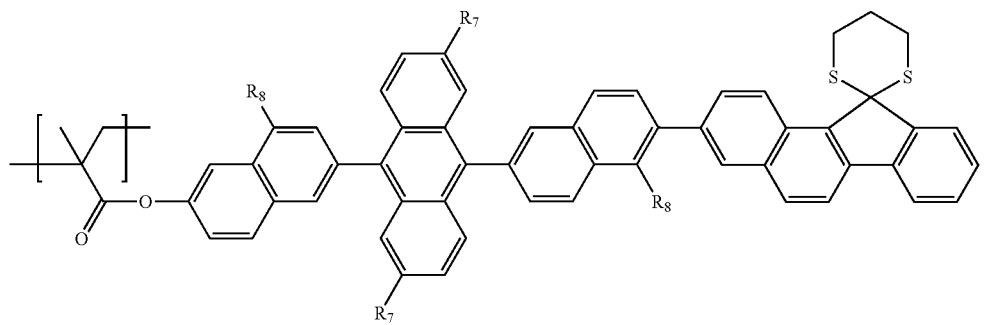

compound 350 R$_7$=CN, R$_8$=4-hexylphenyl
compound 351 R$_7$=octyloxy, R$_8$=H
compound 352 R$_8$=3,7-dimethyloctyl, R$_7$=H

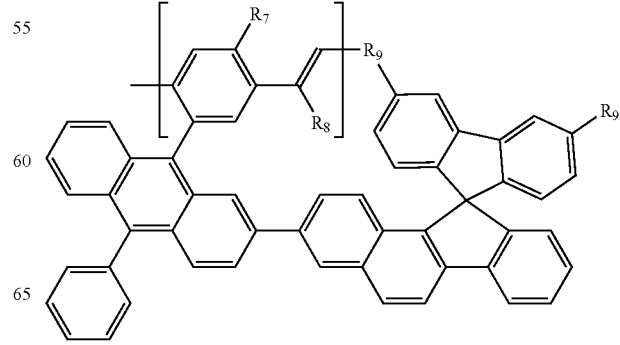

compound 353 R₇=R₉=n-hexyl, R₈=H
compound 354 R₁=R₂=n-hexyl, R₇=n-octyloxy, R₈=CN, R₉=H
compound 355 R₇=4-decylphenyl, R₈=CN, R₉=3,7-dimethyloctyl compound 358 R₁=R₂=2-ethylhexyl, R₇=t-butyl, R₈=diphenylamino
compound 359 R₁=R₂=4-(bis(4-methylphenyl)amino)phenyl, R₇=H, R₈=phenyl

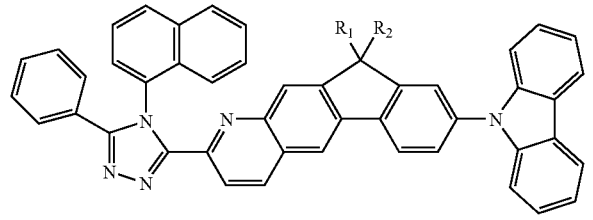

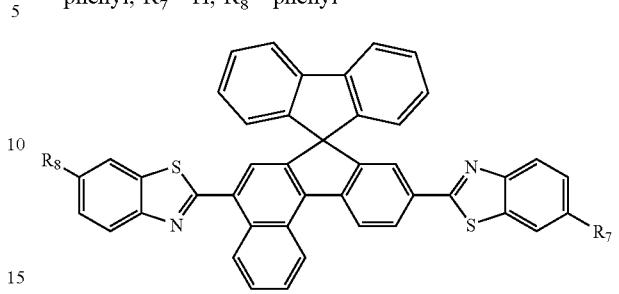

compound 356 R₁=R₂=R₇=R₈=2-ethylhexyl
compound 357 R₁=H, R₂=R₇=4-octylphenyl, R₈=2-ethylhexyloxy compound 360 R₇=2-ethylhexyl, R₈=n-hexyloxy
compound 361 R₇=R₈=H

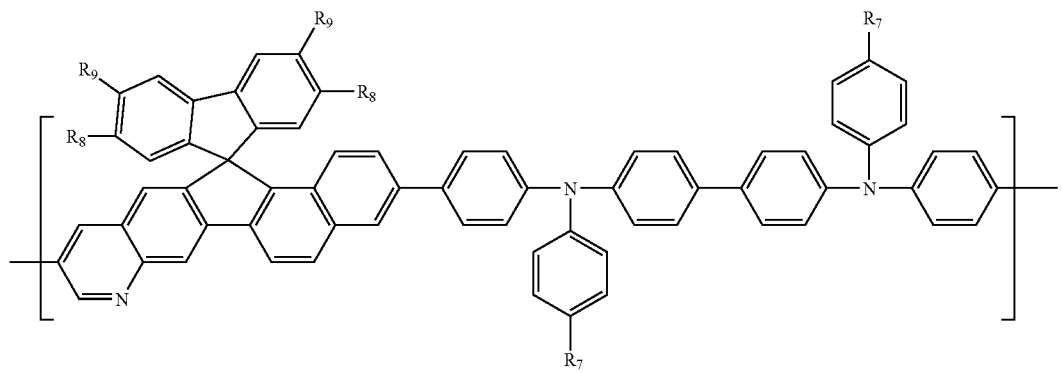

compound 362 R₇=t-butyl, R₈=H, R₉=n-hexyloxy
compound 363 R₇=R₈=(4-diphenylamino)phenyl, R₉=H
compound 364 R₇=n-hexyloxy, R₈=n-octyl, R₉=t-butyl

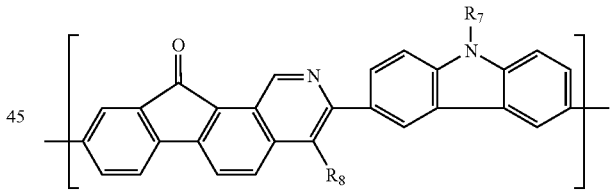

compound 365 R₇=R₈=2-ethylhexyl
compound 366 R₇=4-t-butylphenyl, R₈=H

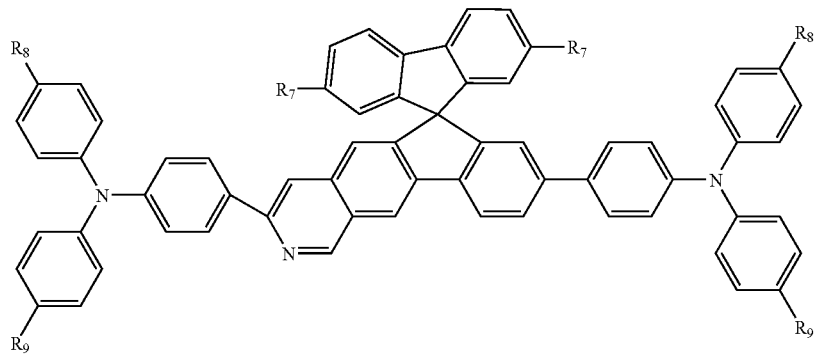

compound 367 R₇=2-ethylhexyl, R₈=R₉=n-hexyloxy
compound 368 R₇=R₈=(4-diphenylamino)phenyl, R₉=methyl
compound 369 R₇=n-hexyloxy, R₈=n-octyl, R₉=t-butyl

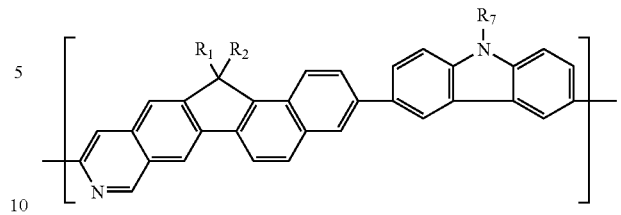

compound 372 R₁=R₂=n-hexyl, R₇=2-ethylhexyl
compound 373 R₁=n-hexyl, R₂=R₇=2-ethylhexyl
compound 374 R₁=R₂=2-ethylhexyl, R₇=4-t-butylphenyl

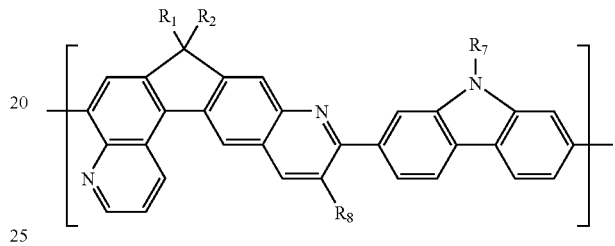

compound 375 R₁=R₂=n-hexyl, R₇=R₈=2-ethylhexyl
compound 376 R₁=2-ethylhexyl, R₂=n-hexyl, R₇=4-t-butylphenyl, R₈=H
compound 377 R₁=n-hexyl, R₂=R₈=3,7-dimethyloctyl, R₇=(4-diphenyl-amino)phenyl
compound 378 R₁=phenyl, R₂=4-decylphenyl, R₇=2-ethylhexyl, R₈=H

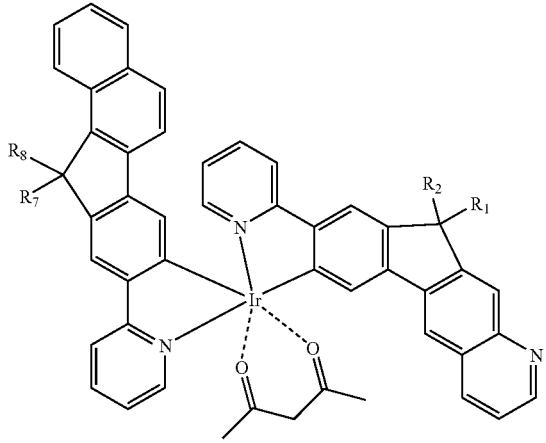

compound 370 R₁=R₇=H, R₂=R₈=4-t-butylphenyl
compound 371 R₁=4-(diphenylamino)phenyl, R₂=R₇=n-hexyl, R₈=4-t-butylphenyl

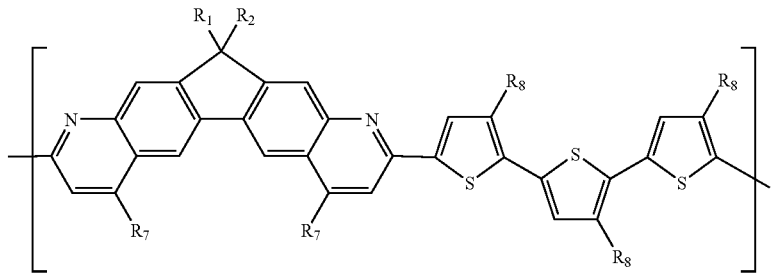

compound 379 R₁=R₂=n-hexyl, R₇=n-hexyloxy, R₈=2-ethylhexyl
compound 380 R₁=R₇=n-hexyl, R₂=3,7-dimethyloctyl, R₈=(4-diphenyl-amino)phenyl
compound 381 R₁=R₂=R₇=R₈=n-hexyl
compound 382 R₁=4-(bis(4-methylphenyl)amino)phenyl, R₂=n-decyl, R₇=methyl, R₈=n-hexyl

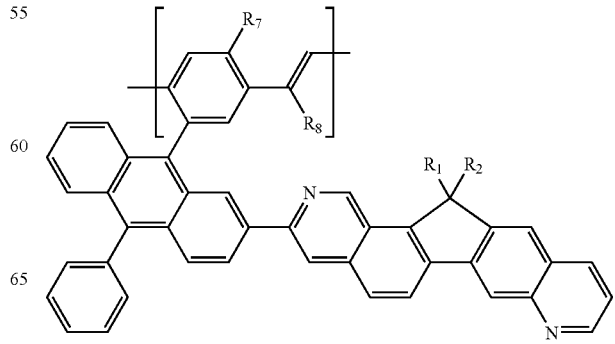

compound 383 R₁=2-ethylhexyl, R₂=n-hexyl, R₇=n-hexyl, R₈=H
compound 384 R₁=R₂=n-hexyl, R₇=n-octyloxy, R₈=CN
compound 385 R₁=R₇=4-decylphenyl, R₂=3,7-dimethyloctyl, R₈=CN

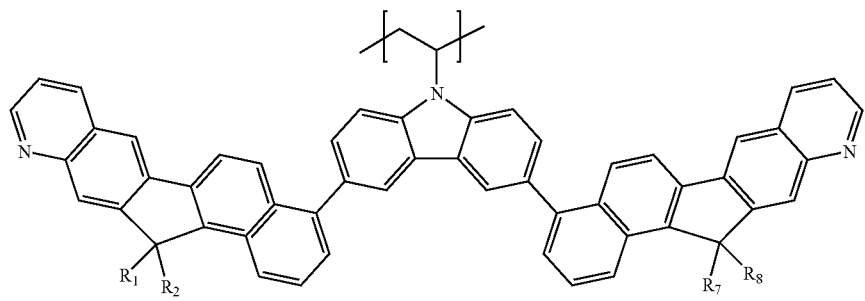

compound 386 R₁=R₂=R₇=R₈=2-ethylhexyl
compound 387 R₁=R₇=n-hexyl, R₂=R₈=(4-diphenylamino)phenyl
compound 388 R₁=n-hexyl, R₂=(4-diphenylamino)phenyl, R₇=H, R₈=4-decylphenyl

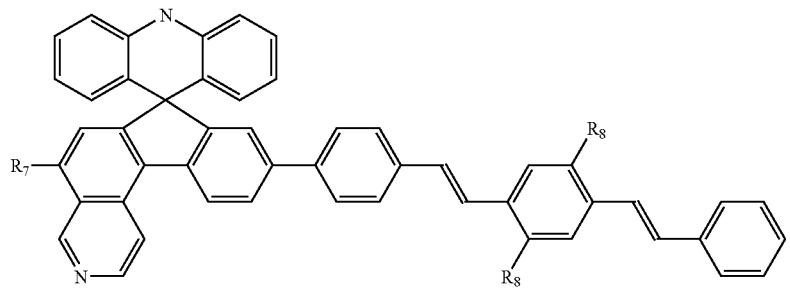

compound 389 R₇=2-ethylhexyl, R₈=n-hexyloxy
compound 390 R₇=H, R₈=(4-diphenylamino)phenyl
compound 391 R₇=n-hexyloxy, R₈=H

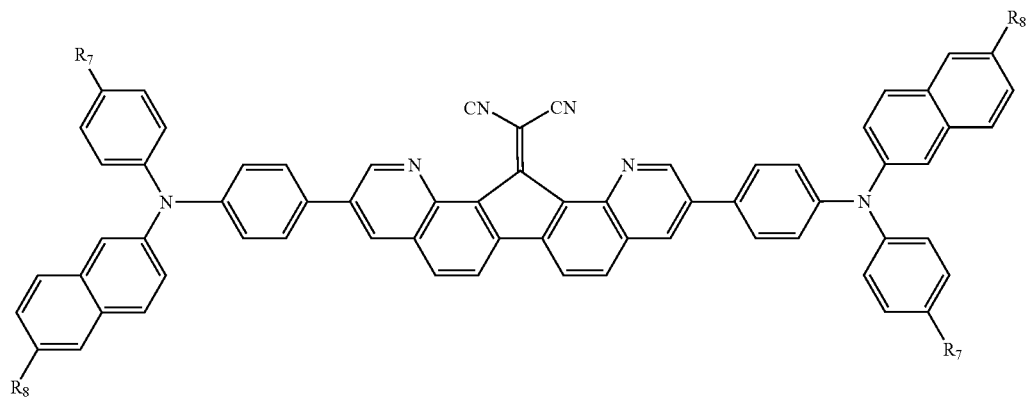

compound 392 R₇=2-ethylhexyl, R₈=H
compound 393 R₇=n-hexyloxy, R₈=t-butyl

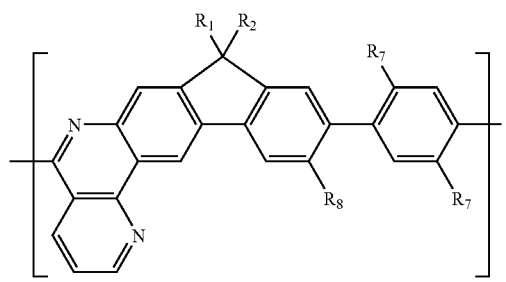

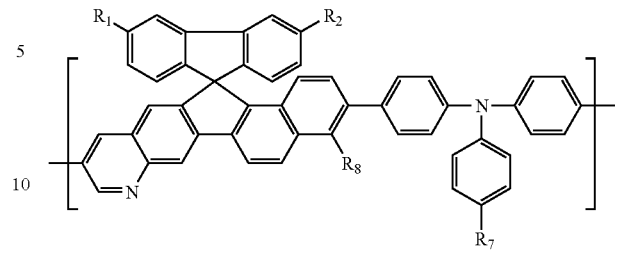

compound 397 R₁=4-decylphenyl, R₂=phenyl, R₇=t-butyl, R₈=H compound 394 R₁=R₂=n-hexyl, R₇=n-hexyloxy, R₈=H
compound 395 R₁=R₂=R₇=R₈=n-hexyl
compound 396 R₁=R₂=n-hexyl, R₇=n-octyl, R₈=H compound 398 R₁=R₂=n-hexyl, R₇=R₈=n-butyl
compound 399 R₁=R₂=n-hexyl, R₇=t-butyl, R₈=H
compound 400 R₁=R₂=R₇=R₈=n-hexyl

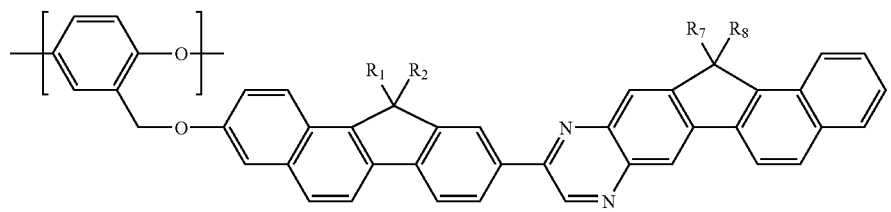

compound 401 R₁=R₂=2-ethylhexyl, R₇=R₈=4-t-butylphenyl
compound 402 R₁=R₂=R₇=R₈=n-octyl
compound 403 R₁=R₇=4-decylphenyl, R₂=R₈=3,7-dimethyloctyl

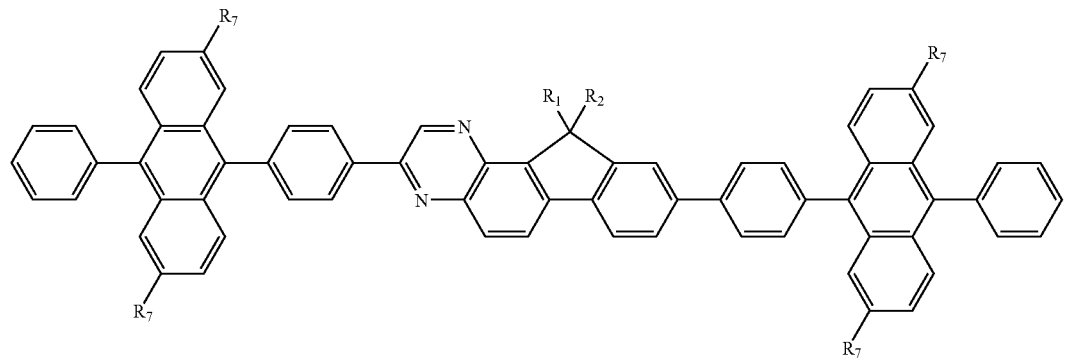

compound 404 R₁=n-hexyl, R₂=2-ethylhexyl, R₇=t-butyl
compound 405 R₁=n-hexyl, R₂=R₇=2-ethyl hexyl
compound 406 R₁=n-hexyl, R₂=2-ethylhexyl, R₇=2-ethylhexyloxy

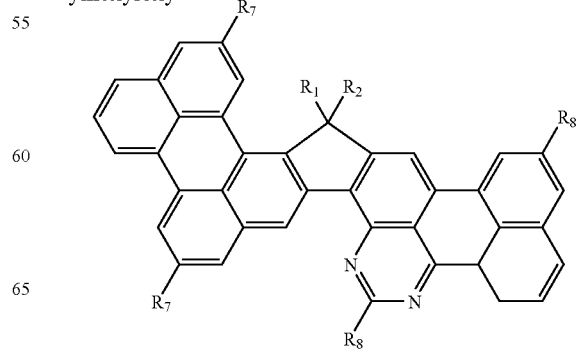

compound 407 $R_1=R_7=$n-hexyl, $R_2=R_8=$2-ethylhexyl
compound 408 $R_1=$n-hexyl, $R_2=$2-ethylhexyl, $R_7=$2-ethylhexyloxy, $R_8=$diphenylamino
compound 409 $R_1=$H, $R_2=R_8=$4-n-decylphenyl, $R_7=$2-ethylhexyloxy.

The specific molecular structures can be the combination of any of the above drawn structures.

Organic compounds comprising complex fluorene structures (I), (II) or (III) can be synthesized using known methods. For polymers, the polymerization method and the molecular weights of the resulting polymers used in the present invention are not necessary to be particularly restricted. The molecular weights of the polymers are at least 1000, and preferably at least 2000. The polymers can be prepared by condensation polymerizations, such as coupling reactions including Pd-catalyzed Suzuki coupling, Stille coupling or Heck coupling, or Ni-mediated Yamamoto coupling, or by condensation reaction between di-(acid chlorides) with di-amines, di-alcohols or di-phenols in the presence of bases, or by other condensation methods such as Wittig reaction, or Homer-Emmons reaction, or Knoevenagel reaction, or dehalogenation of dibenzyl halides, or by free radical polymerization of vinyl compounds, or ring-opening polymerization cyclic compounds, or ring-opening metathesis polymerization. Preferably polymers are prepared by Suzuki coupling reaction.

Suzuki coupling reaction was first reported by Suzuki, et al. on the coupling of aromatic boronic acid derivatives with aromatic halides (Suzuki, A. et al., *Synthetic Comm*. 1981, 11(7), 513). Since then, this reaction has been widely used to prepared polymers for various applications (Ranger, M., et al., *Macromolecules* 1997, 30, 7686). The reaction involves the use of a palladium-based catalyst such as a soluble Pd compound either in the state of Pd (II) or Pd (0), a base such as an aqueous inorganic alkaline carbonate or bicarbonate, and a solvent for the reactants or product. The preferred Pd catalyst is a Pd (0) complex such as $Pd(PPh_3)_4$ or a Pd (II) salt such as $Pd(PPh_3)_2Cl_2$ or $Pd(OAc)_2$ with a tertiary phosphine ligand, and used in the range of 0.01-10 mol % based on the functional groups of the reactants. Polar solvents such as THF and non-polar solvents toluene can be used however, the non-polar solvent is believed to slow down the reaction. Modified processes were reported to prepare conjugated polymers for EL devices from the Suzuki coupling of aromatic halides and aromatic boron derivatives (Inbasekaran, M., et al., U.S. Pat. No. 5,777,070 (1998); Towns, C. R., et al. PCT WO00/53656, 2000). A variation of the Suzuki coupling reaction replaces the aromatic halide with an aromatic trifluoromethanesulfonate (triflate) (Ritter, K., Synthesis, 1993, 735). Aromatic triflates are readily prepared from the corresponding phenol derivatives. The advantages of using aromatic triflates are that the phenol derivatives are readily accessible and can be protected/deprotected during complex synthesis. For example, aromatic halides normally would react under various coupling conditions to produce unwanted by-product and lead to much more complicated synthetic schemes. However, phenol derivatives can be readily protected by various protecting groups that would not interfere with functional group transformation and be deprotected to produce back the phenol group that then can be converted to triflates. The diboron derivatives can be prepared from the corresponding dihalide or ditriflate.

The present invention also provides a process for preparing a conjugated polymer which includes in the polymerization reaction mixture: (a) an aromatic monomer having at least two reactive triflate groups and an aromatic monomer having at least two reactive boron derivative groups selected from boronic acid, boronic ester, or borane groups or an aromatic monomer having one reactive triflate group and one boron derivative group selected from boronic acid, boronic ester, or borane groups; (b) a catalytic amount of a palladium catalyst; (c) an organic or inorganic base; and (d) an organic solvent. The process of the invention produces conjugated polymers with relatively low polydispersity, high molecular weight in a relatively short reaction time. The term "conjugated polymer" refers to either a fully conjugated polymer that is conjugated along the full length of its chain and processes a delocalized pi-electron system along the chain, or a partially conjugated polymer that contains both conjugated and non-conjugated segments.

The aromatic monomers used to form conjugated polymers of the present invention should have the appropriate functional groups: the triflate and boron derivative groups. The term aromatic or aryl refers to any monomer that has triflate or boron derivative groups attached directly to the aromatic or heteroaromatic rings. The present process can be used to polymerize two systems to form a linear polymer: 1) an aryl di-triflate monomer containing two reactive triflate groups and an aryl di-boron monomer containing two reactive boron derivative functional groups; and 2) an aryl monomer containing both reactive triflate and boron derivative functional groups. To prepare branched or hyperbranched polymers using the process of the invention, in a two monomers system, both aryl monomers should contain at least two reactive triflate or boron derivative groups; in a one monomer system, the monomer should contain at least one of the triflate or boron derivative groups and more than one the other group. The boron derivative functional groups are selected from a boronic acid group represented by $B(OH)_2$, a boronic ester group represented by $B(OR_{12})(OR_{13})$ wherein $R_{12}$ is substituted or unsubstituted alkyl group of 1 to 6 carbons, and $R_{13}$ is hydrogen, or substituted and unsubstituted alkyl group of 1 to 6 carbons, $R_{12}$ and $R_{13}$ can be the same or different, and $R_{12}$ and $R_{13}$ can be connected to form a cyclic boronic ester, preferably a 5- or 6-membered ring; and a borane group represented by $BR_{14}R_{15}$, wherein $R_{14}$ and $R_{15}$ are each substituted and unsubstituted alkyl group of 1 to 20 carbons. The boron derivative groups are preferably boronic acid or cyclic boronic ester groups. Polymers can be prepared by using a mixture of monomers to form copolymers with desired properties and architecture. To prepare linear polymers, the polymerization system preferably includes about equal mole percent of the reactive triflate and boron derivative groups. The mole ratio of these two classes of reactive groups is preferably 0.98 to 1.10, more preferably less than 1.05, most preferably 1.00. If desired, a mono-functional triflate or boron derivative can be used to end-cap the chain ends.

Examples of the aryl groups for the monomers include but are not limited to aromatic hydrocarbons such as phenyl, naphthyl, anthracene, fluorene, benzofluorene, dibenzofluorene, phenanthrene, perylene, pyrene, rubrene, chrysene, tetracene, pentacene, triphenylene, diphenylanthracene, dinapthylanthracene, and benzo[a]pyrene; and heteroaromatic groups such as thiophene, pyrrole, furan, pyridine, triazines, tetrazenes, oxazoles, imidazoles, oxadiazole, thiadiazole, benzoxazole, quinoline, benzimidazole, carbazole, benzothiazole, and acridine; and triarylamines such as triphenylamine, dinaphthylphenylamine, and N,N'-diphenylbenzidine. Preferably, the aryl groups are selected from fluorene, benzofluorene, diphenylanthracene, dinaphthylanthracene, thiophene, oxadiazole, benzothiazole, benzimidazole and carbazole.

The bases suitable for use in the process of the invention include inorganic aqueous bases such as alkali metal hydroxides, carbonates acetates, and bicarbonates, alkaline earth metal hydroxides, carbonates acetates, and bicarbonates, alkaline earth metal alkoxides, and alkali metal alkoxides, and organic bases such as sources of hydroxyl ions and Lewis bases such as those which produce a source of hydroxyl ions in the presence of water. The organic base should be soluble in an organic solvent or water. Examples of aqueous inorganic bases include the hydroxide, carbonates and bicarbonates of lithium, sodium, potassium, cesium, and barium. Preferably, the aqueous base is a solution of sodium, potassium, or cesium carbonate in a concentration of 1 to 2 M. Examples of organic bases include alkyl ammonium hydroxides, carbonates, bicarbonates, fluorides, and borates, pyridines, organic amines. Preferably, the organic base used in the process of the invention is a tetraalkylammonium hydroxide, carbonate, or bicarbonate such as tetramethyl-, tetraethyl-, or tetrapropyl-ammonium hydroxide, carbonate, or bicarbonate. The amount of base used in the process is not particularly important as long as the number of moles of the base is equal or higher than that of the monomer. Preferably, 1 to 10 molar equivalents of the base per boron-derivative functional group are employed. More preferably, 1 to 5 molar equivalents of base are used. Most preferably, 1.5 to 4 molar equivalents, and in particular 1.8 to 2.5 molar equivalents of base are used. A single base or a mixture of different bases can be used in the process of the invention.

The catalyst used in the process of the invention is preferably a palladium catalyst in a form of Pd(0) or Pd(II) complexes with ligands or Pd(II) salts. Examples of the suitable ligands for the palladium complexes are phosphines such as trialkylphophines, tricycloalkylphosphines and triarylphosphines, where the three substituents on the phosphorus can be identical or different and one or more of the ligands can link phosphorus groups of a plurality of phosphines, where part of this linkage can also be one or me metal atoms, diketones such asdibenzylideneacetone (dba), acetylacetone and octafluoroacetylacetone, and tertiary amines such as triethylamine, trimethylamine, tripropylamines. These ligands can also be derivatized by attachment of cationic or anionic groups to render water solubility. It is also possible to use a mixture of more than one ligand. Particular examples of the phosphine ligands used in the process of the invention are trimethylphosphine, tributylphophine, tricyclohexylphosphine, tritolylphosphine, 1,2-bis(diphenyl-phosphino)ethane, triphenylphosphine, 1,3-bis(diphenylphosphino)propane, and 1,1'-(diphenylphosphineo)ferrocene (dppf). Preferably, the ligands are triphenylphosphine ($Ph_3P$), 1,1'-(diphenlphosphineo)ferrocene (dppf), 1,2-bis(diphenylphosphino)ethane, and 1,3-(bisdiphenylphosphino)propane, and more preferably, triphenylphosphine ($Ph_3P$), and 1,1'-(diphenlphosphineo)ferrocene (dppf). The most preferred Pd(0) complex is $Ph(Ph_3P)_4$. The preferred Pd(II) salts are palladium acetate, palladium (II) propionate, palladium (II) butanoate, and palladium (II) chloride, and more preferred Pd (II) salt is palladium (II) acetate. When a palladium (II) salt is used, it is advantageous to add to the reaction mixture 2 to 4 molar equivalents of other ligands such as $Ph_3P$ or dppf per mole of Pd salt. A Pd(II) complex such as $PdCl_2(PPh_3)_2$, bis(acetonitrile)-palladium dichloride, dichlorobis(dimethylsulfoxide) palladium (II), bis(benzonitrile)palladium dichloride, or $PdCl_2(dppf)$ can be used as an alternative. The palladium catalyst can also be on a support material such as an inert organic resin. Typically, the amount of the palladium catalyst used in the reaction mixture is 0.001 to 1 mol % for each mole of monomer, preferably, 0.01 to 1 mol % for each mole of monomer.

The organic solvents suitable for use in the process include those capable of dissolving the monomer to a solution concentration of at least 1 percent, preferably at least 2 percent. Examples of suitable solvents for the process described are hydrocarbons such as hexane, heptane, petroleum ether, cyclohexane, benzene, chlorobenzenes, ethylbenzen, mesitylene, toluene, and xylenes, ethers such as anisole, diethyl ether, tetrahydrofuran, dioxane, dioxolane, diisopropyl ether, dimethoxyethane, t-butyl methyl ether, and diethylene glycol dimethyl ether, ketones such as acetone, methyl ethyl ketone, and isobutyl methyl ketone, alcohols such as methanol, ethanol, propanols, ethylene glycol, and butanols, and amides such as dimethylformamide, dimethylactamide and N-methylpyrrolidone, and the fluorinated analog thereof, and the mixtures thereof.

The preferred organic solvents include one solvent in which the polymer is soluble. Examples of the preferred solvents are ethers such as tetrahydrofuran, dioxane, dimethoxyethane, diethylene glycol dimethyl ether, diisopropyl ether, hydrocarbons such as benzene, chlorobenzenes, toluene, xylenes, heptane, and cyclohexane, ketones such as methyl ethyl ketone and isobutyl methyl ketone, amides such as dimethylformamide, dimethylacetamide and N-methylpyrrolidone, and mixtures thereof.

More preferred organic solvents are ethers, for example tetrahydrofuran, dimethoxyethane and dioxane, hydrocarbons for example toluene, chlorobenzenes, and xylenes, and amides for example, dimethylformamide, and dimethylacetamide.

Most preferred organic solvents of the process of the invention are one or more water-insoluble solvents such as toluene or xylenes or tetrahydrofuran, or mixtures thereof. The volume of the solvent of the process of the invention should be maintained at the level for efficient mixing and stirring at reflux as the reaction mixture becomes more viscous with the build-up of polymer molecular weight.

The polymerization reaction mixture can also contain a phase transfer catalyst as disclosed in U.S. Pat. No. 5,777,070. Suitable phase transfer catalysts used in the process of the invention include quaternary ammonium and phosphonium salts, crown ethers and cryptands. Preferably, the phase transfer catalyst is a tetralkylammonium halide, or bisulfate. Examples of the most preferred phase transfer catalyst are tetrabutylammonium chloride and tricaprylylmethylammonium chloride (known as Aliquat® from Aldrich Chemical). The preferred range of the amount of phase transfer catalyst is between 0.01 to 0.5 mole per mole of monomer, more preferably 0.05 to 0.1 mole per mole of monomer.

The polymerization reaction is carried at a temperature of from 0 to 200° C., preferably from 30 to 170° C., and more preferably 50 to 150° C., and most preferably 60 to 120° C. The reaction time is from 1 to 100 hours, preferably 5 to 70 hours, more preferably 5 to 50 hours, and most preferably, 5 to 48 hours.

The process of the present invention can also be extended to the use of monomers in which some or all of the reactive functional groups are not directly attached to the aromatic rings, especially to other kinds of unsaturated monomers.

The synthetic schemes of the compounds according to the present invention are illustrated in Schemes 1-11.

The process of the invention provides conjugated polymers particularly useful for an optical device. The optical device can comprise a luminescent device such as an EL device in which the polymer or small molecules of the present invention is deposited between a cathode and an anode. The polymers or small molecules or the combination thereof can be deposited as thin film by vapor deposition method or from a solution by spin-coating, spray-coating, dip-coating, roller-coating, or ink jet delivery. The thin film can be supported by substrate directly, preferably a transparent substrate, or supported by the substrate indirectly where there is one or more inter layers between the substrate and thin film. The thin film can be used as emitting layer or charge carrier transporting layer.

General EL Device Architecture

The present invention can be employed in most organic EL device configurations. These include very simple structures comprising a single anode and cathode to more complex devices, such as passive matrix displays comprised of orthogonal arrays of anodes and cathodes to form pixels, and active-matrix displays where each pixel is controlled independently, for example, with thin film transistors (TFTs).

There are numerous configurations of the organic layers wherein the present invention can be successfully practiced. A typical structure is shown in FIG. 1 and includes a substrate 101, an anode 103, a hole-injecting layer 105, a hole-transporting layer 107, a light-emitting layer 109, an electron-transporting layer 111, and a cathode 113. These layers are described in detail below. This figure is for illustration only and the individual layer thickness is not scaled according to the actual thickness. Note that the substrate can alternatively be located adjacent to the cathode, or the substrate can actually constitute the anode or cathode. The organic layers between the anode and cathode are conveniently referred to as the organic EL element. Also, the total combined thickness of the organic layers is preferably less than 500 nm.

The anode and cathode of the OLED are connected to a voltage/current source 250 through electrical conductors 260. The OLED is operated by applying a potential between the anode and cathode such that the anode is at a more positive potential than the cathode. Holes are injected into the organic EL element from the anode and electrons are injected into the organic EL element at the anode. Enhanced device stability can sometimes be achieved when the OLED is operated in an AC mode where, for some time period in the cycle, the potential bias is reversed and no current flows. An example of an AC driven OLED is described in U.S. Pat. No. 5,552,678.

Substrate

The OLED device of this invention is typically provided over a supporting substrate 101 where either the cathode or anode can be in contact with the substrate. The electrode in contact with the substrate is conveniently referred to as the bottom electrode. Conventionally, the bottom electrode is the anode, but this invention is not limited to that configuration. The substrate can either be light transmissive or opaque, depending on the intended direction of light emission. The light transmissive property is desirable for viewing the EL emission through the substrate. Transparent glass or plastic is commonly employed in such cases. The substrate can be a complex structure comprising multiple layers of materials. This is typically the case for active matrix substrates wherein TFTs are provided below the EL layers. It is still necessary that the substrate, at least in the emissive pixilated areas, be comprised of largely transparent materials such as glass or polymers. For applications where the EL emission is viewed through the top electrode, the transmissive characteristic of the bottom support is immaterial, and therefore can be light transmissive, light absorbing or light reflective. Substrates for use in this case include, but are not limited to, glass, plastic, semiconductor materials, silicon, ceramics, and circuit board materials. Again, the substrate can be a complex structure comprising multiple layers of materials such as found in active matrix TFT designs. Of course it is necessary to provide in these device configurations a light-transparent top electrode.

Anode

When EL emission is viewed through anode 103, the anode should be transparent or substantially transparent to the emission of interest. Common transparent anode materials used in this invention are indium-tin oxide (ITO), indium-zinc oxide (IZO) and tin oxide, but other metal oxides can work including, but not limited to, aluminum- or indium-doped zinc oxide, magnesium-indium oxide, and nickel-tungsten oxide. In addition to these oxides, metal nitrides, such as gallium nitride, and metal selenides, such as zinc selenide, and metal sulfides, such as zinc sulfide, can be used as the anode 103. The anode can be modified with plasma-deposited fluorocarbons. For applications where EL emission is viewed only through the cathode electrode, the transmissive characteristics of anode are immaterial and any conductive material can be used, transparent, opaque or reflective. Example conductors for this application include, but are not limited to, gold, iridium, molybdenum, palladium, and platinum. Typical anode materials, transmissive or otherwise, have a work function of 4.1 eV or greater. Desired anode materials are commonly deposited by any suitable way such as evaporation, sputtering, chemical vapor deposition, or electrochemical means. Anodes can be patterned using well-known photolithographic processes. Optionally, anodes can be polished prior to application of other layers to reduce surface roughness so as to reduce shorts or enhance reflectivity.

Hole-Injection Layer (HIL)

Although not always necessary, it is often useful that a hole-injecting layer 105 be provided between anode 103 and hole-transporting layer 107. The hole-injecting material can serve to improve the film formation property of subsequent organic layers and to facilitate injection of holes into the hole-transporting layer. Suitable materials for use in the hole-injecting layer include, but are not limited to, porphyrinic compounds as described in U.S. Pat. No. 4,720,432, plasma-deposited fluorocarbon polymers as described in U.S. Pat. No. 6,208,075, and some aromatic amines, for example, m-MTDATA (4,4',4''-tris[(3-methylphenyl)phenylamino]triphenylamine). Alternative hole-injecting materials reportedly useful in organic EL devices are described in EP 0 891 121 A1 and EP 1 029 909 A1.

Hole-Transporting Layer (HTL)

The hole-transporting layer 107 of the organic EL device in general contains at least one hole-transporting compound such as an aromatic tertiary amine, where the latter is understood to be a compound containing at least one trivalent nitrogen atom that is bonded only to carbon atoms, at least one of which is a member of an aromatic ring. In one form the aromatic tertiary amine can be an arylamine, such as a monoarylamine, diarylamine, triarylamine, or a polymeric arylamine. Exemplary monomeric triarylamines are illustrated by Klupfel, et al., U.S. Pat. No. 3,180,730. Other suitable triarylamines substituted with one or more vinyl radicals or at least one active hydrogen-containing group are disclosed by Brantley, et al. in U.S. Pat. Nos. 3,567,450 and 3,658,520

A more preferred class of aromatic tertiary amines are those which include at least two aromatic tertiary amine moieties as described in U.S. Pat. Nos. 4,720,432 and 5,061,569. Such compounds include those represented by structural Formula (A):

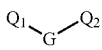
(A)

wherein:
Q₁ and Q₂ are independently selected aromatic tertiary amine moieties; and
G is a linking group such as an arylene, cycloalkylene, or alkylene group of a carbon to carbon bond.

In one embodiment, at least one of $Q_1$ or $Q_2$ contains a polycyclic fused ring structure, e.g., a naphthalene. When G is an aryl group, it is conveniently a phenylene, biphenylene, or naphthalene moiety.

A useful class of triarylamines satisfying structural Formula (A) and containing two triarylamine moieties is represented by structural Formula (B):

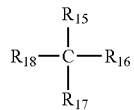
(B)

wherein:
$R_{15}$ and $R_{16}$ each independently represents a hydrogen atom, an aryl group, or an alkyl group or $R_1$ and $R_2$ together represent the atoms completing a cycloalkyl group; and
$R_{17}$ and $R_{18}$ each independently represents an aryl group, which is in turn substituted with a diaryl substituted amino group, as indicated by structural Formula (C):

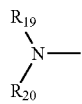
(C)

wherein $R_{19}$ and $R_{20}$ are independently selected aryl groups. In one embodiment, at least one of $R_{19}$ or $R_{20}$ contains a polycyclic fused ring structure, e.g., a naphthalene.

Another class of aromatic tertiary amines is the tetraaryldiamines. Desirable tetraaryldiamines include two diarylamino groups, such as indicated by Formula (C), linked through an arylene group. Useful tetraaryldiamines include those represented by Formula (D):

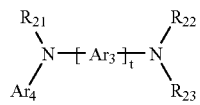
(D)

wherein
each $Ar_3$ is an independently selected arylene group, such as a phenylene or anthracene moiety,
t is an integer of from 1 to 4, and
$Ar_4$, $R_{21}$, $R_{22}$, and $R_{23}$ are independently selected aryl groups.
In a typical embodiment, at least one of $Ar_4$, $R_{21}$, $R_{22}$, and $R_{23}$ is a polycyclic fused ring structure, e.g., a naphthalene.

The various alkyl, alkylene, aryl, and arylene moieties of the foregoing structural Formulae (A), (B), (C), (D), can each in turn be substituted. Typical substituents include alkyl groups, alkoxy groups, aryl groups, aryloxy groups, and halogen such as fluoride, chloride, and bromide. The various alkyl and alkylene moieties typically contain from about 1 to 6 carbon atoms. The cycloalkyl moieties can contain from 3 to about 10 carbon atoms, but typically contain five, six, or seven ring carbon atoms, e.g. cyclopentyl, cyclohexyl, and cycloheptyl ring structures. The aryl and arylene moieties are typically phenyl and phenylene moieties.

The hole-transporting layer can be formed of a single or a mixture of aromatic tertiary amine compounds. Specifically, one can employ a triarylamine, such as a triarylamine satisfying the Formula (B), in combination with a tetraaryldiamine, such as indicated by Formula (D). When a triarylamine is employed in combination with a tetraaryldiamine, the latter is positioned as a layer interposed between the triarylamine and the electron injecting and transporting layer. Illustrative of useful aromatic tertiary amines are the following:
1,1-Bis(4-di-p-tolylaminophenyl)cyclohexane;
1,1-Bis(4-di-p-tolylaminophenyl)-4-phenylcyclohexane;
4,4'-Bis(diphenylamino)quadriphenyl;
Bis(4-dimethylamino-2-methylphenyl)-phenylmethane;
N,N,N-Tri(p-tolyl)amine;
4-(di-p-tolylamino)-4'-[4(di-p-tolylamino)-styryl]stilbene;
N,N,N',N'-Tetra-p-tolyl-4-4'-diaminobiphenyl;
N,N,N',N'-Tetraphenyl-4,4'-diaminobiphenyl;
N,N,N',N'-tetra-1-naphthyl-4,4'-diaminobiphenyl;
N,N,N',N'-tetra-2-naphthyl-4,4'-diaminobiphenyl;
N-Phenylcarbazole;
4,4'-Bis[N-(1-naphthyl)-N-phenylamino]biphenyl;
4,4'-Bis[N-(1-naphthyl)-N-(2-naphthyl)amino]biphenyl;
4,4"-Bis[N-(1-naphthyl)-N-phenylamino]p-terphenyl;
4,4'-Bis[N-(2-naphthyl)-N-phenylamino]biphenyl;
4,4'-Bis[N-(3-acenaphthenyl)-N-phenylamino]biphenyl;
1,5-Bis[N-(1-naphthyl)-N-phenylamino]naphthalene;
4,4'-Bis[N-(9-anthryl)-N-phenylamino]biphenyl;
4,4"-Bis[N-(1-anthryl)-N-phenylamino]-p-terphenyl;
4,4'-Bis[N-(2-phenanthryl)-N-phenylamino]biphenyl;
4,4'-Bis[N-(8-fluoranthenyl)-N-phenylamino]biphenyl;
4,4'-Bis[N-(2-pyrenyl)-N-phenylamino]biphenyl;
4,4'-Bis[N-(2-naphthacenyl)-N-phenylamino]biphenyl;
4,4'-Bis[N-(2-perylenyl)-N-phenylamino]biphenyl;
4,4'-Bis[N-(1-coronenyl)-N-phenylamino]biphenyl;
2,6-Bis(di-p-tolylamino)naphthalene;
2,6-Bis[di-(1-naphthyl)amino]naphthalene;
2,6-Bis[N-(1-naphthyl)-N-(2-naphthyl)amino]naphthalene;
N,N,N',N'-Tetra(2-naphthyl)-4,4"-diamino-p-terphenyl;
4,4'-Bis{N-phenyl-N-[4-(1-naphthyl)-phenyl]amino}biphenyl;
4,4'-Bis[N-phenyl-N-(2-pyrenyl)amino]biphenyl;
2,6-Bis[N,N-di(2-naphthyl)amine]fluorene;
1,5-Bis[N-(1-naphthyl)-N-phenylamino]naphthalene; and
4,4',4"-tris[(3-methylphenyl)phenylamino]triphenylamine.

Another class of useful hole-transporting materials includes polycyclic aromatic compounds as described in EP 1 009 041. Tertiary aromatic amines with more than two amine groups can be used including oligomeric materials. In addition, polymeric hole-transporting materials can be used such as poly(N-vinylcarbazole) (PVK), polythiophenes, polypyrrole, polyaniline (Yang, Y., et al., *Appl. Phys. Lett.* 1994, 64, 1245) and copolymers such as poly(3,4-ethylenedioxythiophene)/poly(4-styrenesulfonate) also called PEDOT/PSS(Groenendaal, L. B., et al., *Adv. Mater.* 2000, 12, 481). Light-Emitting Layer (LEL)

As more fully described in commonly assigned U.S. Pat. Nos. 4,769,292 and 5,935,721, the light-emitting layer (LEL) 109 of the organic EL element includes a luminescent or fluorescent material where electroluminescence is produced as a result of electron-hole pair recombination in this region. The light-emitting layer can be comprised of a single material including both small molecules and polymers, but more commonly includes a host material doped with a guest compound or compounds where light emission comes primarily from the dopant and can be of any color. The host materials in the light-emitting layer can be an electron-transporting material, as defined below, a hole-transporting material, as defined above, or another material or combination of materials that support hole-electron recombination. The dopant is typically chosen from highly fluorescent dyes, but phosphorescent compounds, e.g., transition metal complexes as described in WO 98/55561, WO 00/18851, WO 00/57676, and WO 00/70655 are also useful. Simultaneously, the color of the EL devices can be tuned using dopants of different emission wavelengths. By using a mixture of dopants, EL color characteristics of the combined spectra of the individual dopant are produced. This dopant scheme has been described in considerable detail for EL devices in commonly assigned U.S. Pat. No. 4,769,292 for fluorescent dyes. Dopants are typically coated as 0.01 to 10% by weight into the host material. Polymeric materials such as polyfluorenes and poly(arylene vinylenes), e.g., poly(p-phenylenevinylene), PPV can also be used as the host material. In this case, small molecule dopants can be molecularly dispersed into the polymeric host, or the dopant can be added by copolymerizing a minor constituent into the host polymer.

An important relationship for choosing a dye as a dopant is a comparison of the bandgap potential which is defined as the energy difference between the highest occupied molecular orbital (HOMO) and the lowest unoccupied molecular orbital (LUMO) of the molecule. For efficient energy transfer from the host to the dopant molecule, a necessary condition is that the band gap of the dopant is smaller than that of the host material. For phosphorescent emitters it is also important that the host triplet energy level of the host be high enough to enable energy transfer from host to dopant.

For small molecules, host and emitting molecules known to be of use include, but are not limited to, those disclosed in U.S. Pat. Nos. 4,768,292, 5,141,671, 5,150,006, 5,151,629, 5,405,709, 5,484,922, 5,593,788, 5,645,948, 5,683,823, 5,755,999, 5,928,802, 5,935,720, 5,935,721, and 6,020,078.

For example, small molecule metal complexes of 8-hydroxyquinoline and similar derivatives (Formula E) constitute one class of useful host compounds capable of supporting electroluminescence, and are particularly suitable for light emission of wavelengths longer than 500 nm, e.g. green, yellow, orange, and red

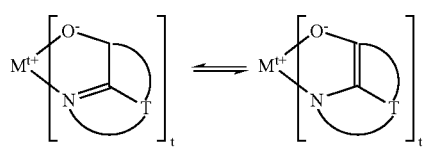

(E)

wherein:
M represents a metal;
t is an integer of from 1 to 4; and
T independently in each occurrence represents the atoms completing a nucleus having at least two fused aromatic rings.

From the foregoing it is apparent that the metal can be monovalent, divalent, trivalent, or tetravalent metal. The metal can, for example, be an alkali metal, such as lithium, sodium, or potassium; an alkaline earth metal, such as magnesium or calcium; an earth metal, such aluminum or gallium, or a transition metal such as zinc or zirconium. Generally any monovalent, divalent, trivalent, or tetravalent metal known to be a useful chelating metal can be employed.

T completes a heterocyclic nucleus containing at least two fused aromatic rings, at least one of which is an azole or azine ring. Additional rings, including both aliphatic and aromatic rings, can be fused with the two required rings, if required. To avoid adding molecular bulk without improving on function the number of ring atoms is typically maintained at 18 or less.

Illustrative of useful chelated oxinoid compounds are the following:
CO-1: Aluminum trisoxine [alias, tris(8-quinolinolato) aluminum(III)];
CO-2: Magnesium bisoxine [alias, bis(8-quinolinolato) magnesium(II)];
CO-3: Bis[benzo{f}-8-quinolinolato]zinc(II);
CO-4: Bis(2-methyl-8-quinolinolato)aluminum(III)-μ-oxo-bis(2-methyl-8-quinolinolato) aluminum(III);
CO-5: Indium trisoxine [alias, tris(8-quinolinolato)indium];
CO-6: Aluminum tris(5-methyloxine) [alias, tris(5-methyl-8-quinolinolato) aluminum(III)];
CO-7: Lithium oxine [alias, (8-quinolinolato)lithium(I)];
CO-8: Gallium oxine [alias, tris(8-quinolinolato)gallium (III)]; and
CO-9: Zirconium oxine [alias, tetra(8-quinolinolato)zirconium(IV)].

Derivatives of 9,10-di-(2-naphthyl)anthracene (Formula F) constitute one class of useful hosts capable of supporting electroluminescence, and are particularly suitable for light emission of wavelengths longer than 400 nm, e.g. blue, green, yellow, orange or red

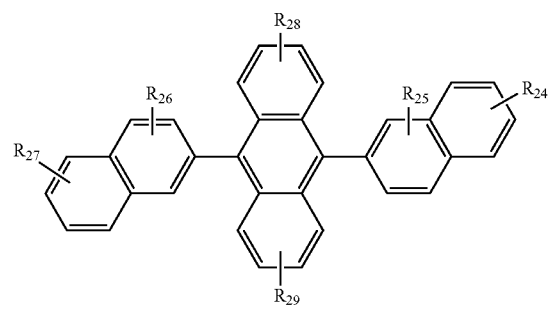

(F)

wherein:
$R_{24}$, $R_{25}$, $R_{26}$, $R_{27}$, $R_{28}$, and $R_{29}$ represent one or more substituents on each ring where each substituent is individually selected from the following groups:
Group 1: hydrogen, or alkyl of from 1 to 24 carbon atoms;
Group 2: aryl or substituted aryl of from 5 to 20 carbon atoms;

Group 3: carbon atoms from 4 to 24 necessary to complete a fused aromatic ring of anthracenyl; pyrenyl, or perylenyl;

Group 4: heteroaryl or substituted heteroaryl of from 5 to 24 carbon atoms as necessary to complete a fused heteroaromatic ring of furyl, thienyl, pyridyl, quinolinyl or other heterocyclic systems;

Group 5: alkoxylamino, alkylamino, or arylamino of from 1 to 24 carbon atoms; and Group 6: fluorine, chlorine, bromine or cyano.

Illustrative examples include 9,10-di-(2-naphthyl)anthracene and 2-t-butyl-9,10-di-(2-naphthyl)anthracene. Other anthracene derivatives can be useful as a host in the LEL, including derivatives of 9,10-bis[4-(2,2-diphenylethenyl)phenyl]anthracene.

Benzazole derivatives (Formula G) constitute another class of useful hosts capable of supporting electroluminescence, and are particularly suitable for light emission of wavelengths longer than 400 nm, e.g. blue, green, yellow, orange or red

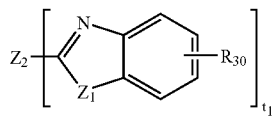

(G)

wherein:
$t_1$ is an integer of 3 to 8;
$Z_1$ is O, $NR_{31}$ or S;
$R_{30}$ and $R_{31}$ are individually hydrogen; alkyl of from 1 to 24 carbon atoms, for example, propyl, t-butyl, heptyl, and the like; aryl or hetero-atom substituted aryl of from 5 to 20 carbon atoms for example phenyl and naphthyl, furyl, thienyl, pyridyl, quinolinyl and other heterocyclic systems; or halo such as chloro, fluoro; or atoms necessary to complete a fused aromatic ring; and
$Z_2$ is a linkage unit including alkyl, aryl, substituted alkyl, or substituted aryl, which conjugately or unconjugately connects the multiple benzazoles together. An example of a useful benzazole is 2,2',2"-(1,3,5-phenylene)tris[1-phenyl-1H-benzimidazole].

Distyrylarylene derivatives are also useful hosts, as described in U.S. Pat. No. 5,121,029. Carbazole derivatives are particularly useful hosts for phosphorescent emitters.

Polymers incorporating the above small molecule moieties as represented by Formulas (E), (F), and (G) are useful host materials. Examples of 9,10-di-(2-naphthyl)anthracene-containing polymers are disclosed in U.S. Pat. No. 6,361,887.

Useful fluorescent dopants (FD) include, but are not limited to, derivatives of anthracene, tetracene, xanthene, perylene, rubrene, coumarin, rhodamine, and quinacridone, dicyanomethylenepyran compounds, thiopyran compounds, polymethine compounds, pyrilium and thiapyrilium compounds, fluorene derivatives, periflanthene derivatives, indenoperylene derivatives, bis(azinyl)amine boron compounds, bis(azinyl)methane compounds, and carbostyryl compounds. Useful phosphorescent dopants (PD) include but are not limited to organometallic complexes of transition metals of iridium, platinum, palladium, or osmium. Illustrative examples of useful dopants include, but are not limited to, the following:

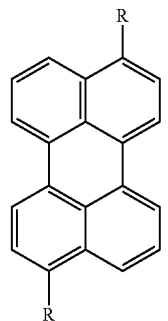

FD 1 R = H
FD 2 R = CO$_2$Pr-i

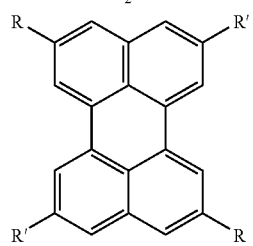

FD 3 R = H, R' = t-Bu
FD 4 R = R' = t-Bu

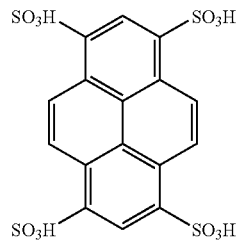

FD 5

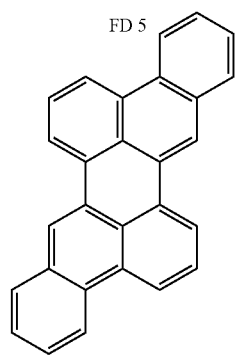

FD 6

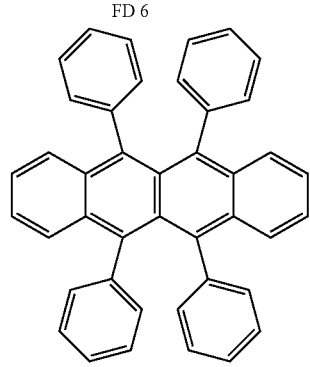

FD 7

-continued

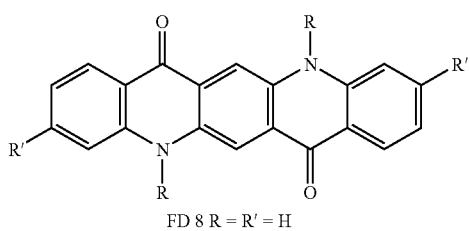

FD 8 R = R' = H
FD 9 R = Me, R' = H
FD 10 R = Pr-i, R' = H
FD 11 R = Me, R' = F
FD 12 R = phenyl, R' = H

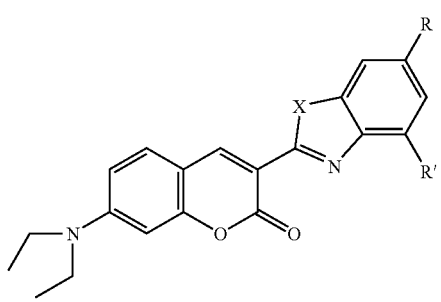

FD 13 R = R' = H, X = O
FD 14 R = H, R' = Me, X = O
FD 15 R = Me, R' = H, X = O
FD 16 R = Me, R' = Me, X = O
FD 17 R = H, R' = t-Bu, X = O
FD 18 R = t-Bu, R' = H, X = O
FD 19 R = R' = t-Bu, X = O
FD 20 R = R' = H, X = S
FD 21 R = H, R' = Me, X = S
FD 22 R = Me, R' = H, X = S
FD 23 R = Me, R' = Me, X = S
FD 24 R = H, R' = t-Bu, X = S
FD 25 R = t-Bu, R' = H, X = S
FD 26 R = R' = t-Bu, X = S

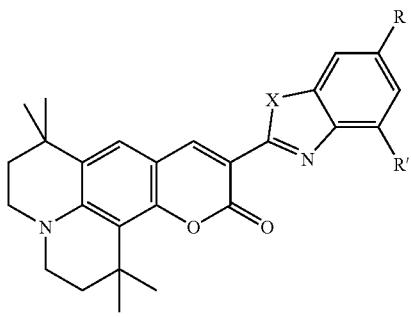

FD 27 R = R' = H, X = O
FD 28 R = H, R' = Me, X = O
FD 29 R = Me, R' = H, X = O
FD 30 R = Me, R' = Me, X = O
FD 31 R = H, R' = t-Bu, X = O
FD 32 R = t-Bu, R' = H, X = O
FD 33 R = R' = t-Bu, X = O
FD 34 R = R' = H, X = S
FD 35 R = H, R' = Me, X = S
FD 36 R = Me, R' = H, X = S
FD 37 R = Me, R' = Me, X = S
FD 38 R = H, R' = t-Bu, X = S
FD 39 R = t-Bu, R' = H, X = S
FD 40 R = R' = t-Bu, X = S

-continued

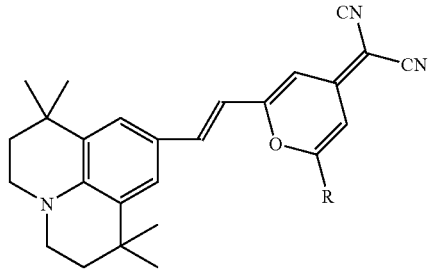

FD 41 R = phenyl
FD 42 R = Me
FD 43 R = t-Bu
FD 44 R = mesityl

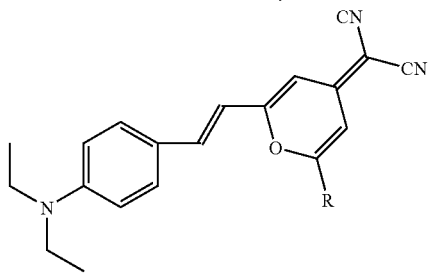

FD 45 R = phenyl
FD 46 R = Me
FD 47 R = t-Bu
FD 48 R = mesityl

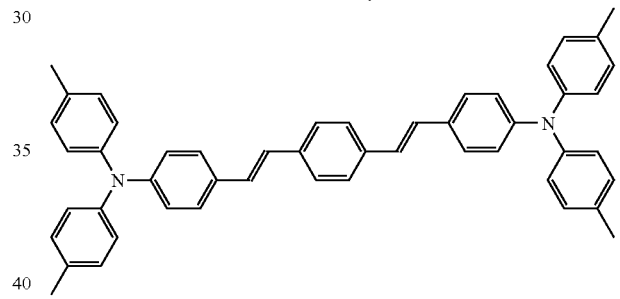

FD 49

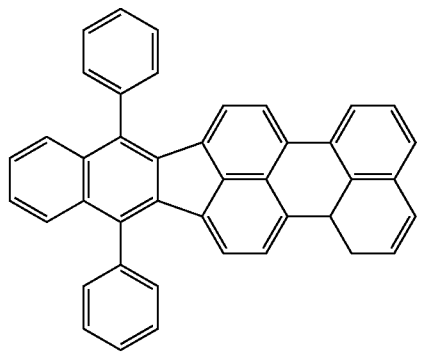

FD 50

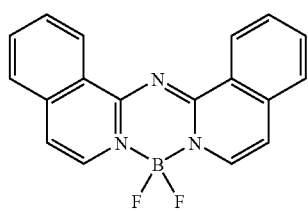

FD 51

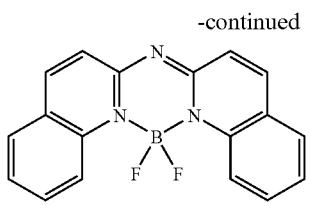

FD 52

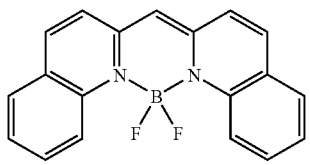

FD 53

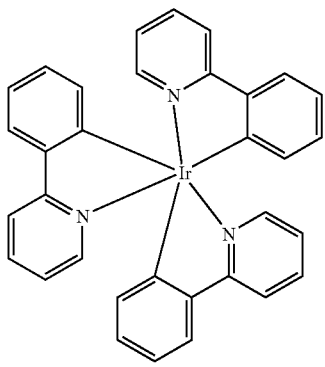

PD 1

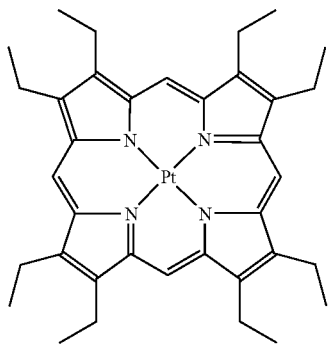

PD 2

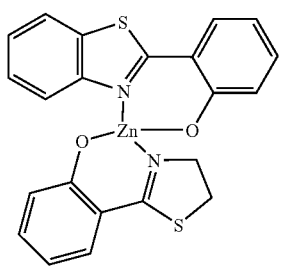

PD 3

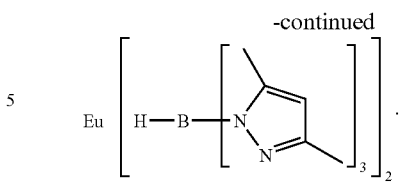

PD 4

Electron-Transporting Layer (ETL)

Preferred thin film-forming materials for use in forming the electron-transporting layer 111 of the organic EL devices of this invention are metal chelated oxinoid compounds, including chelates of oxine itself (also commonly referred to as 8-quinolinol or 8-hydroxyquinoline). Such compounds help to inject and transport electrons and exhibit both high levels of performance and are readily fabricated in the form of thin films. Exemplary of contemplated oxinoid compounds are those satisfying structural Formula (E), previously described.

Other electron-transporting materials include various butadiene derivatives as disclosed in U.S. Pat. No. 4,356,429 and various heterocyclic optical brighteners as described in U.S. Pat. No. 4,539,507. Benzazoles satisfying structural Formula (G) are also useful electron transporting materials. Triazines are also known to be useful as electron transporting materials. Oxadiazole compounds including small molecules and polymers are useful electron transporting materials as described in U.S. Pat. No. 6,451,457.

Cathode

When light emission is viewed solely through the anode, the cathode 113 used in this invention can be comprised of nearly any conductive material. Desirable materials have effective film-forming properties to ensure effective contact with the underlying organic layer, promote electron injection at low voltage, and have effective stability. Useful cathode materials often contain a low work function metal (<4.0 eV) or metal alloy. One preferred cathode material is comprised of a Mg:Ag alloy wherein the percentage of silver is in the range of 1 to 20%, as described in commonly assigned U.S. Pat. No. 4,885,211. Another suitable class of cathode materials includes bilayers comprising a thin electron-injection layer (EIL) in contact with the organic layer (e.g., ETL), which is capped with a thicker layer of a conductive metal. Here, the EIL preferably includes a low work function metal or metal salt, and if so, the thicker capping layer does not need to have a low work function. One such cathode is comprised of a thin layer of LiF followed by a thicker layer of Al as described in commonly assigned U.S. Pat. No. 5,677,572. Other useful cathode material sets include, but are not limited to, those disclosed in commonly assigned U.S. Pat. Nos. 5,059,861, 5,059,862, and 6,140,763.

When light emission is viewed through the cathode, the cathode should be transparent or nearly transparent. For such applications, metals should be thin or one should use transparent conductive oxides, or including these materials. Optically transparent cathodes have been described in more detail in U.S. Pat. Nos. 4,885,211, 5,247,190, 5,703,436, 5,608,287, 5,837,391, 5,677,572, 5,776,622, 5,776,623, 5,714,838, 5,969,474, 5,739,545, 5,981,306, 6,137,223, 6,140,763, 6,172,459, 6,278,236, 6,284,3936, EP 1 076 368, and JP 3,234,963. Cathode materials are typically deposited by evaporation, sputtering, or chemical vapor deposition.

When needed, patterning can be achieved through many well known methods including, but not limited to, through-mask deposition, integral shadow masking as described in U.S. Pat. No. 5,276,380 and EP 0 732 868, laser ablation, and selective chemical vapor deposition.

Other Useful Organic Layers and Device Architecture

In some instances, layers 109 and 111 can optionally be collapsed into a single layer that serves the function of supporting both light emission and electron transportation. Alternatively, layers 107, 109 and 111 can optionally be collapsed into a single layer that serves the function of supporting both light emission and hole and electron transportation. This is the preferred EL device structure of this invention and is referred to as "single-layer" device.

It also known in the art that emitting dopants can be added to the hole-transporting layer, which can serve as a host. Multiple dopants can be added to one or more layers in order to produce a white-emitting EL device, for example, by combining blue- and yellow-emitting materials, cyan- and red-emitting materials, or red-, green-, and blue-emitting materials. White-emitting devices are described, for example, in EP 1 187 235, EP 1 182 244, U.S. patent application Publication 2002/0025419 A1, and U.S. Pat. Nos. 5,683,823, 5,503,910, 5,405,709, and 5,283,182.

Additional layers such as electron or hole-blocking layers as taught in the art can be employed in devices of this invention. Hole-blocking layers are commonly used to improve efficiency of phosphorescent emitter devices, for example, as in U.S. patent application Publication 2002/0015859 A1.

This invention can be used in so-called stacked device architecture, for example, as taught in U.S. Pat. Nos. 5,703,436 and 6,337,492.

Deposition of Organic Layers

The organic materials comprise a complex fluorene structure of the present invention can be used as host, dopant, charge transporting material, charge blocking material, or combination thereof.

The organic materials mentioned above can be deposited as high quality transparent thin films by various methods such as a vapor deposition or sublimation method, an electron-beam method, a sputtering method, a thermal transferring method, a molecular lamination method and a coating method such as solution casting, spin-coating or inkjet printing, with an optional binder to improve film formation. If the material is a polymer, solvent deposition is typically preferred. The material to be deposited by sublimation can be vaporized from a sublimator "boat" often comprised of a tantalum material, e.g., as described in U.S. Pat. No. 6,237,529, or can be first coated onto a donor sheet and then sublimed in closer proximity to the substrate. Layers with a mixture of materials can use separate sublimator boats or the materials can be pre-mixed and coated from a single boat or donor sheet. Patterned deposition can be achieved using shadow masks, integral shadow masks (U.S. Pat. No. 5,294,870), spatially defined thermal dye transfer from a donor sheet (U.S. Pat. Nos. 5,688,551, 5,851,709, and 6,066,357), and inkjet method (U.S. Pat. No. 6,066,357).

Preferably, the spin-coating or inkjet printing technique is used to deposit the organic material of the invention, only one compound is deposited in a single layer device.

Encapsulation

Most organic EL devices are sensitive to moisture or oxygen, or both, so they are commonly sealed in an inert atmosphere such as nitrogen or argon, along with a desiccant such as alumina, bauxite, calcium sulfate, clays, silica gel, zeolites, alkaline metal oxides, alkaline earth metal oxides, sulfates, or metal halides and perchlorates. Methods for encapsulation and desiccation include, but are not limited to, those described in U.S. Pat. No. 6,226,890. In addition, barrier layers such as SiOx, Teflon, and alternating inorganic/polymeric layers are known in the art for encapsulation.

Optical Optimization

Organic EL devices of this invention can employ various well-known optical effects in order to enhance its properties if desired. This includes optimizing layer thicknesses to yield maximum light transmission, providing dielectric mirror structures, replacing reflective electrodes with light-absorbing electrodes, providing anti glare or antireflection coatings over the display, providing a polarizing medium over the display, or providing colored, neutral density, or color conversion filters over the display. Filters, polarizers, and anti-glare or antireflection coatings can be specifically provided over the cover or as part of the cover.

EXAMPLES

The invention and its advantages are further illustrated by the following specific examples:

Synthesis of Small Molecules

The monomers to be used in the present invention to construct polymers are not necessary to be particularly restricted. Any monomers can be used as long as the polymer formed is a polymer that satisfies the general Formulas (V) and (VI). Typical synthesis is illustrated in Schemes 1-9.

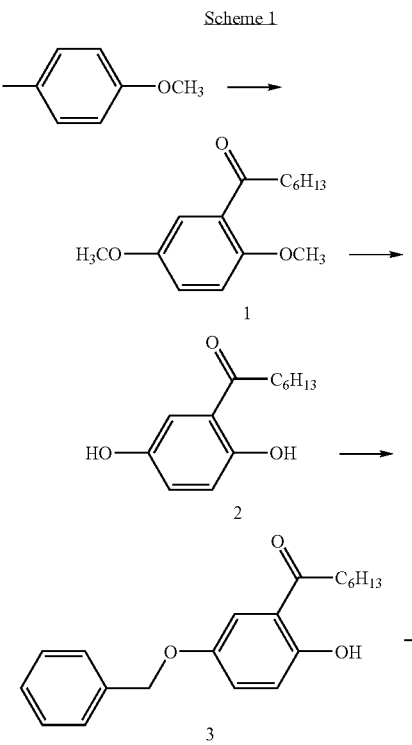

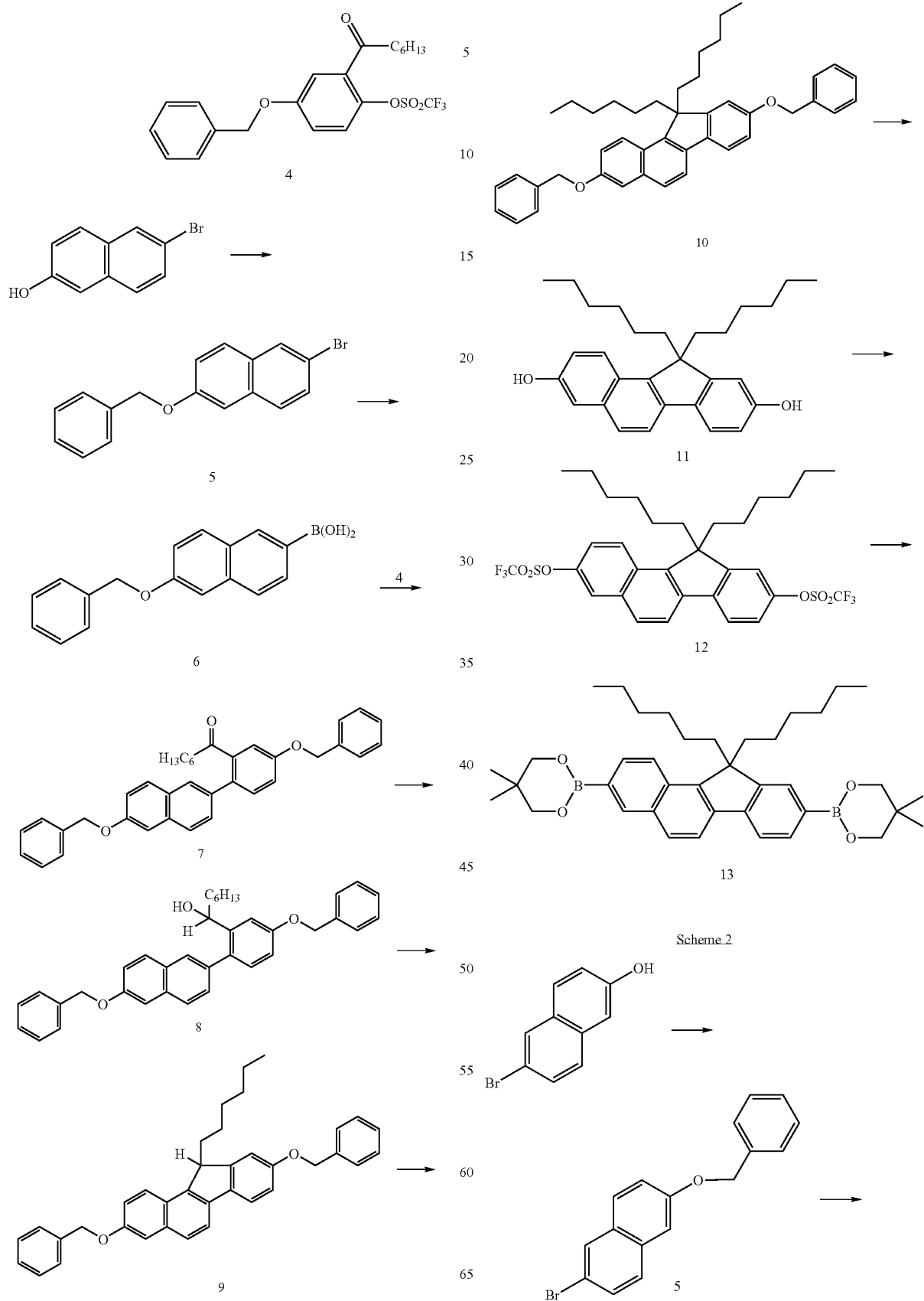

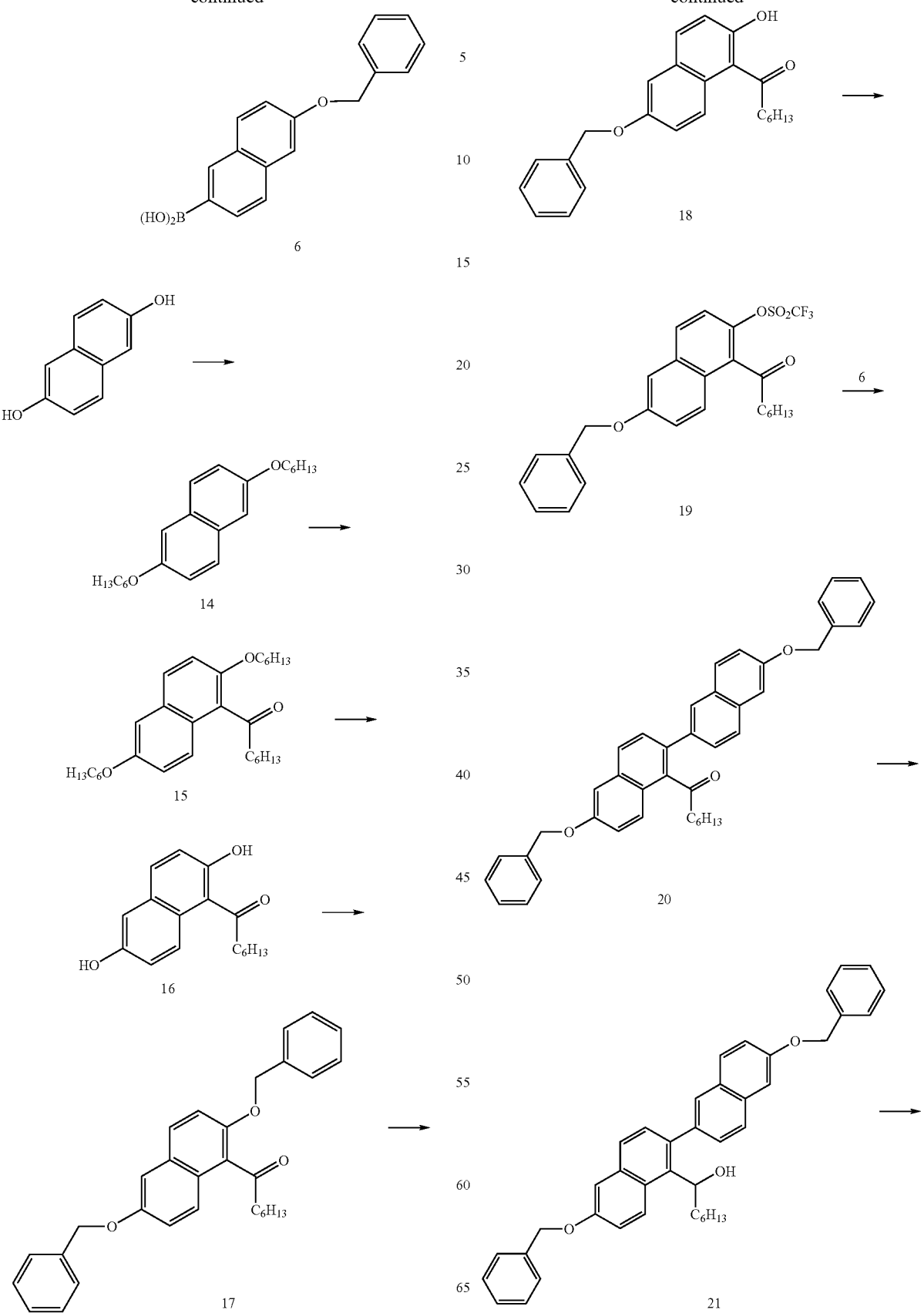

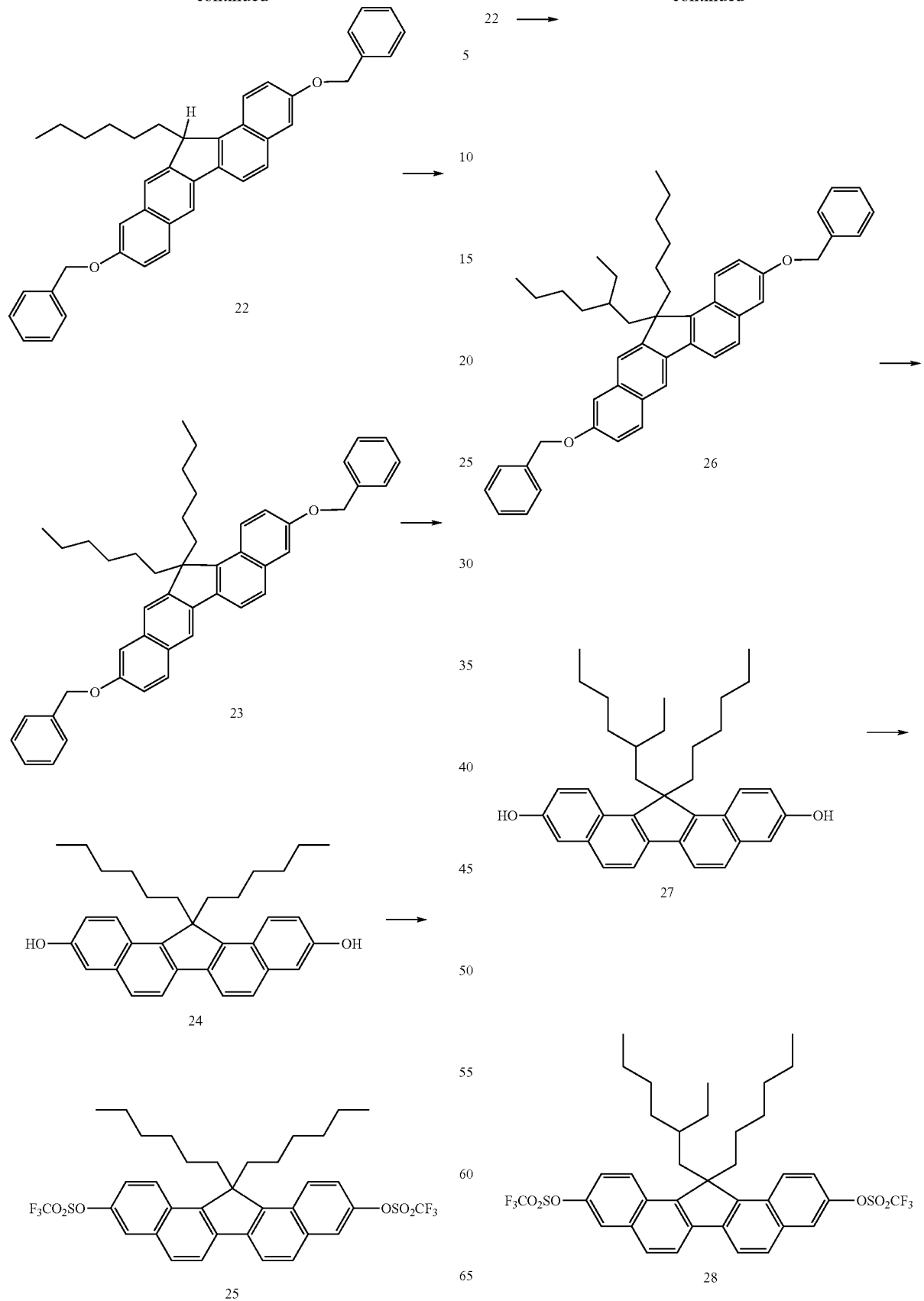

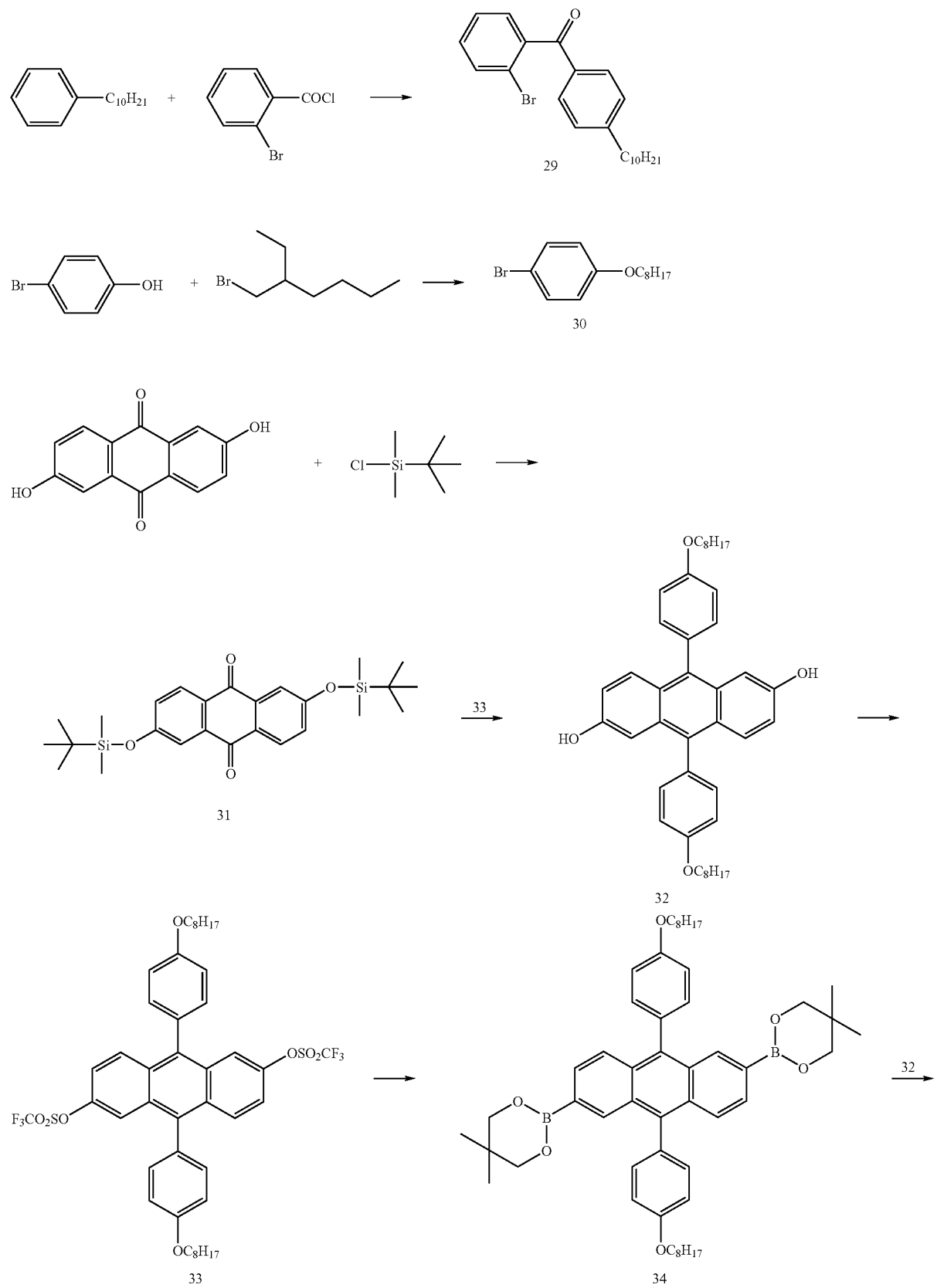
Scheme 3

-continued
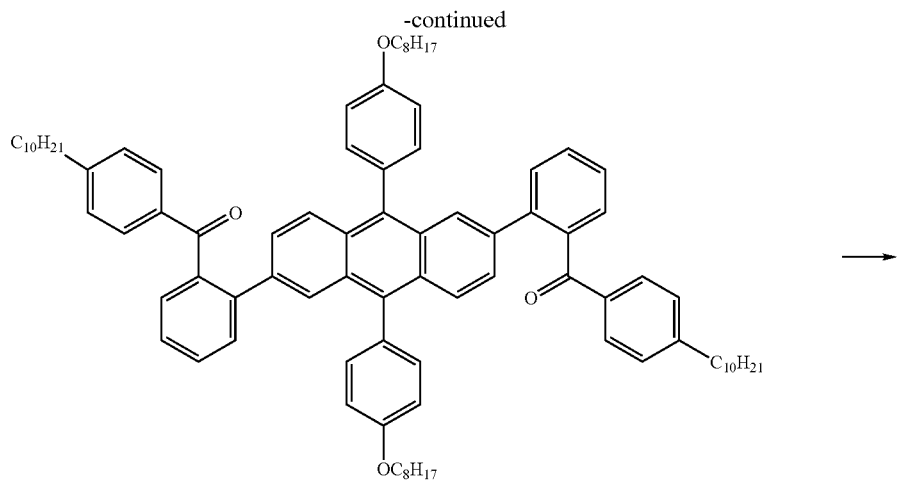
35
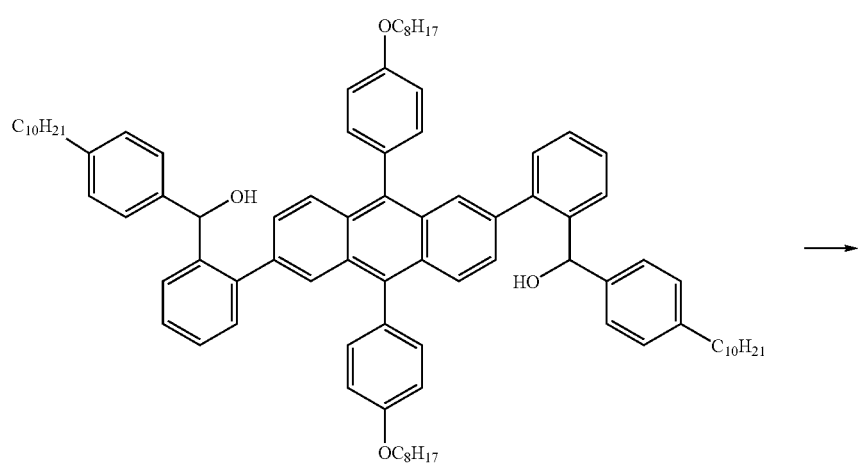
36
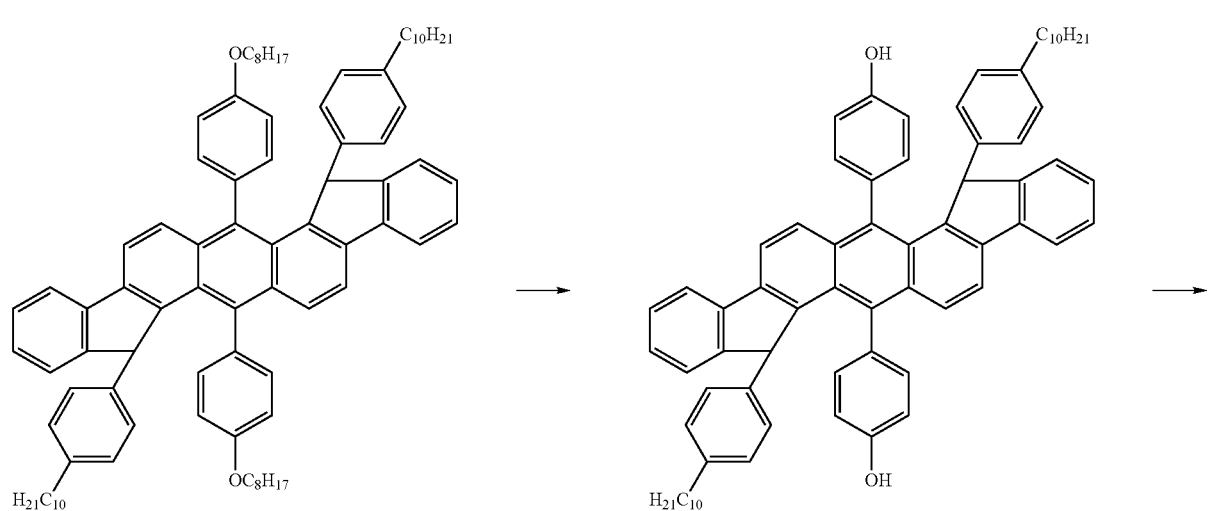
37                                    38

-continued
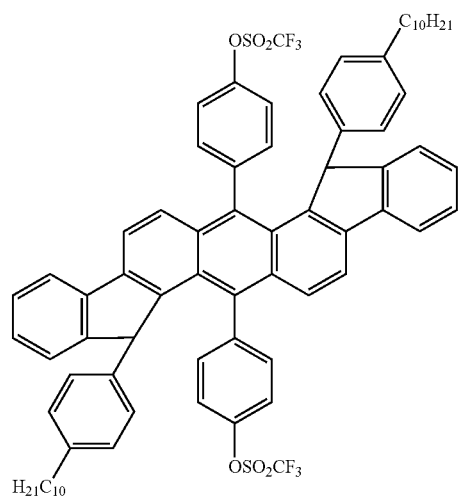
39
Scheme 4
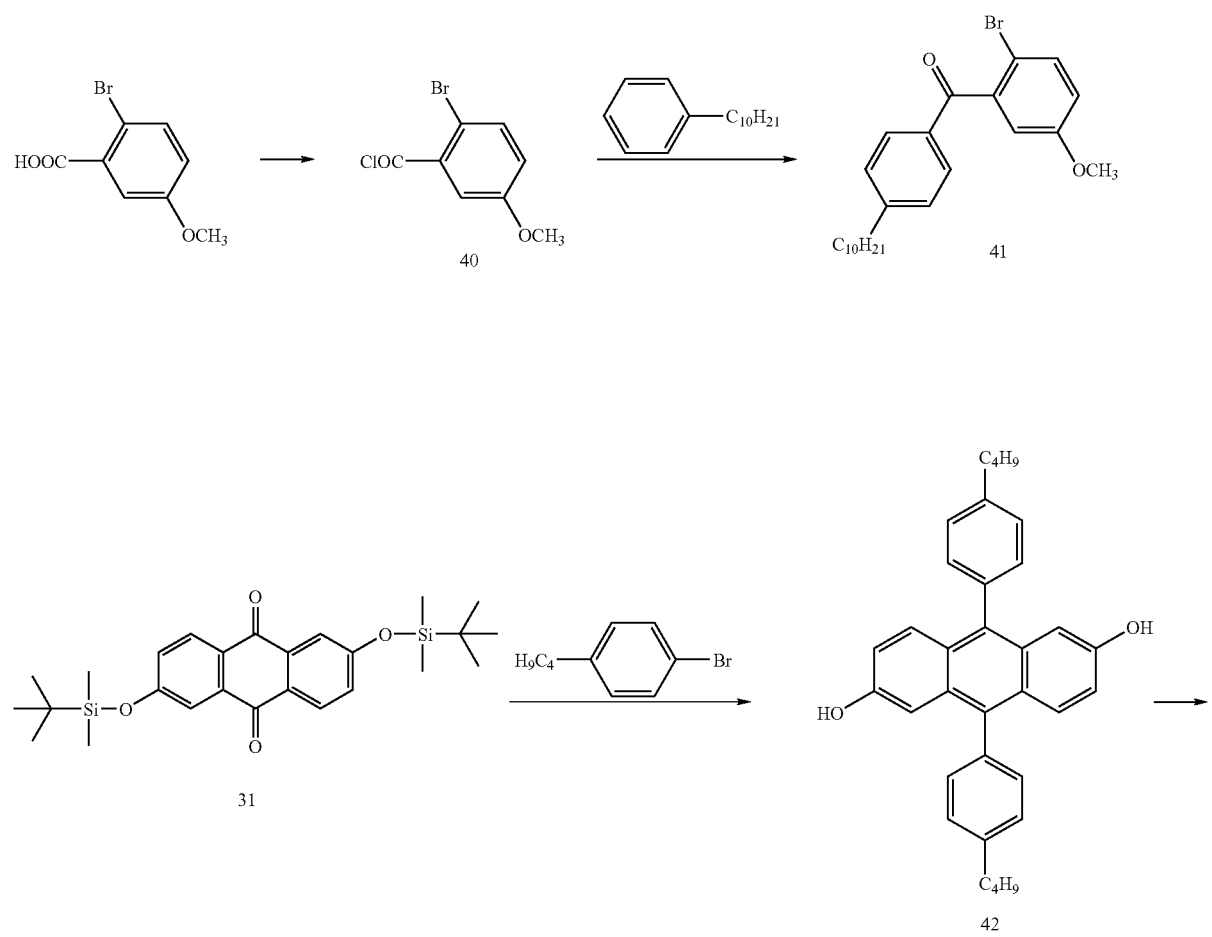

-continued
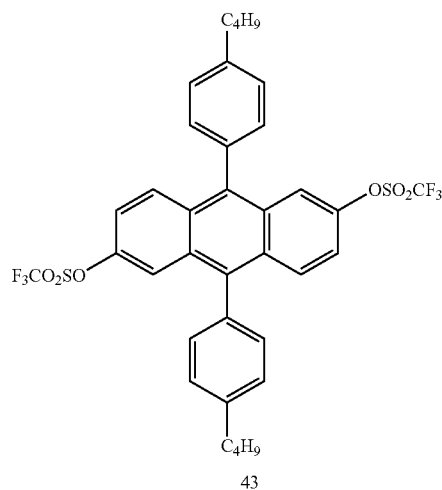
43
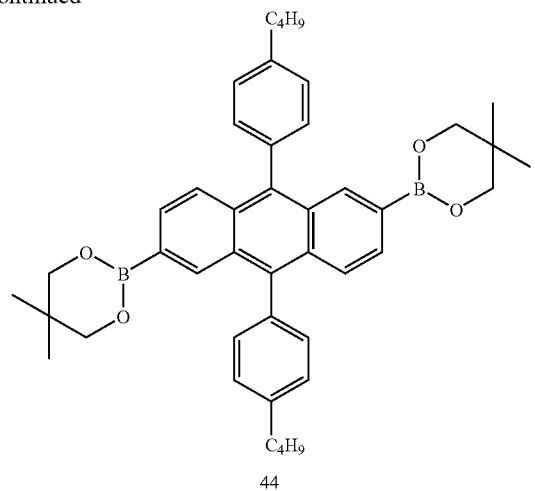
44
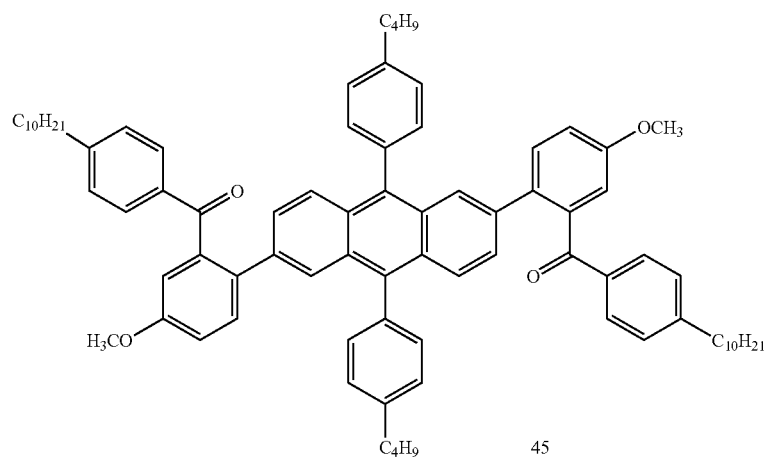
45
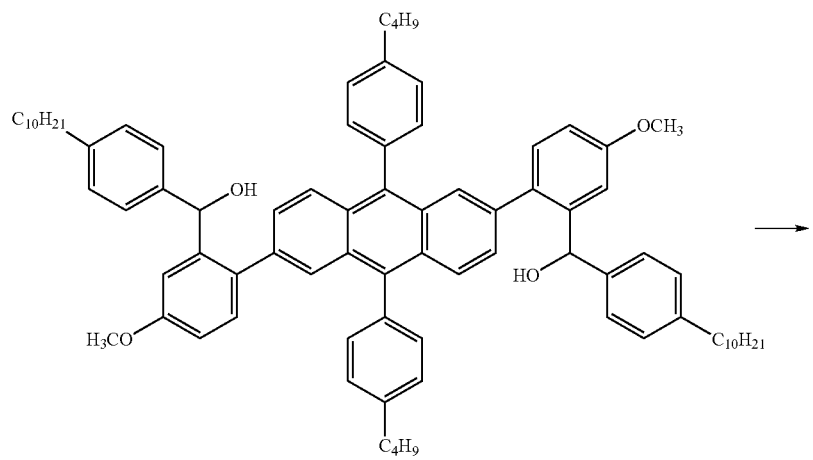
46

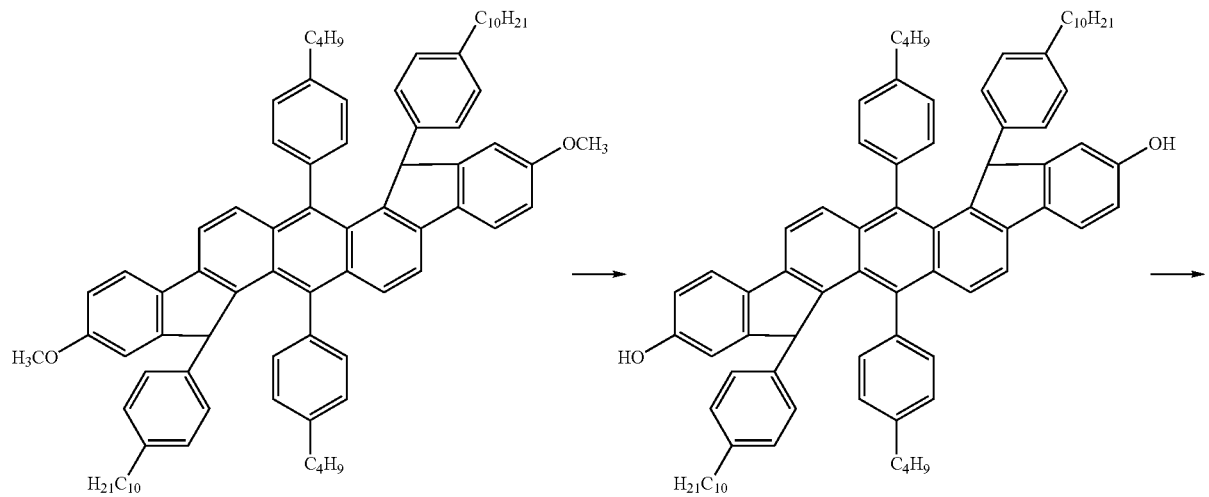
47
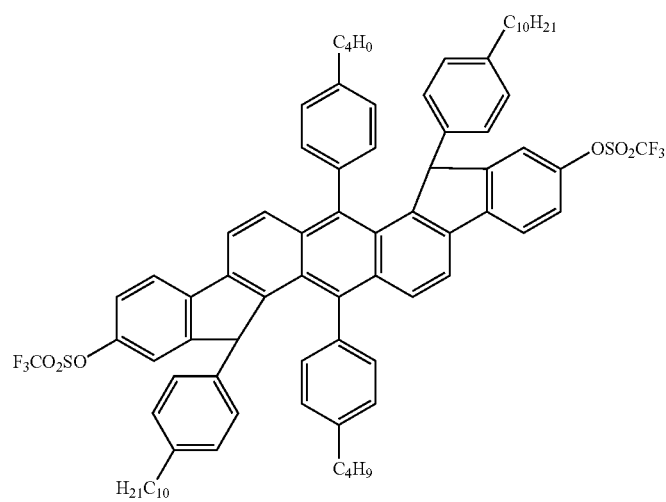
49
Scheme 5
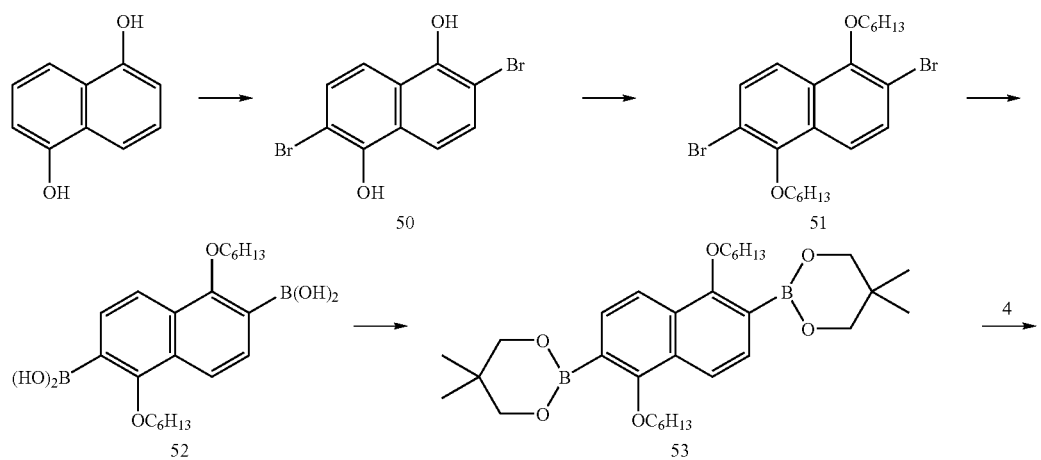

-continued
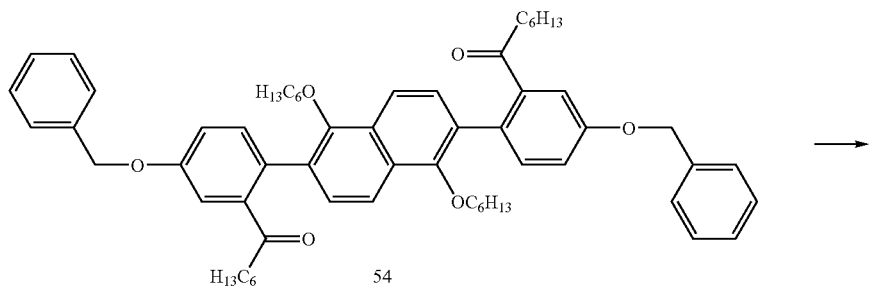
54
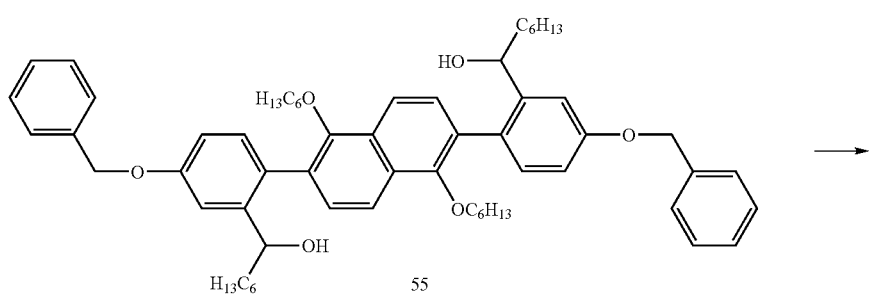
55
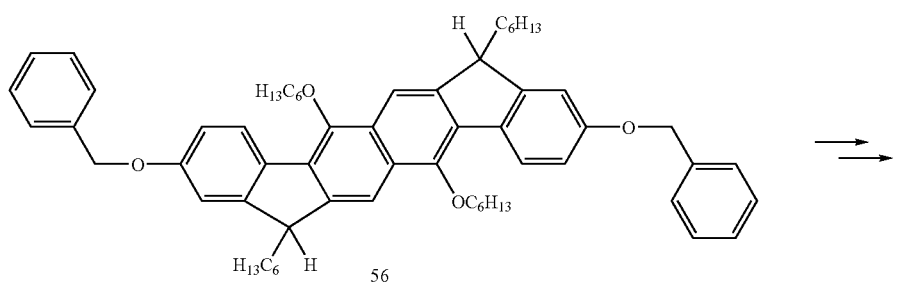
56
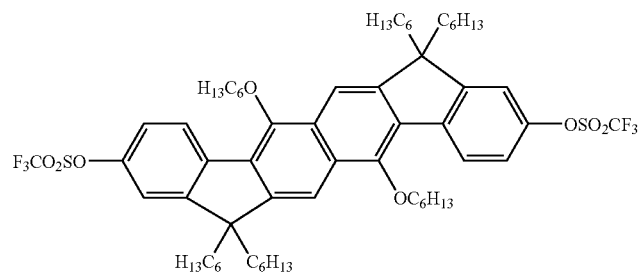
Scheme 6
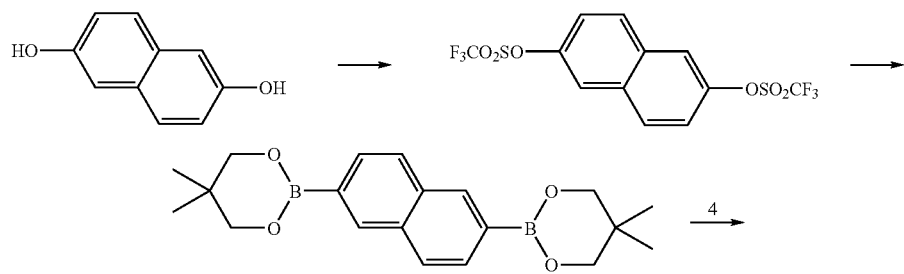

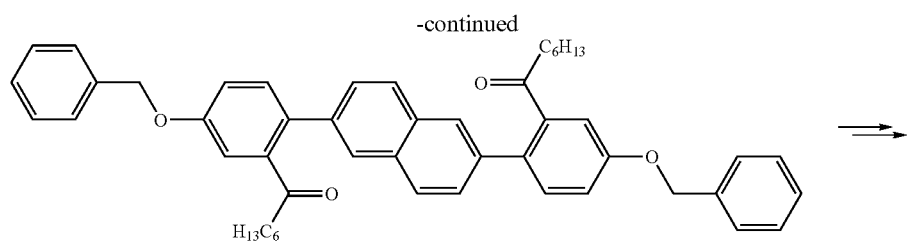
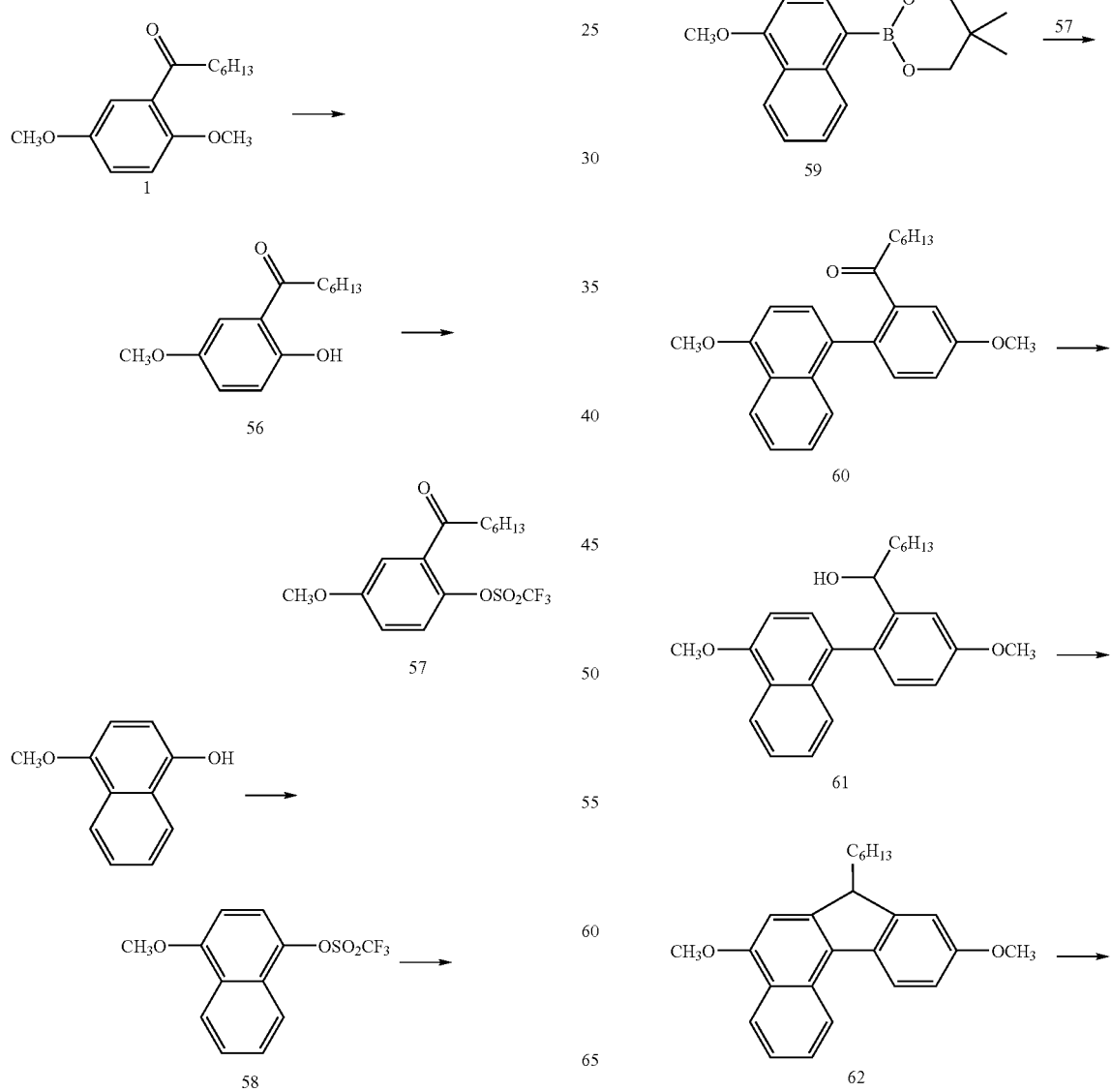
Scheme 7

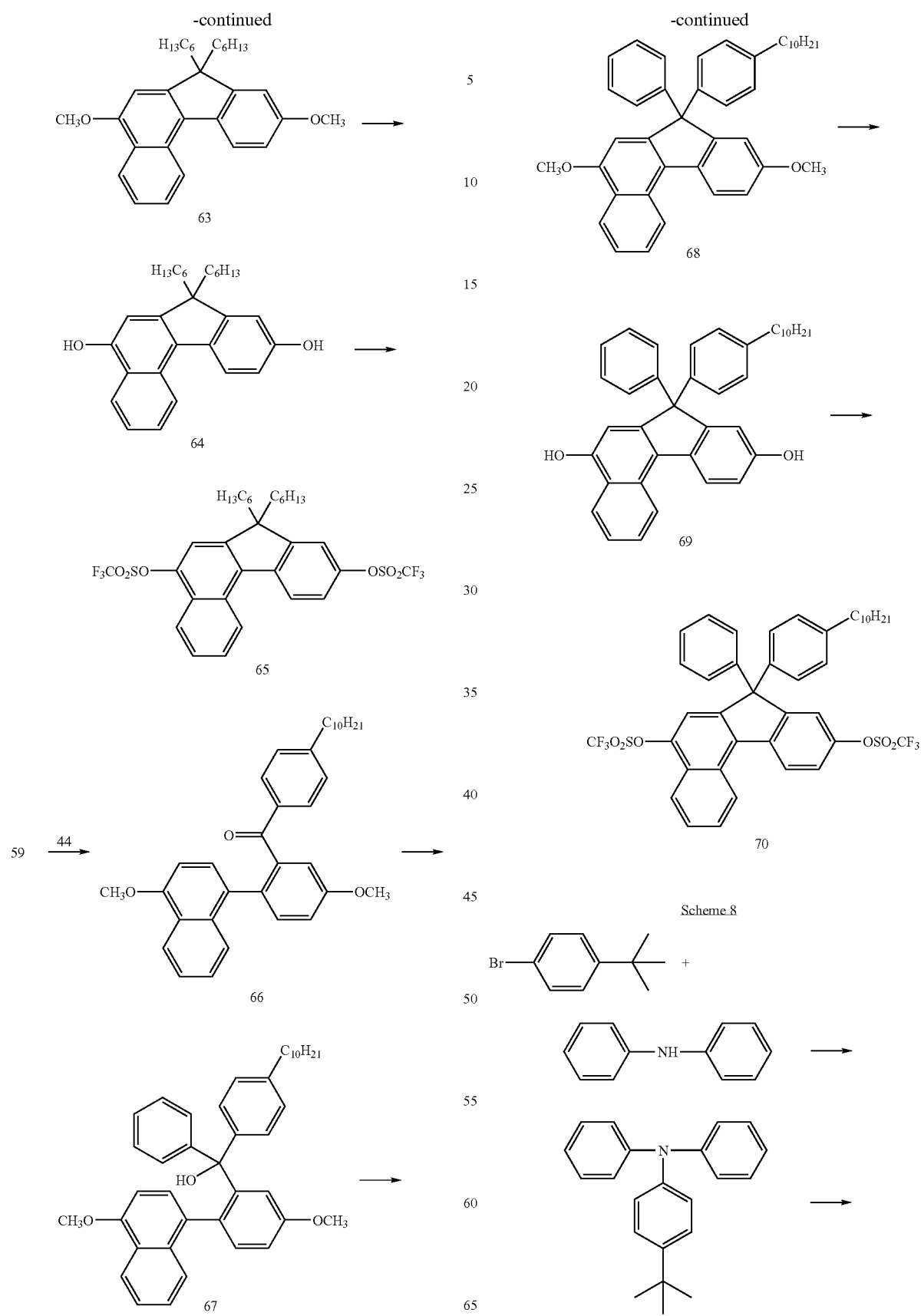

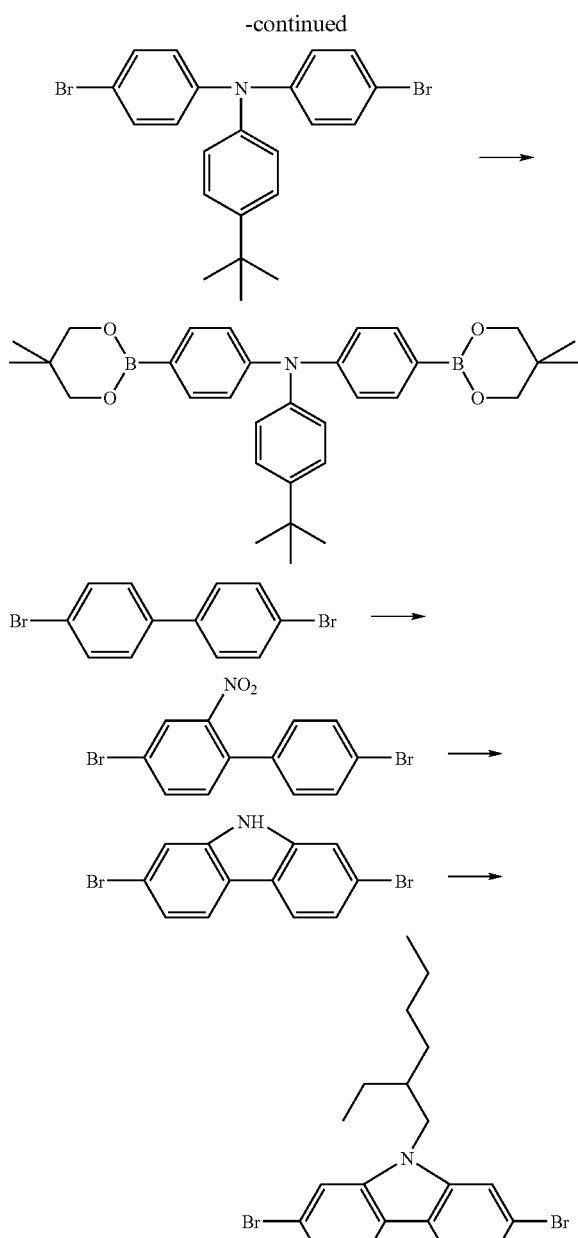

Scheme 9

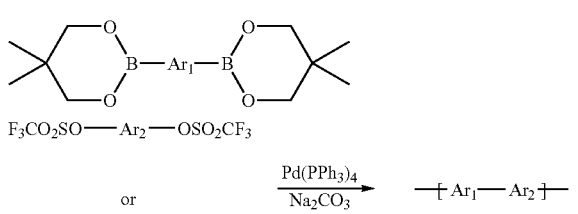

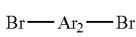

Example 1

Synthesis of Compound 1 (2,5-dimethoxy-heptanophenone)

1,4-Dimethoxybenzene (15.0 g, 0.11 mol) was dissolved in 100 mL of methylene chloride and the solution was cooled to 0° C. To the solution was added aluminum chloride (17.37 g, 0.13 mol) in portions and the mixture was stirred for 10 min. Heptanoyl chloride (17.75 g, 0.12 mol) was added via an additional funnel. After 2 h, reaction was complete and was quenched with dilute HCl solution carefully. The organic phase was separated, washed with dilute sodium bicarbonate, and dried over magnesium sulfate. The crude product was purified by column on silica gel using either/heptane (10/90) as an eluent to give 20.52 g pure product as clear oil (75% yield). FD-MS: 250 ($M^+$).

Example 2

Synthesis of Compound 2 (2,5-dihydroxy-heptanophenone)

Compound 1 (10.0 g, 0.040 mol) was dissolved in 150 mL of toluene. To this solution was added aluminum chloride (11.72 g, 0.088 mol) in portions. The reaction was heated to 80° C. overnight. After cooled to room temperature, the reaction was poured into dilute HCl solution. The organic phase was separated and the aqueous phase was extracted with methylene chloride. The combined organic phase was dried over magnesium sulfate. The crude product was purified by recrystallization from hexane/ethyl acetate to give 6.42 g of pure product as yellow fluffy solid (72% yield). $^1$H NMR (CDCl$_3$) δ ppm: 0.89 (t, J=6.6 Hz, 3 H), 1.28-1.39 (m, 6 H), 1.67-1.76 (m, 2 H), 2.91 (t, J=7.5Hz, 2 H), 5.37 (br, 1 H), 6.87 (d, J=8.9 Hz, 1 H), 7.03 (dd, $J_1$=8.9 Hz, $J_2$=3.0 Hz, 1 H), 7.22 (d, J=3.0 Hz, 1 H), 12.06 (s, 1 H); FD-MS: 222 ($M^+$).

Example 3

Synthesis of Compound 3 (5-benyloxy2-hydroxy-heptanophenone)

Compound 2 (53.60 g, 0.24 mol) was dissolved in 500 mL of acetone. To this solution was added anhydrous potassium carbonate (36.66 g, 0.26 mol). The mixture was stirred for 10 min and benzyl bromide (45.37 g, 0.26 mol) was added dropwise. The reaction was refluxed overnight. After cooled to room temperature, the reaction was filtered and acetone was evaporated. The residue was extracted with ether and dried over magnesium sulfate. The crude product was purified by column on silica gel using heptane/ethyl acetate (98/2) as an eluent. The product was obtained as light yellow solid after further recrystallization from heptane, 50.12 g (0.67% yield). $^1$H NMR (CDCl$_3$) δ ppm: 0.90 (t, J=6.6 Hz, 3 H), 1.32-1.39 (m, 6H), 1.64-1.71 (m, 2 H), 2.88 (t, J=7.5Hz, 2 H), 5.03 (s, 2 H), 6.91 (d, J=9.0 Hz, 1 H), 7.15 (dd, $J_1$=9.0 Hz, $J_2$=3.0 Hz, 1 H), 7.25 (d, J=3.0 Hz, 1 H), 7.32-7.43 (m, 5 H), 11.99 (s, 1 H); FD-MS: 222 ($M^+$).

Example 4

Synthesis of Compound 4

Compound 3 (50.0 g, 0.16 mol) was dissolved in methylene chloride and cooled to 0° C. To the solution was added triethylamine (19.4 g, 0.19 mol), followed by slow addition of triflate anhydride (54.2 g, 0.19 mol). The mixture was stirred at room temperature for a few hours until the completion of the reaction. The reaction was quenched with water, extracted with methylene chloride and dried over $MgSO_4$. The crude product was recrystallized passed through a short pad of silica gel and recrystallized from heptane to give 55.0 g pure product as fluffy white powder (77% yield). FD-MS: 444 ($M^+$).

Example 5

Synthesis of Compound 5
(2-bromo-6-benzyloxynaphthalene)

6-Bromo-2-naphthol (50.0 g, 0.22 mol) was dissolved in 150 mL of DMF, and potassium carbonate (123.92 g, 0.90 mol) was added. The mixture was stirred for 10 min and benzyl bromide (95.84 g, 0.56 mol) was added. The reaction mixture was heated at 90° C. for 4 h and poured into water. The crude product was collected as yellow powder and was purified by recrystallization from ethanol to give 68.05 g pure product as sparklingly white needles (97% yield). $^1$H NMR ($CDCl_3$) δ ppm: 5.17 (s, 2 H), 7.18 (d, J=2.4 Hz, 1 H), 7.25 (dd, $J_1$=8.9 Hz, $J_2$=2.5 Hz, 1 H), 7.35-7.52 (m, 6H), 7.60 (d, J=8.8 Hz, 1 H), 7.67 (d, J=8.9 Hz, 1 H), 7.92 (d, J=1.6 Hz, 1 H); $^{13}$C NMR ($CDCl_3$): 70.08, 107.09, 109.74, 117.15, 120.08, 127.56, 128.11, 128.42, 128.55, 128.64, 129.62, 130.09, 132.96, 136.57; FD-MS: 313 ($M^+$).

Example 6

Synthesis of Compound 6
(6-benzyloxy-2-naphalene boronic acid)

Compound 5 (15.65 g, 0.050 mol) was dissolved in 200 mL of anhydrous THF and cooled to −78° C. To the cold solution was added dropwise n-BuLi (30 mL, 2.5 M in hexane, 0.075 mol) to maintain the temperature lower than −60° C. After one hour, trimethylborate (10.39 g, 0.10 mol) was added and the reaction was stirred for 3 h. The reaction was quenched by dilute HCl, stirred at room temperature for 1 h, and extracted with methylene chloride. The organic phase was dried over $MgSO_4$ and concentrated. The crude product was recrystallized from toluene to give light gray solid that was recrystallized again in methanol to remove the insoluble by-product. The pure product was concentrated from the filtrate as white solid, 6.1 g (44% yield). FD-MS: 278 ($M^+$).

Example 7

Synthesis of Compound 7

Compound 4 (24.16 g, 0.054 mol) and compound 6 (13.60 g, 0.049 mol) were dissolved in 100 mL of toluene and 2 M solution of $Na_2CO_3$ (36 mL, 0.072 mol) and a few drops of phase transfer reagent Aquat® 336 were added. The mixture was bubbled with nitrogen for 10 min and catalyst tetrakis (triphenylphosphine) palladium (0.85 g, 1.5 mol %) was added. The reaction was heated to 105° C. for 3 h. After cooled down, the organic phase was separated and the aqueous phase was extracted with methylene chloride. The combined organic phase was dried over $MgSO_4$. The crude product was recrystallized twice from heptane to give 15.13 g of pure product as white powder (58% yield). $^1$H NMR ($CDCl_3$) δ ppm: 0.73 (t, J=7.2 Hz, 3 H), 0.92-0.97 (m, 4H), 1.04-1.10 (m, 2 H), 1.35-1.40 (m, 2 H), 2.22 (t, J=7.4 Hz, 2 H), 5.15 (s, 2 H), 5.21 (s, 2 H), 7.11-7.16 (m, 2 H), 7.26-7.52 (m, 14H), 7.67 (d, J=1.3 Hz, 1 H), 7.76 (d, J=8.4 Hz, 2 H); $^{13}$C NMR ($CDCl_3$): 14.04, 22.36, 24.56, 28.59, 31.35, 42.92, 70.06, 70.24, 106.87, 113.39, 117.12, 119.62, 127.12, 127.31, 127.37, 127.44, 127.96, 128.01, 128.53, 128.83, 129.51, 131.51, 135.40, 136.61, 142.18, 156.89, 157.82, 208.15; FD-MS: 528 ($M^+$).

Example 8

Synthesis of Compound 8

Compound 7 (11.20 g, 0.021 mol) was dissolved in 100 mL of anhydrous THF and cooled to 0° C. LAH (1.60 g, 0.042 mol) was added in portions under nitrogen. After addition, the reaction was stirred for 15 min, and quenched with sodium sulfate decahydrate carefully. The reaction was filtered and the precipitated solid was washed methylene chloride. The filtrate was concentrated to give pure product at quantitative yield, 11.35 g. $^1$H NMR ($CDCl_3$) δ ppm: 0.78 (t, J=7.1 Hz, 3 H), 1.11-1.69 (m, 10 H), 4.81-4.85 (m, 1H, OH), 5.15 (s, 2 H), 5.21 (s, 2 H), 6.96 (dd, $J_1$=8.5 Hz, $J_2$=2.6 Hz, 2 H), 7.20-7.52 (m, 14H), 7.65 (s, 1H), 7.73 (d, J=2.2Hz, 1 H), 7.73-7.77 (m, 1 H); $^{13}$C NMR ($CDCl_3$): 14.00, 22.50, 25.81, 28.95, 31.60, 38.76, 70.07, 70.48, 106.97, 109.76, 111.76, 113.77, 119.47, 126.49, 127.55, 127.98, 128.03, 128.54, 128.59, 128.63, 128.79, 129.46, 131.37, 133.26, 133.54, 136.82, 143.92, 156.84; FD-MS: 530 ($M^+$).

Example 9

Synthesis of Compound 9

Compound 8 (14.10 g, 0.028 mol) was dissolved in 100 mL of methylene chloride and cooled to 0° C. To the solution was added boron trifluoride etherate (5.9 g, 0.042 mol). After 20 min, the reaction was quenched carefully with saturated sodium bicarbonate solution. Organic phase was separated and the aqueous phase was extracted with methylene chloride. The combined organic phase was dried over $MgSO_4$. The crude product was recrystallized from heptane twice to give 8.21 g of product as off-white solid (56% yield). $_1$H NMR ($CDCl_3$) δ ppm: 0.72 (t, J=7.1 Hz, 3 H), 0.80-0.83 (m, 2 H), 1.03-1.12 (m, 6H); 2.02-2.14 (m, 1 H), 2.17-2.27 (m, 1 H), 4.26-4.29 (m, 1 H), 5.10 (s, 2 H), 5.14 (s, 2 H), 6.96 (dd, $J_1$=8.3 Hz, $J_2$=2.2 Hz, 1 H), 7.16-7.47 (m, 14 H), 7.59 (d, J=8.3 Hz, 1 H), 7.65-7.73 (m, 2 H), 7.93 (d, J=8.7 Hz, 1H) $^{13}$C NMR ($CDCl_3$): 14.00, 22.57, 24.41, 29.52, 31.52, 33.66, 47.10, 70.03, 70.40, 108.66, 111.51, 113.19, 118.79, 119.16, 119.70, 125.36, 126.83, 127.56, 127.60, 127.94, 128.01, 128.57, 128.61, 133.82, 135.35, 136.64, 136.93, 137.15, 142.34, 149.97, 155.86, 157.93; FD-MS: 512 ($M^+$).

Example 10

Synthesis of Compound 10

Compound 9 (8.20 g, 0.016 mol) was suspended in 16 mL of DMSO and the mixture was degassed by bubbling with nitrogen for 10 min. To this mixture was added 3 drops of phase transfer reagent Aquat® 336 and 50% NaOH aqueous solution (2.56 g, 0.032 mol) under nitrogen. The reaction turned bright orange immediately. n-Hexylbromide (3.20 g, 0.019 mol) was then added dropwise and the reaction was heated to 80° C. The orange color disappeared and reaction became light yellow and clear. After 20 min, the reaction was poured into water and extracted with ether. The combined organic phase was washed with water and dried over $MgSO_4$. After the removal of the solvent, the pure product was obtained as light brownish-yellow oil (quantitative yield). $^1H$ NMR ($CDCl_3$) δ ppm: 0.44-0.52 (m, 4 H), 0.76 (t, J=7.1 Hz, 6 H), 0.94-1.12 (m, 12 H), 2.13-2.23 (m, 2 H), 2.42-2.52 (m, 2H), 5.21 (s, 2 H), 5.24 (s, 2 H), 7.05 (dd, $J_1$=8.2 Hz, $J_2$=2.3 Hz, 1 H), 7.11 (d, J=2.1 Hz, 1 H), 7.33-7.58 (m, 14 H), 7.68 (d, J=8.2 Hz, 1 H), 7.76-7.84 (m, 2 H), 8.16 (d, J=9.2 Hz); $^{13}C$ NMR ($CDCl_3$): 13.94, 22.50, 23.50, 29.54, 31.31, 40.52, 57.22, 69.97, 70.35, 108.93, 109.42, 112.98, 118.68, 118.82, 119.41, 124.78, 125.97, 127.01, 127.62, 127.91, 127.99, 128.52, 128.58, 134.22, 135.02, 136.94, 137.01, 137.09, 143.56, 153.66, 155.55, 158.24; FD-MS: 596 ($M^+$).

Example 11

Synthesis of Compound 11

Compound 10 (9.55 g, 0.016 mol) was dissolved in 100 mL of methylene chloride and was cooled to 0° C. To this solution was added boron, tribromide (6.05 g, 0.024 mol) dropwise. After 30 min, the reaction was quenched with saturated sodium bicarbonate. The aqueous layer was extracted with methylene chloride and the combined organic layer was washed with water and dried over $MgSO_4$. The crude product was washed with minimum amount of methylene chloride to 4.21 g give pure product as light tan solid and the filtrate was purified by column chromatography on silica gel to give 1.42 g of product (total yield 84%). $^1H$ NMR ($CDCl_3$) δ ppm: 0.34-0.47 (m, 4 H), 0.69 (t, J=7.0 Hz, 6 H), 0.90-1.05 (m, 12 H), 2.05-2.13 (m, 2 H), 2.33-2.43 (m, 2 H), 4.78 (br, 1 H), 4.93 (br, 1 H), 6.82 (dd, $J_1$=8.1 Hz, $J_2$=2.3 Hz, 1 H), 6.90 (d, J=2.2 Hz, 1 H), 7.15 ($J_1$=9.0 Hz, $J_2$=2.3 Hz, 1 H), 7.24 (d, J=2.4 Hz, 1 H), 7.57 (d, J=8.0 Hz, 1 H), 7.67 (d, J=8.2 Hz, 1 H), 7.75 (d, J=8.4 Hz, 1 H), 8.06 (d, J=9.1 Hz, 1 H); $^{13}C$ NMR ($CDCl_3$):13.93, 22.50, 23.51, 29.55, 31.34, 40.53, 109.45, 109.75, 111.37, 113.78, 117.60, 118.85, 118.88, 119.61, 125.09, 126.58, 128.80, 128.80, 134.92, 143.47, 152.08, 154.80; FD-MS: 416 ($M^+$).

Example 12

Synthesis of Compound 12

Compound 11 (5.60 g, 0.013 mol) and triethylamine (3.56 g, 0.035 mol) were dissolved in 80 mL of methylene chloride, and the solution was cooled to 0° C. Triflate anhydride (9.10 g, 0.032 mol) was added slowly. After 30 min, the reaction was quenched by water, and the aqueous phase was extracted with methylene chloride. The combined organic phase was washed with water and dried over $MgSO_4$. The crude product was recrystallized from heptane to give 7.12 g of pure product as light cream needles (79% yield). $^1H$ NMR ($CDCl_3$) δ ppm: 0.30-0.40 (m, 4H), 0.69 (t, J=6.9 Hz, 6 H), 0.88-1.04 (m, 12 H), 2.17-2.67 (m, 2 H), 2.38-2.48 (m, 2 H), 7.31-7.34 (m, 2 H), 7.48 (dd, $J_1$=9.2 Hz, $J_2$=2.5 Hz, 1 H), 7.83 (d, J=8.2 Hz, 1 H), 7.87 (d, J=2.5 Hz, 1 H), 7.91-7.98 (m, 2 H), 8.25 (d, J=9.3 Hz, 1 H); $^{13}C$ NMR ($CDCl_3$):13.80, 22.32, 23.40, 29.22, 31.15, 40.03, 58.08, 115.56, 120.12, 120.23, 120.27, 120.76, 120.98, 125.93, 128.91, 129.10, 133.98, 138.58, 140.81, 145.08, 146.56, 149.20, 154.48; FD-MS: 680 ($M^+$).

Example 13

Synthesis of Compound 13

Compound 12 (1.81 g, 0.003 mol), bis(neopentyl glycola) diboron (1.31 g, 0.006 mol) and potassium acetate (1.55 g, 0.016 mol) were mixed in 15 mL of dioxane. The mixture was bubbled with nitrogen for 5 min and catalyst bis (diphenylphosphino)ferrocene palladium chloride (Pd $(dppf)_2Cl_2$) (70 mg, 0.03 mol %) and ligand dppf (40 mg, 0.03 mol %) were added. The reaction was heated at 80° C. under nitrogen overnight. The reaction was extracted with methylene chloride and water, and the crude product was passed through a short column of silica gel to give 1.31 g of pure product as light yellow foam (82% yield). $^1H$ NMR ($CDCl_3$):0.26-0.40 (m, 4 H), 0.66 (t, J=7.0 Hz, 6 H), 0.83-0.98 (m, 12 H), 1.07 (s, 12 H), 2.21-2.31 (m, 2 H), 2.42-2.52 (m, 2 H), 3.83 (s, 4 H), 3.84 (s, 4 H), 7.75 (d, J=8.8 Hz, 1 H), 7.83 (d, J=8.4 Hz, 1 H), 7.85-7.92 (m, 4H), 8.18 (d, J=8.5 Hz, 1 H), 8.44 (s, 1 H); $^{13}C$ NMR ($CDCl_3$):13.91, 21.95, 22.04, 22.49, 23.48, 29.54, 31.31, 31.92, 31.97, 40.09, 57.31, 72.35, 72.44, 109.77, 118.47, 122.62, 127.10, 129.00, 130.06, 131.75, 132.61, 133.18, 136.64, 139.72, 144.00, 144.78, 151.40; FD-MS: 608 ($M^+$).

Example 14

Synthesis of Compound 14
(2,6-dihexyloxynaphthalene)

2,6-Dihydroxynaphthalene (30.0 g, 0.19 mol) reacted with n-hexylbromide (68.06 g, 0.41 mol) in the presence of potassium carbonate (129.6 g, 0.94 mol) in 400 mL of DMF at 95° C. for 3 h. The reaction was poured into 700 mL of water and the precipitate was filtered, washed with water and methanol, and dried. The crude product was recrystallized from ethanol to give 54.5 g (88% yield) of pure product white crystals. $^1H$ NMR $CDCl_3$) δ (ppm):0.91 (t, J=6.9 Hz, 6H), 1.32-1.40 (m, 8H), 1.44-1.54 (m, 4H), 1.77-2.86 (m, 4H), 4.02 (t, J=6.6 Hz, 4H), 7.06-7.12 (m, 4H), 7.60 (d, J=8.8 Hz, 2H); M.p. 78-79° C.; FD-MS: 328 ($M^+$).

Example 15

Synthesis of Compound 15

Compound 14 (25.5 g, 0.078 mol) was dissolved in 250 mL of methylene chloride and cooled to 0° C. To this solution was added aluminum chloride (12.7 g, 0.085 mol) in portions and heptanoyl chloride (12.4 g, 0.093 mol) was added via an additional funnel. The reaction was monitored by TLC and was quenched carefully with 2N HCl solution. The reaction was extracted with methylene chloride and the combined organic phase was dried over $MgSO_4$. The crude product was recrystallized from heptane to give 25.4 g (74% yield) as light yellow powder. $^1H$ NMR $CDCl_3$) δ (ppm): 0.77-0.85 (m, 9 H), 1.21-1.39 (m, 18 H), 1.61-1.76 (m, 6H), 2.84 (t, J=7.4 Hz, 2 H), 3.91-4.00 (m, 4 H), 6.98 (d, J=2.4 Hz, 1 H), 7.04 (dd, $J_1$=9.1 Hz, $J_2$=2.4 Hz, 1 H), 7.09 (d, J=9.1 Hz, 1 H), 7.48 (d, J=9.2 Hz, 1 H), 7.61 (d, J=9.1 Hz, 1 H); FD-MS: 440 ($M^+$).

Example 16

Synthesis of Compound 16

Compound 15 (20.0 g, 0.045 mol) was dissolved in 200 mL of methylene chloride and cooled to 0° C. To the solution was slowly added boron tribromide (34.45 g (13.0 mL), 0.14 mol). The reaction was stirred for 1 h and quenched carefully with saturated NaHCO$_3$ solution. The reaction was extracted with methylene chloride and the combined organic phase was dried over MgSO$_4$. The crude product was recrystallized from heptane to give 10.2 g (83% yield) of pure product as yellow solid. $^1$H NMR CDCl$_3$) δ (ppm): 0.85 (t, J=7.0 Hz, 3 H), 1.29-1.35 (m, 6 H), 1.77-1.84 (m, 2 H), 3.13 (t, J=7.4 Hz, 2 H), 5.04 (br, 1 H), 7.10-7.19 (m, 3 H), 7.72 (d, J=9.9 Hz, 1 H), 7.94 (d, J=9.3 Hz, 1 H), 12.75 (s, 1 H); FD-ES:273 (M+1)$^+$.

Example 17

Synthesis of Compound 17

Compound 16 (30.02 g, 0.11 mol) was dissolved in 200 mL of acetone. To the solution was added potassium carbonate (38.05 g, 0.28 mol) and catalytic amount of 18-crown-6. The mixture was stirred for 5 min. and benzyl bromide (47.2 g, 0.28 mol) was added. The reaction was heated to reflux for 2 h and then solvent was removed. The residue was extracted with methylene chloride/water. Pure product was obtained by recrystallization using heptane (40.1 g, 80% yield). $^1$H NMR CDCl$_3$) δ (ppm): 0.72 (t, J=7.4 Hz, 3 H), 1.12-1.19 (m, 6 H), 1.52-1.61 (m, 2 H), 2.78 (t, J=7.5 Hz, 2 H), 5.01 (s, 2 H), 5.04 (s, 2 H), 7.03 (d J=2.5 Hz, 1 H), 7.09 (d, J=9.4 Hz, 1 H), 7.10 (d, J=9.1 Hz, 1H), 7.18-7.34 (m, 10 H), 7.46 (d, J=9.2 Hz, 1 H), 7.56 (d, J=9.1 Hz, 1 H); FD-ES: 453 (M+1)$^+$.

Example 18

Synthesis of Compound 18

Compound 17 (16.0 g, 0.035 mol) was dissolved in 200 mL of toluene. To the solution was added anhydrous magnesium bromide/ether complex (9.12 g, 0.035 mol). The reaction was refluxed overnight. The reaction was cooled and water was added. The organic phase was separated and the aqueous phase was extracted with ether. The combined organic phase was dried over MgSO$_4$. The pure product was obtained by column chromatography on silica gel using heptane/ether as an eluent (11.5 g, 90% yield). $^1$H NMR CDCl$_3$) δ (ppm): 0.85 (t, J=7.0 Hz, 3 H), 1.29-1.35 (m, 6H), 1.77-1.84 (m, 2 H), 3.08 (t, J=7.4 Hz, 2 H), 5.11 (s, 2 H), 7.93-7.46 (m, 8 H), 7.68 (d, J=9.1 Hz, 1 H), 7.92 (d, J=9.2 Hz, 1 H), 12.74 (s, 1 H); FD-MS: 362 (M$^+$).

Example 19

Synthesis of Compound 19

Compound 18 (3.02 g, 0.0083 mol) was dissolved in 30 mL of methylene chloride and cooled to 0° C. To this solution was added triethylamine (1.01 g, 0.0099 mol) and trifluoromethane sulfonic anhydride (2.85 g, 0.01 mol) was added dropwise. After 20 min, the reaction was quenched by water and extracted with methylene chloride. The pure product was obtained by passing through a short silica gel column (4.0 g, quantitative yield). FD-MS: 494 (M$^+$).

Example 20

Synthesis of Compound 20

Compound 6 (9.27 g, 0.033 mol) and compound 19 (15.0 g, 0.030 mol) were dissolved in 150 mL of toluene. To this solution was added 2 M Na$_2$CO$_3$ (30 mL, 0.060 mol) and a drop of phase transfer reagent Aliquat 336. The mixture was bubbled with nitrogen for 10 min and catalyst Pd(PPh$_3$)$_4$ (0.52 g, 1.5 mol %) was added. The reaction was heated to 105° C. for 3 h and cooled down. The reaction was extracted with methylene chloride and the combined organic phase was dried over MgSO$_4$. The crude product was recrystallized from heptane to give 10.34 g (60% yield) pure product as light yellow solid. FD-MS: 578 (M$^+$).

Example 21

Synthesis of Compound 21

Compound 20 (1.0 g, 1.7 mmol) was dissolved in 10 mL of anhydrous THF and cooled to 0° C. To this cold solution was added LiAlH$_4$ (0.10 g, 2.6 mmol). The reaction was stirred for 20 min and quenched with sodium sulfate decahydrate and then filtered. The precipitate was washed thoroughly with methylene chloride. The filtrate was evaporated to give 0.81 g (81% yield) of pure product as yellow solid. FD-MS: 580 (M$^+$).

Example 22

Synthesis of Compound 22

Compound 21 (8.85 g, 0.015 mol) was dissolved in methylene chloride and cooled to 0° C. To this solution was added dropwise trifluoroacetic acid (2.47 g, 0.022 mol). After 20 min, reaction was quenched with water and extracted with methylene chloride. The pure product was obtained from recrystallization of the crude product from heptane to give white pulp-like solid (6.36 g, 75% yield). $^1$H NMR CDCl$_3$) δ (ppm): 0.32-0.37 (m, 2 H), 0.61 (t, J=7.0 Hz, 3 H), 0.83-0.92 (m, 4H), 1.26-1.38 (m, 2 H), 2.53-2.55 (m, 2 H), 4.86 (br, 1 H), 5.21 (s, 4 H), 7.25-7.53 (m, 17 H), 7.68 (d, J=8.3 Hz, 1 H), 7.92 (d, J=8.3 Hz, 1 H), 8.09 (d, J=8.8 Hz, 1 H); $^{13}$C NMR (CDCl$_3$): 13.87, 22.42, 29.38, 31.29, 33.79, 46.36, 70.06, 108.61, 118.85, 119.26, 125.45, 125.81, 126.73, 127.62, 128.03, 128.63, 133.96, 136.94, 137.77, 143.45, 155.95; FD-MS: 562 (M$^+$).

Example 23

Synthesis of Compound 23

Compound 22 (1.0 g, 1.78 mmol) was suspended in 2 mL of DMSO. The suspension was degassed by bubbling nitrogen for 5 min. and 50% NaOH aqueous solution (0.28 g, 3.56 mmol) and a drop of phase transfer reagent Aliquat® 336, followed by slow addition of n-hexylbromide (0.35 g, 2.13 mmol). The reaction turned into bright orange upon addition of NaOH, and changed into light yellow when n-hexylbromide was added. The reaction was heated to 80° C. for 20 min. during which the reaction became clear light yellow solution. The reaction was poured into water, extracted with ether and dried to give quantitative pure product as off-white solid. $^1$H NMR CDCl$_3$) δ (ppm): 0.21-0.25 (m, 4 H), 0.59 (t, J=7.0 Hz, 6H), 0.74-0.92 (m, 8 H), 1.26-1.34 (m, 4 H), 2.65-2.70 (m, 4 H), 5.19 (s, 4 H), 7.30-7.44 (m, 10 H), 7.51 (d, J=7.2 Hz, 4 H), 7.77 (d, J=8.3 Hz, 2 H), 7.90 (d, J=8.3 Hz, 2 H), 8.30 (d, J=9.2 Hz, 2 H); $^{13}$C NMR (CDCl$_3$): 13.83, 22.36, 23.54, 29.39, 31.15, 40.12, 59.95, 69.99, 109.15, 118.58, 118.77, 124.67, 125.38, 127.11, 127.64, 128.01, 128.60, 134.65, 136.92, 137.48, 145.14, 155.54; FD-MS: 646 (M$^+$).

Example 24

Synthesis of Compound 24

Compound 23 (1.0 g, 1.5 mmol) was dissolved in 30 mL of methylene chloride and cooled to 0° C. To this solution was added boron tribromide (0.85 g, 3.4 mmol) dropwise. After 30 min, the reaction was quenched with saturated sodium bicarbonate. The aqueous layer was extracted with methylene chloride and the combined organic layer was washed with water and dried over MgSO$_4$. The crude product was washed with minimum amount of methylene chloride to 0.41 g give pure product as light tan solid and the filtrate was purified by column chromatography on silica gel using ether/heptane as an eluent to give 0.19 g of product (total yield 74%). $^1$H NMR (CDCl$_3$) δ ppm: 0.18-0.28 (m, 4 H), 0.60 (t, J=7.0 Hz, 6 H), 0.74-0.98 (m, 8 H), 1.12-1.31 (m, 4 H), 2.63-2.68 (m, 4 H), 5.08 (br, 2 H), 7.20 (dd, J$_1$=9.1 Hz, J$_2$=2.6 Hz, 2 H) 7.30 (d, J=2.6 Hz, 2 H), 7.73 (d, J=8.4 Hz, 2 H), 7.89 (d, J=8.4 Hz, 2 H); FD-MS: 466 (M$^+$).

Example 25

Synthesis of Compound 25

Compound 24 (1.0 g, 2.14 mmol) was dissolved in methylene chloride and cooled to 0° C. To the solution was added triethylamine (0.54 g, 5.36 mmol) followed by slow addition of trifluoromethanesulfonic anhydride (1.51 g, 5.36 mmol). The reaction was stirred at room temperature for 30 min and quenched with water. The reaction was extracted with methylene chloride and the organic phase was dried with MgSO$_4$. The crude product was recrystallized from heptane to give 1.1 g pure product as light yellow crystals (70% yield). $^1$H NMR (CDCl$_3$) δ ppm: 0.13-0.23 (m, 4 H), 0.59 (t, J=7.0 Hz, 6 H), 0.74-0.89 (m, 12 H), 2.66-2.72 (m, 4 H), 7.50 (dd, J$_1$=9.3 Hz J$_2$=2.5 Hz, 2 H), 7.90 (d, J=2.6 Hz, 2 H), 7.97 (d, J=8.4 Hz, 2 H), 8.09 (d, J=8.4 Hz, 2 H), 8.44 (d, J=9.4 Hz, 2 H); 13.74, 22.24, 23.39, 29.13, 31.04, 40.06, 60.53, 119.88, 120.07, 121.18, 125.61, 128.59, 128.81, 133.98, 139.87, 145.87, 146.25, FD-MS: 730 (M$^+$).

Example 26

Synthesis of Compound 26

Compound 22 (7.0 g, 12.46 mmol) was suspended in 15 mL of DMSO. The suspension was degassed by bubbling nitrogen for 5 min. and 50% NaOH aqueous solution (1.96 g, 24.92 mmol) and 3 drop of phase transfer reagent Aliquat® 336, followed by slow addition of 2-ethylhexylbromide (2.89 g, 14.94 mmol). The reaction turned into bright orange upon addition of NaOH, and changed into light yellow when 2-ethylhexylbromide was added. The reaction was heated to 80° C. for 20 min. during which the reaction became clear light yellow solution. The reaction was poured into water, extracted with ether and dried to give quantitative 6.8 g of pure product as light yellow viscous oil (92% yield). FD-MS: 674 (M$^+$).

Example 27

Synthesis of Compound 27

Compound 26 (8.0 g, 11.87 mmol) was dissolved in methylene chloride and cooled to 0° C. To the solution was added boron tribromide (7.47 g, 29.68 mmol) dropwise. The reaction was stirred for 20 min. and quenched with saturated Na$_2$CO$_3$ solution, and extracted with methylene chloride. The crude product was purified by column chromatography on silica gel using 1/1 methylene chloride/heptane as an eluent to 3.5 g give pure product as light brown solid (60% yield). $^1$H NMR (CDCl$_3$) δ ppm: 0.16-0.87 (m, 26 H), 2.62-2.67 (m, 4 H), 7.20 (dd, J$_1$=9.1 Hz, J$_2$=1.3 Hz,2 H), 7.28 (d, J=2.6 Hz, 2 H), 7.73 (d, J=8.3 Hz, 2 H), 7.88 (dd, J$_1$=8.3 Hz, J$_2$=1.2 Hz, 2 H), 8.28 (dd, J$_1$=9.1 Hz, J$_2$=2.6 Hz, 2 H); $^{13}$C NMR (CDCl$_3$): 10.34, 13.86, 13.96, 22.46, 22.55, 23.25, 26.51, 27.70, 29.42, 31.22, 32.79, 35.64, 41.18, 43.51, 59.70, 111.47, 111.50, 131.31, 117.33, 117.36, 118.76, 125.35, 125.47, 125.54, 0.61, 126.68, 126.73, 134.53, 134.62, 137.25, 137.32, 145.34, 145.46, 151.85; FD-MS: 494 (M$^+$).

Example 28

Synthesis of Compound 28

Compound 27 (3.50 g, 7.1 mmol) was dissolved in 100 mL of methylene chloride and cooled to 0° C. To this solution was added triethylamine (1.43 g, 14.1 mmol) followed by slow addition of triflic anhydride (4.41 g, 15.6 mmol). The reaction was stirred at room temperature for 20 min. and quenched with water. The reaction was extracted with methylene chloride and the organic phase was dried over MgSO$_4$. The crude product was purified by column chromatography on silica gel using methylene chloride/heptane (5/95) as an eluent to give 2.35 g of pure product as light cream solid (44% yield). $^1$H NMR (CDCl$_3$) δ ppm: 0.11-1.26 (m, 26 H), 2.67-2.71 (m, 4 H), 7.50 (d, J=9.4 Hz, 2 H), 7.89 (d, J=2.4 Hz, 2 H), 7.97 (d, J=8.4 Hz, 2 H), 8.08 (d, J=8.4 Hz, 2 H), 8.45 (d, J=9.3 Hz, 1 H), 8.47 (d, J=9.3 Hz, 1 H); $^{13}$C NMR (CDCl$_3$): 10.12, 13.50, 13.66, 22.23, 22.36, 22.72, 23.09, 26.56, 27.54, 29.09, 31.03, 32.79, 35.76, 40.96, 43.36, 60.27, 119.74, 120.09, 121.05, 121.13, 126.09, 128.87, 128.97, 133.94, 133.99, 139.91, 139.93, 146.22, 146.33, 146.37, 146.38; FD-MS: 758 (M$^+$).

Example 29

Synthesis of Compound 29

To a 500 mL round-bottomed flask was added 200 mL of methylene chloride and phenyldecane (37.6 g, 0.17 mol). The solution was cooled to 0° C., and aluminum chloride (18.4 g, 0.14 mol) was added in portions, followed by slow addition of o-bromobenzoyl chloride (25.2 g, 0.11 mol). The reaction was stirred at room temperature until completion and cooled to 0° C. and quenched carefully with 2 N HCl solution. The reaction was extracted with methylene chloride, and the combined organic phase was dried over MgSO$_4$. The crude product was purified by column on silica gel to give 41.6 g of product as clear oil (90% yield). FD-MS: m/z 401 (M$^+$).

Example 30

Synthesis of Compound 30 (4-(2-ethylhexyloxy)-bromobenzene)

To a 1-L round-bottomed flask were added 4-bromophenol (60.0 g, 0.35 mol), potassium carbonate (52.7 g, 0.38 mol), 2-ethylhexyl bromide (73.7 g, 0.38 mol) and DMF 200 mL. The reaction mixture was stirred at 90° C. under nitrogen overnight. The reaction was poured into water and extracted with ether three times and the combined organic phase was washed with water three times and dried over $MgSO_4$. After solvent was removed, the crude product was obtained as light brown liquid. Pure product was obtained by column chromatography on silica gel using ether/hexane (10/90) as an eluent as a light yellow liquid, 71.2 g (72% yield). $^1$H NMR (CDCl$_3$) δ (ppm): 0.88-0.93 (m, 6H, CH$_3$), 1.27-1.46 (m, 8H), 1.65-1.74 (m, 1 H), 3.78 (d, J=5.7 Hz, 2H, OCH$_2$), 6.76 (d, J=8.9 Hz, 2 H), 7.33 (d, J=8.9 Hz, 2 H); $^{13}$C NMR (CDCl$_3$): 11.08, 14.08, 23.03, 23.80, 29.05, 30.46, 39.29, 70.72, 112.42, 116.29, 132.11, 158.47; FD-MS: m/z 285 (M$^+$).

Example 31

Synthesis of Compound 31 (2,6-bis(t-butyldimethylsilyloxy)-anthraquinone)

To a 2-L round-bottomed flask were added 2,6-dihydroxy-anthra-quinone (80.0 g, 0.33 mol), imidazole (108.8 g, 1.6 mol), t-butyldimethylsilyl chloride (115.5 g, 0.77 mol), and DMF 600 mL. The dark red mixture was heated to 90° C. for 3 h. TLC indicated the completion of the reaction. The reaction was cooled down and poured into 2 L of cool water. The dark green needle like precipitate was filtered off and washed with water and methanol. The dark green crystals were dissolved in ether and the black insoluble part was filtered off. The bright yellow filtrate was concentrated and the crude product was suspended in boiling methanol and filtered to give pure 85.1 g product as yellow silky crystals (54% yield). $^1$H NMR (CDCl$_3$) δ (ppm): 0.28 (s, 12H), 1.00 (s, 18H), 7.14 (dd, J$_1$=8.5 Hz, J$_2$=2.5 Hz, 2H), 7.64 (d, J=2.5 Hz, 2 H), 8.17 (d, J=8.5 Hz, 2H); $^{13}$C NMR(CDCl$_3$): −4.36, 25.53, 117.35, 125.34, 127.57, 129.73, 135.73, 161.26, 182.17; M.p. 131-133° C.; FD-MS: m/z 468 (M$^+$).

Example 32

Synthesis of Compound 32 (2,6-dihydroxy-9,10-di (4-(2-ethyl-hexyloxy)phenyl)anthracene)

Compound 30 (18.3 g, 0.064 mol) was dissolved in 60 mL of anhydrous THF and cooled to −78° C. To this solution was added n-BuLi (2.5 M in hexane, 25.6 mL, 0.064 mol) slowly to maintain the temperature below −60° C. After addition, the orange-yellow solution was stirred at −78° C. for an hour. Compound 31 (10.0 g, 0.021 mol) was dissolved in 30 mL of anhydrous THF and added dropwise to the above cooled solution. TLC analysis indicated the completion of the reaction after 3 h. The reaction was warmed up slightly and HI solution (47% in water, 39 mL, 0.21 mol) was added slowly to quench the reaction and to de-protect the TBDMS group. The deep brown reaction was heated to reflux for 10 min. and most of the solvent was removed under reduced pressure. The reaction mixture was then extracted with methylene chloride three times. The combined organic phase was washed with saturated sodium metabisulfate solution, water, and brine, and dried over $MgSO_4$. The crude product was obtained as brown viscous oil and was purified by column chromatography on silica gel with 15/85 ether/hexane as an eluent. The pure product was obtained as light green-yellow solid 5.5 g (42% yield). $^1$H NMR (CDCl$_3$) δ (ppm): 0.92-1.01 (m, 12H, CH$_3$), 1.26-1.46 (m, 16H), 1.77-1.86 (m, 2H), 3.96 (d, J=5.7 Hz, 4H, OCH$_2$), 4.93 (s, br, 2H, OH), 6.91 (d, J=2.3 Hz, 2H), 6.95 (dd, J$_1$=9.5 Hz, J$_2$=2.4 Hz, 2H), 7.09 (d, J=8.6 Hz, 4H, phenyl), 7.31 (d, J=8.6 Hz, 4H, phenyl), 7.60 (d, J=9.4 Hz, 2H); $^{13}$C NMR (CDCl$_3$): 11.17, 14.13, 23.09, 23.91, 29.13, 30.58, 39.46, 70.62, 106.88, 114.49, 118.59, 127.33, 129.00, 129.93, 131.02, 132.21, 151.75, 158.72; M.p. 195-197° C.; FD-MS: m/z 618 (M$^+$).

Example 33

Synthesis of Compound 33 (2,6-di(triflate)-9,10-di (4-(2-ethyl-hexyloxy)phenyl)anthracene)

Compound 32 (4.5 g, 0.007 mol) was dissolved in 50 mL of dry pyridine and cooled to 0° C. To this brown red solution was added slowly triflate anhydride (6.2 g, 0.022 mol). The dark green reaction was stirred at room temperature for 20 min. TLC indicated the completion of the reaction. The reaction was poured into water and extracted with ether (3×200 mL). The combined organic phase was washed with 2N HCl (2×200 mL) and dried over $MgSO_4$. The crude product was purified by column chromatography on silica gel using CH$_2$Cl$_2$/hexane (10/90) to give 5.9 g of blue fluorescent yellow crystalline product (92% yield). $^1$H NMR (CDCl$_3$) δ (ppm): 0.94-1.04 (m, 12H, CH$_3$), 1.38-1.60 (m, 16H), 1.81-1.88 (m, 2H), 4.01 (d, J=5.7 Hz, 4H, OCH$_2$), 7.16 (d, J=8.5 Hz, 4H, phenyl), 7.25 (dd, J$_1$=9.5 Hz, J$_2$=2.4 Hz, 2H), 7.35 (d, J=8.5 Hz, 4H, phenyl), 7.66 (d, J=2.3 Hz, 2H), 7.88 (d, J=9.5 Hz, 2H); M.p. 103-104° C.; FD-MS: m/z 882 (M$^+$).

Example 34

Synthesis of Compound 34 (2,6-di(2,2-dimethyltrimethylenediboronate)-9,10-di(4-(2-ethylhexyloxy) phenyl)anthracene)

Compound 33 (4.1 g, 0.005 mol), bis(neopentyl glycolato)diboron (2.3 g, 0.01 mol), 1,1'-bis(diphenylphosphino) ferrocene)dichloropalladium (II)/dichloromethane complex (0.23 g, 6 mol % to compound 33), 1,1'-bis(diphenylphosphino)ferrocene (0.15 g, 6 mol % to 33), and potassium acetate (2.7 g, 0.028 mol) were mixed with 50 mL of dioxane. The mixture was degassed with nitrogen for 10 min. and then heated to 80° C. overnight. The reaction was cooled and ice water 50 mL was added. Brown precipitate formed and was filtered, washed with water, and hexane. The brownish yellow solid was dissolved in ether, washed with water (5×100 mL) to remove the by-product neopentyl glycol to give 3.3 g of product as light brownish yellow solid (88% yield). $^1$H NMR (CDCl$_3$) δ (ppm): 0.94-1.04 (m, 24H, CH$_3$), 1.21-1.43 (m, 16H), 1.80-1.88 (m, 2H), 3.72 (s, 8H), 4.02 (d, J=5.7 Hz, 4H, OCH$_2$), 7.14 (d, J=8.5 Hz, 4H, phenyl), 7.38 (d, J=8.5 Hz, 4H, phenyl), 7.62-7.70 (m, 4H), 8.28 (s, 2H); $^{13}$C NMR (CDCl$_3$): 11.24, 14.16, 21.95, 23.12, 23.95, 29.20, 30.64, 31.83, 39.57, 70.71, 72.24, 114.38, 126.02, 128.25, 130.20, 130.98, 131.26, 132.38, 132.49, 134.41, 134.52, 137.47, 158.59; M.p. 191-193° C.; FD-MS: m/z 810 (M$^+$).

Synthesis of Polymers

Example 35

General Procedure for Synthesis of Polymers via the Suzuki Coupling Reaction

Equal molar of aromatic di-bromide or di-triflate and aromatic di-boron compound, and phase transfer reagent Aliquat® 336 (0.10 equivalent to monomer) were dissolved in of toluene (the ratio of toluene to water (v/v) is about 3/1). To this solution was added 2 M $Na_2CO_3$ aqueous solution (3.3 equivalent to monomer). The reaction mixture was bubbled with dry nitrogen for 15 min and catalyst tetrakis (triphenylphosphine)palladium (0.03 equivalent to monomer) was added. The reaction was heated under vigorous reflux for 12-24 h, and small amount of phenylboronic acid was added for end-capping of bromo group. The reaction was heated for 5 h and bromobenzene was added to end-cap boronate group. The reaction was heated for another 4 h and then poured into 200 mL of methanol. The precipitated polymer was washed with methanol, diluted HCl solution, and dried. The polymer was treated with diethyl dithiocarbamate twice: polymer was dissolved in toluene, and sodium diethyl dithiocarbamate in water (1 g in 10 mL of water) was added, and the mixture was stirred under nitrogen at 60° C. overnight. The toluene layer was separated and concentrated and the polymer was precipitated into methanol twice. Polymer can then be extracted with acetone with a Sohxlet setup overnight to remove oligomers. Polymer was dried under vacuum at 45° C.

EL Device Fabrication and Performance

Example 36

An EL device satisfying the requirements of the invention was constructed in the following manner. The organic EL medium has a single layer of the organic compound described in this invention.

a) An indium-tin-oxide (ITO) coated glass substrate was sequentially ultra-sonicated in a commercial detergent, rinsed with deionized water, degreased in toluene vapor and exposed to ultraviolet light and ozone for a few minutes.

b) An aqueous solution of PEDOT (1.3% in water, Baytron P Trial Product AI 4083 from H. C. Stark) was spin-coated onto ITO under a controlled spinning speed to obtain thickness of 500 Angstroms. The coating was baked in an oven at 110° C. for 10 min.

c) A toluene solution of a compound (300 mg in 30 mL of solvent) was filtered through a 0.2 μm Teflon filter. The solution was then spin-coated onto PEDOT under a controlled spinning speed. The thickness of the film was between 500-700 Angstroms.

d) On the top of the organic thin film was deposited a cathode layer including 15 angstroms of a CsF salt, followed by 2000 angstroms of a 10:1 atomic ratio of Mg and Ag.

The above sequence completed the deposition of the EL device. The device was then hermetically packaged in a dry glove box for protection against ambient environment.

Figure 2:
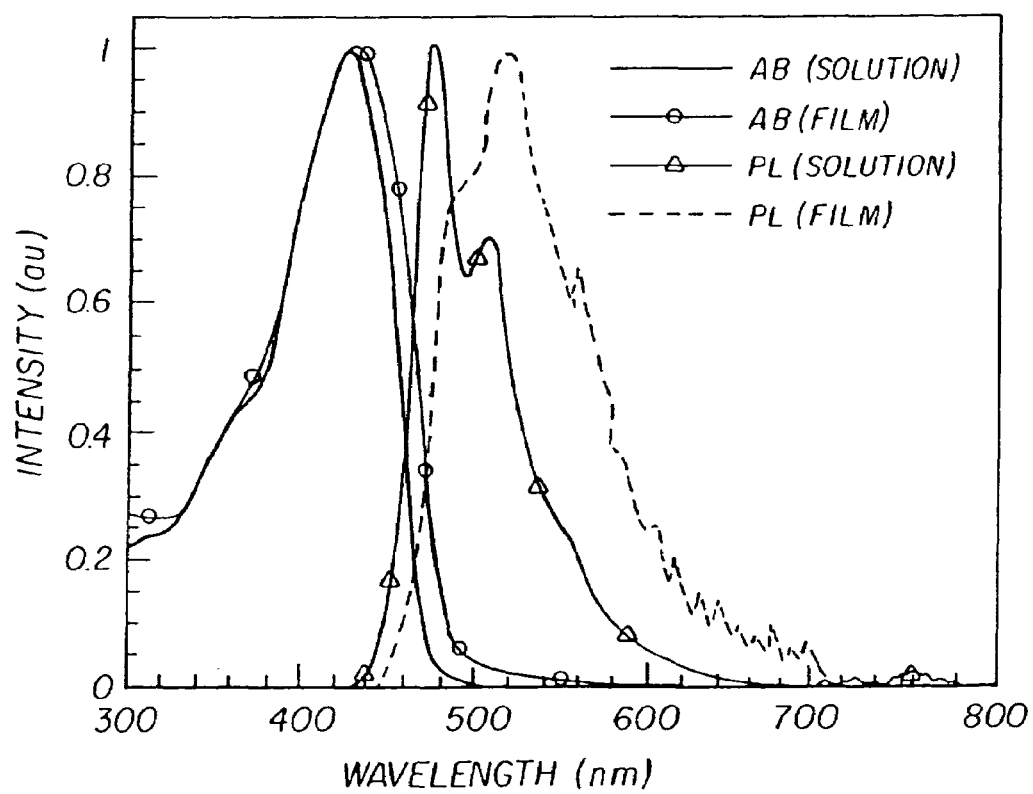
FIG. 2 illustrates the absorption (AB) and photoluminescence (PL) spectra of compound 231.
Figure 3:
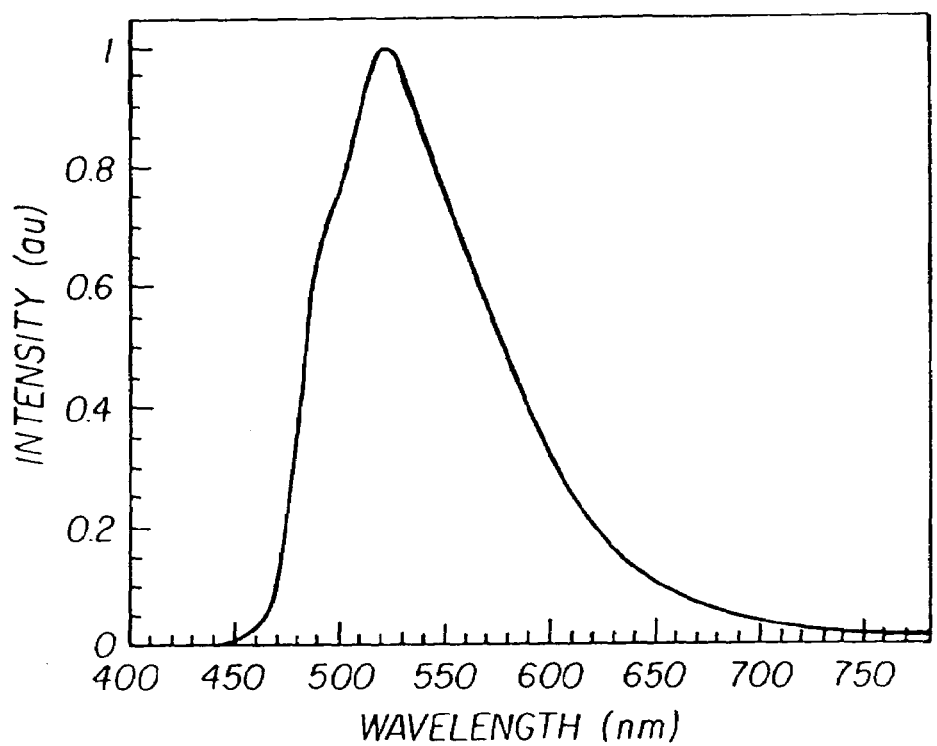
FIG. 3 illustrates the EL spectrum of an EL device fabricated from compound 231.
Figure 4:
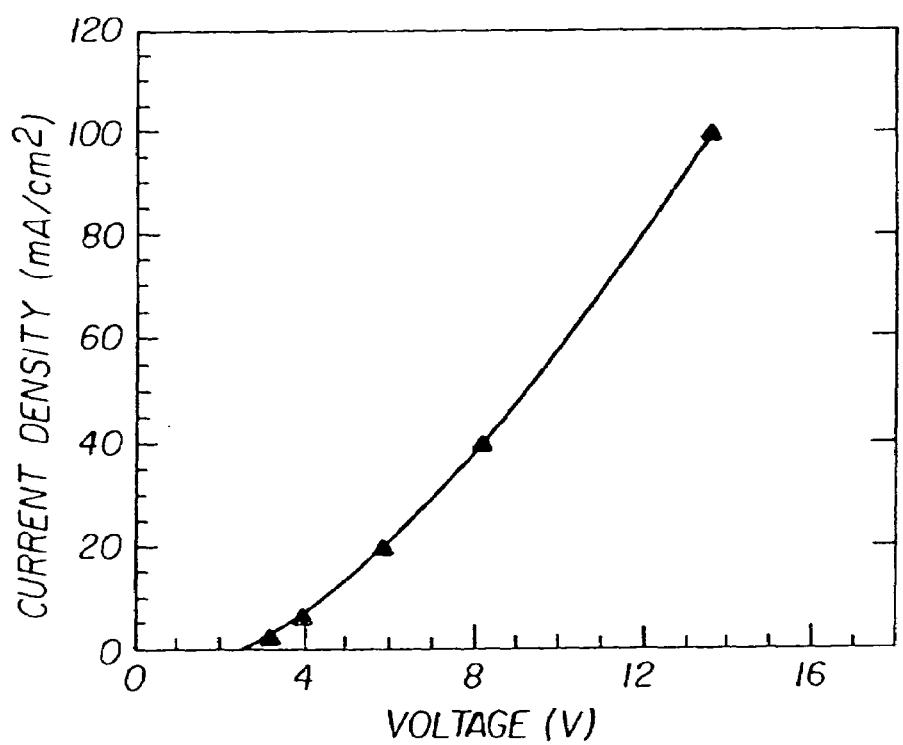
FIG. 4 illustrates the voltage-current density and luminance characteristics of a EL device fabricated from compound 231.
Figure 5:
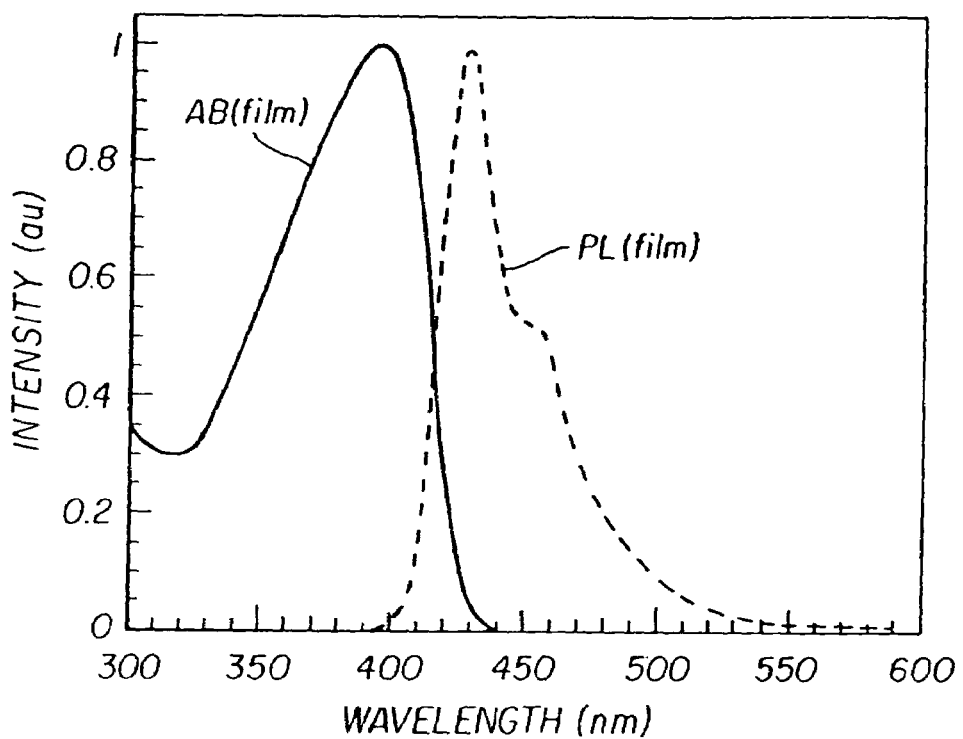
FIG. 5 illustrates the absorption (AB) and photoluminescence (PL) spectra of compound 206.
Figure 6:
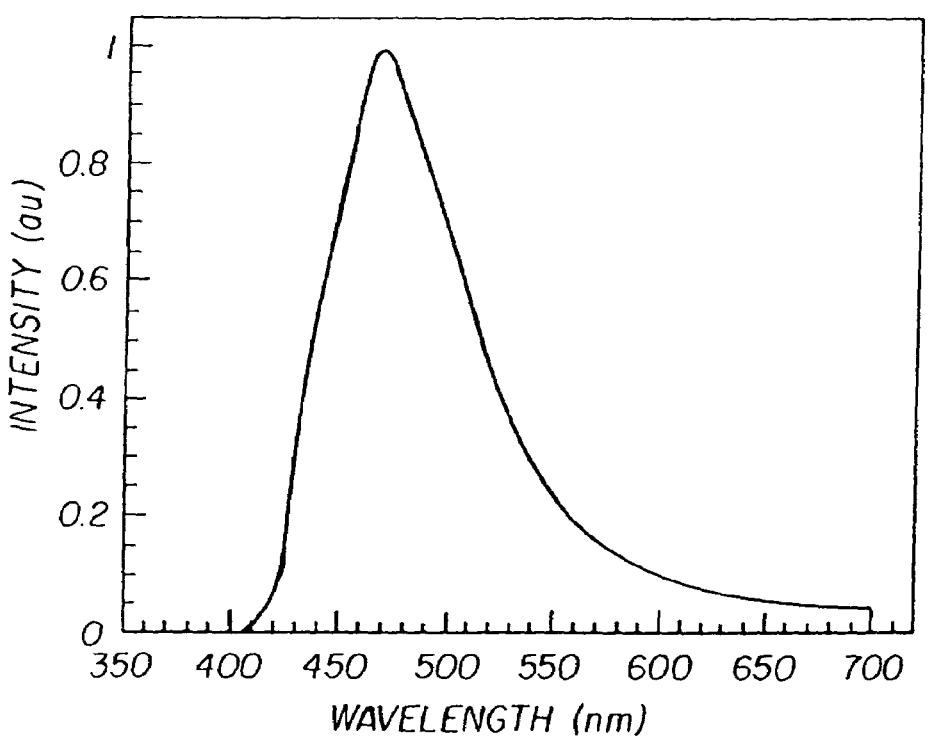
FIG. 6 illustrates the EL spectrum of an EL device fabricated from compound 206.
Figure 7:
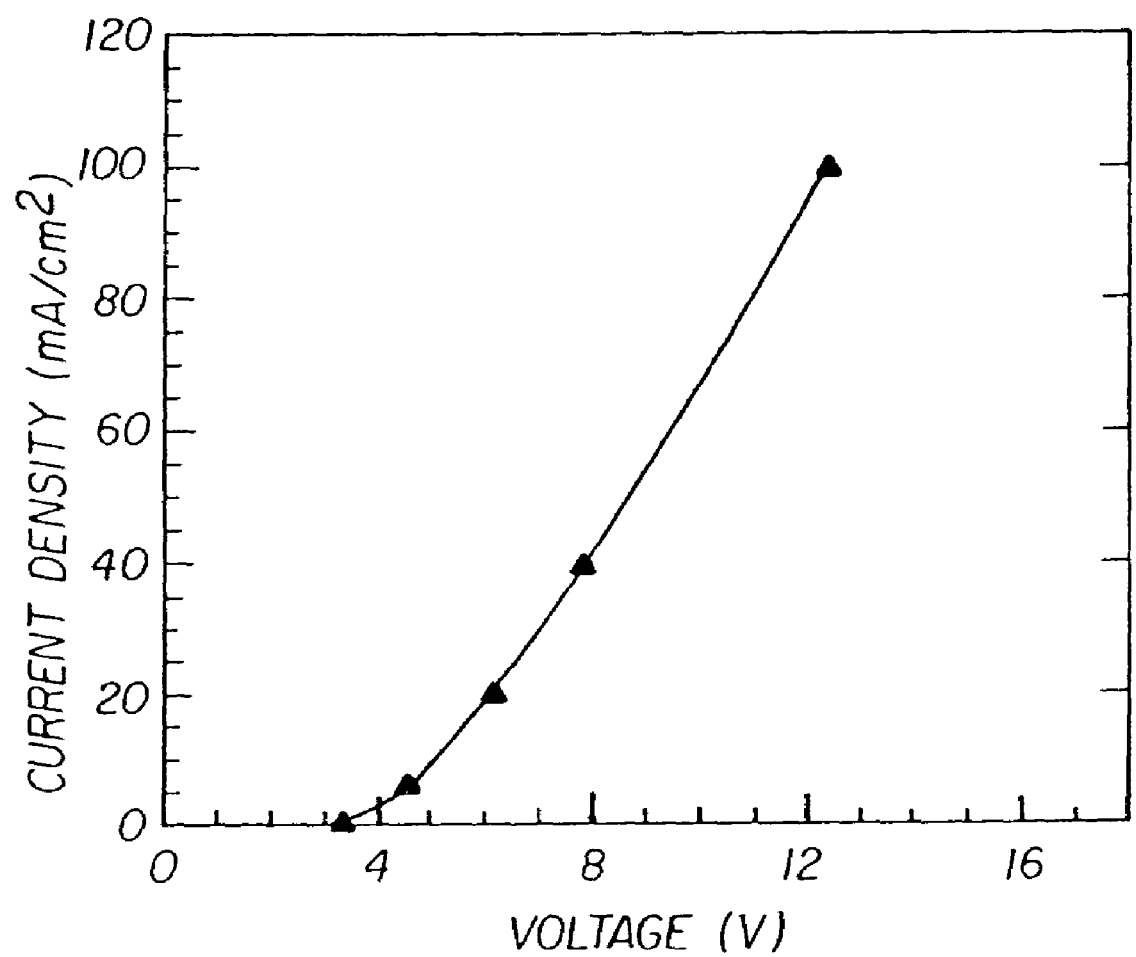
FIG. 7 illustrates the voltage-current density and luminance characteristics of a EL device fabricated from compound 206.

Table 1 summarizes the characterization of the polymers prepared in the present invention. Absorption (AB) and photoluminescence (PL) spectra were obtained from dilute solutions and solid thin films of the polymers and EL spectra were obtained from ITO/PEDOT/organic compound/CsF/Mg:Ag EL devices. The fabrication of EL devices was illustrated in Example 36. FIGS. 2 and 5 show the AB and PL spectra of compounds 231 and 206, respectively. FIGS. 3 and 6 show the EL spectra of compounds 231 and 206, respectively. And the voltage-current characteristics of the EL device of compounds 231 and 206 are shown in FIG. 4 and 7, respectively.

TABLE 1

Characterization of polymers according to Examples

| Compound | $M_w$[a] | PDI | $T_d$ (° C.) | $T_g$ (° C.) | UV[b] ($\lambda_{max}$ nm) | PL[c] ($\lambda_{max}$ nm) | EL ($\lambda_{max}$ nm) |
|---|---|---|---|---|---|---|---|
| 165 | 16300 | 1.70 | 428 | 183 | 380 | 420 (382) | 452 |
| 167 | 23200 | 2.30 | 441 | 50 | 342 | 396 (342) | 412 |
| 168 | 29200 | 1.97 | 418 | 86 | 376 | 420 (380) | 452 |
| 174 | 34400 | 2.01 | 429 | 138 | 392 | 424 (394) | 456 |
| 190 | 7000 | 1.85 | 426 | 137 | 378 | 424 (394) | 476 |
| 221 | 14100 | 1.80 | 430 | 190 | 362 | 410 (364) | 440 |
| 206 | 38200 | 2.15 | 358 | NO[f] | 392 | 432 (394) | 468 |
| 231 | 39300 | 2.62 | 405 | 123 | 428 | 522 (430) | 520 |
| 215 | 13100 | 1.65 | 433 | 140 | 388 | 426 (384) | 456 |
| 133 | 29000 | 2.27 | 420 | 72 | 358 | 422 (360) | 468 |
| 280 | 976 | 1.21 | 278 | 70 | NA[d] | NA | NA |
| 282 | 4920 | 1.57 | 454 | 182 | 394[e] | 448 (396)[e] | 488 |
| 278 | 2550 | 1.35 | 449 | 128 | 380[e] | 428 (382)[e] | NA |
| 284 | 1860 | 1.28 | 236 | 54 | 368[e] | 430 (370)[e] | NA |
| 198 | 7990 | 2.52 | 436 | 174 | 384 | 448 (386) | 452 |
| 199 | 6890 | 1.50 | 421 | NO | 384 | 424 (386) | NA |
| 201 | 14100 | 1.68 | 405 | 76 | 388 | 450 (378) | 460 |
| 273 | 5190 | 1.38 | 409 | 175 | 364 | 442 (366) | 468 |

[a]weight average molecular weight, determined by size exclusion chromatography in THF using polystyrene standard
[b]as solid state thin film
[c]as solid state thin film, the number in the parenthesis is the excitation wavelength
[d]not available
[e]in toluene solution
[f]not observed The invention has been described in detail with particular reference to certain preferred embodiments thereof, but it will be understood that variations and modifications can be effected within the spirit and scope of the invention.

PARTS LIST

| | |
|---|---|
| 101 | substrate |
| 103 | anode |
| 105 | hole-injecting layer |
| 107 | hole transporting layer |
| 109 | light-emitting layer |
| 111 | electron-transporting layer |
| 113 | cathode |
| 250 | voltage-current source |
| 260 | electrical conductors |

What is claimed is:

1. An electroluminescent device, comprising:
   a) a spaced-apart anode and cathode; and
   b) an emissive layer disposed between the spaced-apart anode and cathode and including an organic compound having a complex fluorene structure represented the following Formula (I):

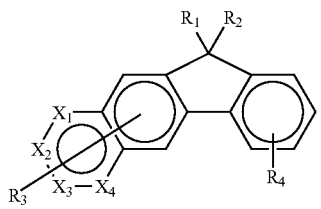
(I)

wherein:
   $X_1$, $X_2$, $X_3$, and $X_4$ include carbon atoms and at least one nitrogen atom; $R_3$, and $R_4$ are substituents each being individually hydrogen, or amino, or alkyl, or alkenyl, or alkynyl, or alkoxy of from 1 to 40 carbon atoms; aryl or substituted aryl of from 6 to 60 carbon atoms; or heteroaryl or substituted heteroaryl of from 4 to 60 carbons; or F, Cl, or Br; or a cyano group; or a nitro group; or $R_3$, or $R_4$ or both are groups that form fused aromatic or heteroaromatic rings; and $R_1$ and $R_2$ together form a cyclic ring having 3 to 20 carbon, nitrogen, sulfur or oxygen atoms; or $R_1$ and $R_2$ together form a double bond moiety.

2. An electroluminescent device, comprising:
   a) a spaced-apart anode and cathode; and
   b) an emissive layer disposed between the spaced-apart anode and cathode and including an organic compound having a complex fluorene structure represented by the following Formula (I):

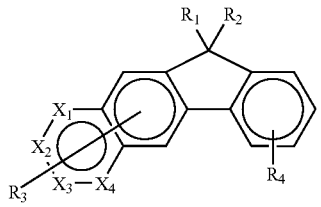
(I)

wherein:
   $X_1$, $X_2$, $X_3$, and $X_4$ include carbon or nitrogen atoms; $R_3$, and $R_4$ are substituents each being individually hydrogen, or amino, or alkyl, or alkenyl, or alkynyl, or alkoxy of from 1 to 40 carbon atoms; aryl or substituted aryl of from 6 to 60 carbon atoms; or heteroaryl or substituted heteroaryl of from 4 to 60 carbons; or F, Cl, or Br; or a cyano group; or a nitro group; or $R_3$, or $R_4$ or both are groups that form fused aromatic or heteroaromatic rings; and $R_1$ and $R_2$ together form a cyclic ring having 3 to 20 carbon, nitrogen, sulfur or oxygen atoms; or $R_1$ and $R_2$ together form a double bond moiety wherein the organic compound having the complex fluorene structure is a molecule represented by Formula (II):

$$(Y_1)y_1\text{—complex fluorene (I)—}(Y_2)y_2 \quad (II)$$

wherein:
   $Y_1$ and $Y_2$ each individually represent a substituted or unsubstituted alkyl, alkenyl, alkynyl, aryl, or heteroaryl or other conjugated groups, and $y_1$ and $y_2$ are integers from 1 to 6, and wherein $Y_1$ and $Y_2$ are the same or different.

3. An electroluminescent device, comprising:
   a) a spaced-apart anode and cathode; and
   b) an emissive layer disposed between the spaced-apart anode and cathode and including an organic compound having a complex fluorene structure represented by the following Formula (I):

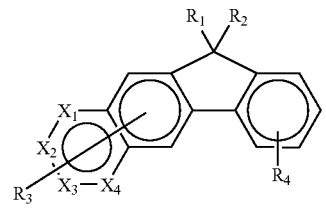
(I)

wherein:
   $X_1$, $X_2$, $X_3$, and $X_4$ include carbon or nitrogen atoms; $R_3$, and $R_4$ are substituents each being individually hydrogen, or amino, or alkyl, or alkenyl, or alkynyl, or alkoxy of from 1 to 40 carbon atoms; aryl or substituted aryl of from 6 to 60 carbon atoms; or heteroaryl or substituted heteroaryl of from 4 to 60 carbons; or F, Cl, or Br; or a cyano group; or a nitro group: or $R_3$, or $R_4$ or both are groups that form fused aromatic or heteroaromatic rings; and $R_1$ and $R_2$ together form a cyclic ring having 3 to 20 carbon, nitrogen, sulfur or oxygen atoms; or $R_1$ and $R_2$ together form a double bond moiety wherein the organic compound having the complex fluorene structure is part of a polymer structure.

4. The polymer of claim 3 is represented by repeating units of Formula (III) or Formula (IV)

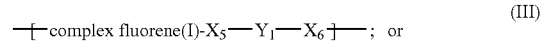
(III)

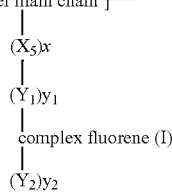
(IV)

wherein:
   $X_5$ and $X_6$ are linking groups, $Y_1$ and $Y_2$ are each individually represented as a substituted or unsubstituted alkyl, alkenyl, alkynyl, aryl, or heteroaryl or other conjugated groups, and $y_1$ and $y_2$ are integers from 0 to 6, and x is an integer from 0 to 6.

* * * * *